(12) United States Patent
Grassot et al.

(10) Patent No.: US 12,167,991 B2
(45) Date of Patent: *Dec. 17, 2024

(54) GAMMA-HYDROXYBUTYRATE COMPOSITIONS HAVING IMPROVED PHARMACOKINETICS IN THE FED STATE

(71) Applicant: Flamel Ireland Limited, Dublin (IE)

(72) Inventors: Julien Grassot, Lyons (FR); Cendrine Grangeon, Villeurbanne (FR); Jordan Dubow, Lyons (FR)

(73) Assignee: Flamel Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/758,344

(22) Filed: Jun. 28, 2024

(65) Prior Publication Data

US 2024/0350437 A1 Oct. 24, 2024

Related U.S. Application Data

(63) Continuation of application No. 17/837,740, filed on Jun. 10, 2022, which is a continuation of application No. 16/804,966, filed on Feb. 28, 2020, now Pat. No. 11,400,065.

(60) Provisional application No. 62/857,008, filed on Jun. 4, 2019, provisional application No. 62/812,699, filed on Mar. 1, 2019.

(51) Int. Cl.
*A61K 31/19* (2006.01)
*A61K 9/00* (2006.01)

(52) U.S. Cl.
CPC ............ *A61K 31/19* (2013.01); *A61K 9/0053* (2013.01); *A61K 9/009* (2013.01); *A61K 9/0095* (2013.01)

(58) Field of Classification Search
CPC .................................................. A61K 31/19
See application file for complete search history.

(56) References Cited

U.S. PATENT DOCUMENTS

| | | |
|---|---|---|
| 3,051,619 A | 8/1962 | Marie et al. |
| 3,419,588 A | 12/1968 | De et al. |
| 4,221,778 A | 9/1980 | Raghunathan |
| 4,374,441 A | 2/1983 | Carter et al. |
| 4,393,236 A | 7/1983 | Klosa |
| 4,510,128 A | 4/1985 | Khanna |
| 4,524,217 A | 6/1985 | Davenport et al. |
| 4,687,662 A | 8/1987 | Schobel |
| 4,738,985 A | 4/1988 | Kluger et al. |
| 4,916,161 A | 4/1990 | Patell |
| 4,939,949 A | 7/1990 | Langenberg |
| 4,976,351 A | 12/1990 | Mangini et al. |
| 4,983,632 A | 1/1991 | Gessa et al. |
| 5,294,430 A | 3/1994 | Borch et al. |
| 5,326,856 A | 7/1994 | Coughlin et al. |
| 5,364,842 A | 11/1994 | Justice et al. |
| 5,380,937 A | 1/1995 | Koehler et al. |
| 5,415,870 A | 5/1995 | Gergely et al. |
| 5,424,218 A | 6/1995 | Miljanich et al. |
| 5,426,120 A | 6/1995 | Crepaldi et al. |
| 5,449,761 A | 9/1995 | Belinka, Jr. et al. |
| 5,527,885 A | 6/1996 | Coughlin et al. |
| 5,578,288 A | 11/1996 | Belinka, Jr. et al. |
| 5,578,484 A | 11/1996 | Horoszewicz |
| 5,585,468 A | 12/1996 | Coughlin et al. |
| 5,587,454 A | 12/1996 | Justice et al. |
| 5,593,656 A | 1/1997 | Belinka, Jr. et al. |
| 5,594,030 A | 1/1997 | Conte et al. |
| 5,753,708 A | 5/1998 | Koehler et al. |
| 5,758,095 A | 5/1998 | Albaum et al. |
| 5,763,202 A | 6/1998 | Horoszewicz |
| 5,795,864 A | 8/1998 | Amstutz et al. |
| 5,833,599 A | 11/1998 | Schrier et al. |
| 5,840,331 A | 11/1998 | Van Cauter et al. |
| 5,845,255 A | 12/1998 | Mayaud |
| 5,891,849 A | 4/1999 | Amstutz et al. |
| 5,955,106 A | 9/1999 | Moeckel et al. |
| 5,990,162 A | 11/1999 | Scharf |
| 6,014,631 A | 1/2000 | Teagarden et al. |
| 6,022,562 A | 2/2000 | Autant et al. |
| 6,054,429 A | 4/2000 | Bowersox et al. |
| 6,067,524 A | 5/2000 | Byerly et al. |
| 6,103,292 A | 8/2000 | Del Vecchio |
| 6,112,182 A | 8/2000 | Akers et al. |
| 6,184,205 B1 | 2/2001 | Sparks et al. |
| 6,255,307 B1 | 7/2001 | Cox et al. |
| 6,317,719 B1 | 11/2001 | Schrier et al. |
| 6,322,819 B1 | 11/2001 | Burnside et al. |
| 6,356,873 B1 | 3/2002 | Teagarden et al. |
| 6,361,938 B1 | 3/2002 | O'Mahony et al. |
| 6,384,020 B1 | 5/2002 | Flanner et al. |

(Continued)

FOREIGN PATENT DOCUMENTS

| | | |
|---|---|---|
| AR | 062556 A1 | 11/2008 |
| AR | 063201 A1 | 1/2009 |

(Continued)

OTHER PUBLICATIONS

Notice of Allowance for U.S. Appl. No. 18/368,403, issued on Jul. 29, 2024, 11 pages.
Notice of Allowance for U.S. Appl. No. 18/388,699, issued on Jul. 24, 2024, 9 pages.
Office Action for Argentina Patent Application No. 20170102053, mailed Jun. 14, 2024, 13 pages.
Office Action for Canadian Application No. 3,200,357, mailed on Aug. 7, 2024, 4 pages.
Notice of Allowance for U.S. Appl. No. 18/531,095 dated Aug. 14, 2024, 9 pages.
Notice of Allowance for U.S. Appl. No. 18/537,318 dated Aug. 14, 2024, 9 pages.
Notice of Allowance for U.S. Appl. No. 18/539,946 dated Aug. 14, 2024, 9 pages.
Office Action for U.S. Appl. No. 17/666,201, mailed on Dec. 23, 2022,18pages.

(Continued)

*Primary Examiner* — Rei Tsang Shiao
(74) *Attorney, Agent, or Firm* — POLSINELLI PC

(57) ABSTRACT

Oral pharmaceutical compositions of sodium oxybate having improved pharmacokinetic properties when administered less than two hours after eating are provided, and therapeutic uses thereof.

23 Claims, 10 Drawing Sheets

(56) References Cited

U.S. PATENT DOCUMENTS

| | | |
|---|---|---|
| 6,432,920 B1 | 8/2002 | Sparks et al. |
| 6,436,430 B1 | 8/2002 | Mulye |
| 6,436,998 B1 | 8/2002 | Cacciaglia et al. |
| 6,461,197 B2 | 10/2002 | Crane, Jr. et al. |
| 6,472,431 B2 | 10/2002 | Cook et al. |
| 6,472,432 B1 | 10/2002 | Perricone |
| 6,495,598 B1 | 12/2002 | Yoneda et al. |
| 6,565,872 B2 | 5/2003 | Wu et al. |
| 6,599,905 B2 | 7/2003 | Cox et al. |
| 6,638,522 B1 | 10/2003 | Mulye |
| 6,699,973 B1 | 3/2004 | O'Mahony et al. |
| 6,703,362 B1 | 3/2004 | Alvarez et al. |
| 6,780,889 B2 | 8/2004 | Cook et al. |
| 6,803,464 B2 | 10/2004 | Edney et al. |
| 6,913,768 B2 | 7/2005 | Couch et al. |
| 7,015,200 B2 | 3/2006 | Mamelak et al. |
| 7,072,840 B1 | 7/2006 | Mayaud |
| 7,135,457 B1 | 11/2006 | Alvarez et al. |
| 7,238,367 B2 | 7/2007 | Tardi et al. |
| 7,262,219 B2 | 8/2007 | Cook et al. |
| 7,268,109 B2 | 9/2007 | Ellis et al. |
| 7,524,812 B2 | 4/2009 | Ellis et al. |
| 7,566,766 B2 | 7/2009 | O'Mahony et al. |
| 7,568,822 B2 | 8/2009 | Ibrahim |
| 7,572,605 B2 | 8/2009 | Mamelak et al. |
| 7,668,730 B2 | 2/2010 | Reardan et al. |
| 7,683,024 B2 | 3/2010 | Chan et al. |
| 7,709,445 B2 | 5/2010 | Soula et al. |
| 7,744,921 B2 | 6/2010 | Tardi et al. |
| 7,765,106 B2 | 7/2010 | Reardan et al. |
| 7,765,107 B2 | 7/2010 | Reardan et al. |
| 7,797,171 B2 | 9/2010 | Reardan et al. |
| 7,833,973 B2 | 11/2010 | Ellis et al. |
| 7,842,676 B2 | 11/2010 | Janoff et al. |
| 7,850,090 B2 | 12/2010 | Ollendick |
| 7,851,506 B2 | 12/2010 | Cook et al. |
| 7,879,362 B2 | 2/2011 | Castan et al. |
| 7,895,059 B2 | 2/2011 | Reardan et al. |
| 7,906,145 B2 | 3/2011 | Castan et al. |
| 7,956,030 B2 | 6/2011 | Ellis et al. |
| 7,977,307 B2 | 7/2011 | Ellis et al. |
| 8,022,279 B2 | 9/2011 | Mayer et al. |
| 8,062,667 B2 | 11/2011 | Mehta et al. |
| 8,084,045 B2 | 12/2011 | Pouliquen et al. |
| 8,092,828 B2 | 1/2012 | Louie et al. |
| 8,101,209 B2 | 1/2012 | Legrand et al. |
| 8,193,211 B2 | 6/2012 | Liang et al. |
| 8,202,537 B2 | 6/2012 | Mehta et al. |
| 8,202,542 B1 | 6/2012 | Mehta et al. |
| 8,263,125 B2 | 9/2012 | Vaya et al. |
| 8,263,650 B2 | 9/2012 | Cook et al. |
| 8,268,774 B2 | 9/2012 | Ellis et al. |
| 8,287,848 B2 | 10/2012 | Mehta et al. |
| 8,287,903 B2 | 10/2012 | Mehta et al. |
| 8,324,275 B2 | 12/2012 | Cook et al. |
| 8,337,890 B2 | 12/2012 | Mehta et al. |
| 8,431,806 B2 | 4/2013 | Mayer et al. |
| 8,445,023 B2 | 5/2013 | Guimberteau et al. |
| 8,457,988 B1 | 6/2013 | Reardan et al. |
| 8,461,197 B2 | 6/2013 | Tung |
| 8,461,203 B2 | 6/2013 | Cook et al. |
| 8,465,765 B2 | 6/2013 | Mehta et al. |
| 8,486,924 B2 | 7/2013 | Ansell et al. |
| 8,491,935 B2 | 7/2013 | Mehta et al. |
| 8,507,003 B2 | 8/2013 | Jorda et al. |
| 8,512,688 B2 | 8/2013 | Mehta et al. |
| 8,513,198 B2 | 8/2013 | Ellis et al. |
| 8,518,437 B2 | 8/2013 | Tardi et al. |
| 8,529,954 B2 | 9/2013 | Lebon et al. |
| 8,563,033 B1 | 10/2013 | Mehta et al. |
| 8,589,182 B1 | 11/2013 | Reardan et al. |
| 8,591,922 B1 | 11/2013 | Allphin et al. |
| 8,597,684 B2 | 12/2013 | Mehta et al. |
| 8,598,191 B2 | 12/2013 | Liang et al. |
| 8,609,651 B2 | 12/2013 | Jamieson et al. |
| 8,623,409 B1 | 1/2014 | Mehta et al. |
| 8,652,523 B2 | 2/2014 | Guimberteau et al. |
| 8,652,529 B2 | 2/2014 | Guimberteau et al. |
| 8,653,033 B2 | 2/2014 | Ellis et al. |
| 8,679,540 B2 | 3/2014 | Bonnet-Gonnet et al. |
| 8,680,228 B2 | 3/2014 | Guo et al. |
| 8,707,348 B2 | 4/2014 | Sakhartov et al. |
| 8,716,279 B2 | 5/2014 | Jamieson et al. |
| 8,731,963 B1 | 5/2014 | Reardan et al. |
| 8,734,850 B2 | 5/2014 | Castan et al. |
| 8,747,902 B2 | 6/2014 | Mehta et al. |
| 8,759,394 B2 | 6/2014 | Tung et al. |
| 8,765,178 B2 | 7/2014 | Parikh et al. |
| 8,765,680 B2 | 7/2014 | Ellis et al. |
| 8,771,735 B2 | 7/2014 | Rourke et al. |
| 8,772,306 B1 | 7/2014 | Eller |
| 8,778,301 B2 | 7/2014 | Mamelak et al. |
| 8,778,390 B2 | 7/2014 | Mehta et al. |
| 8,778,398 B2 | 7/2014 | Rourke et al. |
| 8,790,700 B2 | 7/2014 | Mehta et al. |
| 8,821,935 B2 | 9/2014 | Guimberteau et al. |
| 8,859,619 B2 | 10/2014 | Cook et al. |
| 8,883,217 B2 | 11/2014 | Mehta et al. |
| 8,901,173 B2 | 12/2014 | Allphin et al. |
| 8,916,202 B2 | 12/2014 | Lebon et al. |
| 8,952,029 B2 | 2/2015 | Eller |
| 8,952,062 B2 | 2/2015 | Cook et al. |
| 8,956,649 B2 | 2/2015 | Mehta et al. |
| 8,999,386 B2 | 4/2015 | Tu et al. |
| 8,999,392 B2 | 4/2015 | Suplie et al. |
| 9,023,400 B2 | 5/2015 | Guimberteau et al. |
| 9,040,083 B2 | 5/2015 | Mehta et al. |
| 9,050,302 B2 | 6/2015 | Eller |
| 9,132,107 B2 | 9/2015 | Allphin et al. |
| 9,180,100 B2 | 11/2015 | Tu et al. |
| 9,180,104 B2 | 11/2015 | Nelson et al. |
| 9,198,864 B2 | 12/2015 | Mehta et al. |
| 9,226,910 B2 | 1/2016 | Khayrallah et al. |
| 9,271,931 B2 | 3/2016 | Tardi et al. |
| 9,295,642 B2 | 3/2016 | Tu et al. |
| 9,359,290 B2 | 6/2016 | Khayrallah et al. |
| 9,408,823 B2 | 8/2016 | Nelson et al. |
| 9,427,429 B2 | 8/2016 | Gray |
| 9,486,426 B2 | 11/2016 | Eller |
| 9,522,191 B2 | 12/2016 | Mehta et al. |
| 9,539,330 B2 | 1/2017 | Cook et al. |
| 9,545,399 B2 | 1/2017 | Tu et al. |
| 9,549,989 B2 | 1/2017 | Mehta et al. |
| 9,555,017 B2 | 1/2017 | Allphin et al. |
| 9,561,179 B2 | 2/2017 | Castan et al. |
| 9,585,863 B2 | 3/2017 | Khayrallah et al. |
| 9,649,291 B2 | 5/2017 | Khayrallah et al. |
| 9,675,703 B2 | 6/2017 | Mehta et al. |
| 9,675,704 B2 | 6/2017 | Mehta et al. |
| 9,707,270 B2 | 7/2017 | Ellis et al. |
| 9,770,514 B2 | 9/2017 | Ghebre-Sellassie et al. |
| 9,795,567 B2 | 10/2017 | Rourke et al. |
| 9,801,852 B2 | 10/2017 | Allphin |
| 9,814,684 B2 | 11/2017 | Castan et al. |
| 9,844,544 B2 | 12/2017 | Tu et al. |
| 9,844,545 B2 | 12/2017 | Tu et al. |
| RE46,686 E | 1/2018 | Bonnet-Gonnet et al. |
| 9,867,797 B2 | 1/2018 | Nelson et al. |
| 9,920,311 B2 | 3/2018 | Abribat |
| 9,943,488 B2 | 4/2018 | Suplie et al. |
| 10,004,693 B2 | 6/2018 | Castan et al. |
| 10,028,912 B2 | 7/2018 | Cabral-Lilly et al. |
| 10,052,289 B2 | 8/2018 | Meyrueix et al. |
| 10,058,507 B2 | 8/2018 | Tardi et al. |
| RE47,084 E | 10/2018 | Castan et al. |
| 10,086,087 B2 | 10/2018 | Mehta et al. |
| 10,092,511 B2 | 10/2018 | Castan et al. |
| 10,105,341 B2 | 10/2018 | Khayrallah et al. |
| 10,172,958 B2 | 1/2019 | Mehta et al. |
| 10,174,302 B1 | 1/2019 | Friedrich et al. |
| 10,183,939 B2 | 1/2019 | Bingham et al. |
| 10,195,151 B2 | 2/2019 | Allphin et al. |
| 10,195,168 B2 | 2/2019 | Allphin et al. |
| 10,213,400 B2 | 2/2019 | Eller |

(56) References Cited

U.S. PATENT DOCUMENTS

| | | |
|---|---|---|
| 10,259,780 B2 | 4/2019 | Khayrallah et al. |
| 10,272,062 B2 | 4/2019 | Megret et al. |
| 10,307,463 B2 | 6/2019 | Ellis et al. |
| 10,398,662 B1 | 9/2019 | Allphin et al. |
| 10,457,627 B2 | 10/2019 | Xiang et al. |
| 10,501,401 B2 | 12/2019 | Xiang et al. |
| 10,507,203 B2 | 12/2019 | Tu et al. |
| 10,512,609 B2 | 12/2019 | Allphin et al. |
| 10,618,886 B1 | 4/2020 | Xiang et al. |
| 10,640,451 B2 | 5/2020 | Xiang et al. |
| 10,640,476 B2 | 5/2020 | Xiang et al. |
| 10,668,163 B2 | 6/2020 | Mehta et al. |
| 10,675,258 B2 | 6/2020 | Allphin et al. |
| 10,683,262 B2 | 6/2020 | Xiang et al. |
| 10,710,958 B2 | 7/2020 | Hurley et al. |
| 10,730,853 B2 | 8/2020 | Xiang et al. |
| 10,736,866 B2 | 8/2020 | Megret et al. |
| 10,758,488 B2 | 9/2020 | Allphin et al. |
| 10,774,031 B2 | 9/2020 | Xiang et al. |
| 10,813,885 B1 | 10/2020 | Allphin et al. |
| 10,829,443 B2 | 11/2020 | Nelson et al. |
| 10,836,714 B2 | 11/2020 | Xiang et al. |
| 10,857,143 B2 | 12/2020 | Tu et al. |
| 10,858,394 B2 | 12/2020 | Xiang et al. |
| 10,864,181 B2 | 12/2020 | Eller |
| 10,882,832 B2 | 1/2021 | Xiang et al. |
| 10,889,572 B2 | 1/2021 | Xiang et al. |
| 10,903,276 B2 | 1/2021 | Chan et al. |
| 10,905,775 B2 | 2/2021 | Mayer et al. |
| 10,912,754 B2 | 2/2021 | Carter et al. |
| 10,925,844 B2 * | 2/2021 | Grassot ............... A61K 9/5015 |
| 10,933,143 B2 | 3/2021 | Mehta et al. |
| 10,940,133 B1 | 3/2021 | Zomorodi |
| 10,941,107 B2 | 3/2021 | Xiang et al. |
| 10,952,986 B2 | 3/2021 | Megret et al. |
| 10,959,956 B2 | 3/2021 | Allphin et al. |
| 10,959,976 B2 | 3/2021 | Carter et al. |
| 10,966,931 B2 | 4/2021 | Allphin et al. |
| 10,968,202 B2 | 4/2021 | Xiang et al. |
| 10,973,795 B2 | 4/2021 | Megret et al. |
| 10,987,310 B2 | 4/2021 | Allphin et al. |
| 11,000,498 B2 | 5/2021 | Megret et al. |
| 11,033,530 B2 | 6/2021 | Allphin |
| 11,046,946 B2 | 6/2021 | Abribat |
| 11,052,061 B2 | 7/2021 | Megret et al. |
| 11,065,224 B2 | 7/2021 | Megret et al. |
| 11,072,579 B2 | 7/2021 | Khayrallah et al. |
| 11,077,079 B1 | 8/2021 | Allphin et al. |
| 11,090,269 B1 | 8/2021 | Allphin et al. |
| 11,147,782 B1 | 10/2021 | Allphin et al. |
| 11,207,270 B2 | 12/2021 | Allphin et al. |
| 11,364,215 B1 | 6/2022 | Allphin et al. |
| 11,400,052 B2 | 8/2022 | Walsh et al. |
| 11,400,065 B2 * | 8/2022 | Grassot ............... A61K 9/0053 |
| 11,504,347 B1 | 11/2022 | Grassot et al. |
| 11,583,510 B1 | 2/2023 | Grassot et al. |
| 11,602,512 B1 | 3/2023 | Dubow et al. |
| 11,602,513 B1 | 3/2023 | Dubow et al. |
| 11,766,418 B2 | 9/2023 | Dubow et al. |
| 11,826,335 B2 | 11/2023 | Dubow et al. |
| 11,839,597 B2 | 12/2023 | Megret et al. |
| 11,896,572 B2 | 2/2024 | Dubow et al. |
| 11,986,451 B1 | 5/2024 | Mégret et al. |
| 2002/0077334 A1 | 6/2002 | Cook et al. |
| 2003/0091632 A1 | 5/2003 | Campbell et al. |
| 2003/0180249 A1 | 9/2003 | Khanna et al. |
| 2004/0092455 A1 | 5/2004 | Mamelak et al. |
| 2005/0031688 A1 | 2/2005 | Ayala |
| 2005/0037077 A1 | 2/2005 | Legrand et al. |
| 2005/0113366 A1 | 5/2005 | Bourguignon et al. |
| 2005/0142192 A1 | 6/2005 | Benjamin et al. |
| 2005/0158384 A1 | 7/2005 | Couch et al. |
| 2005/0181050 A1 | 8/2005 | Hirsh et al. |
| 2005/0239838 A1 | 10/2005 | Edgar et al. |
| 2005/0244496 A1 | 11/2005 | Campbell et al. |
| 2006/0018933 A1 | 1/2006 | Vaya et al. |
| 2006/0024365 A1 | 2/2006 | Vaya et al. |
| 2006/0069040 A1 | 3/2006 | Mamelak |
| 2006/0078614 A1 | 4/2006 | Venkatesh |
| 2006/0182805 A1 | 8/2006 | Pfeiffer et al. |
| 2006/0204575 A1 | 9/2006 | Feng et al. |
| 2006/0210630 A1 | 9/2006 | Liang et al. |
| 2006/0228410 A1 | 10/2006 | Dumont et al. |
| 2007/0270491 A1 | 11/2007 | Cook et al. |
| 2008/0003267 A1 | 1/2008 | Spencer et al. |
| 2008/0004329 A1 | 1/2008 | Jamieson et al. |
| 2008/0020039 A1 | 1/2008 | Parikh et al. |
| 2008/0069871 A1 | 3/2008 | Vaughn et al. |
| 2008/0085304 A1 | 4/2008 | Baichwal et al. |
| 2008/0118571 A1 | 5/2008 | Lee et al. |
| 2008/0146549 A1 | 6/2008 | Coleman |
| 2008/0226564 A1 | 9/2008 | Weers et al. |
| 2008/0292700 A1 | 11/2008 | Nghiem et al. |
| 2008/0293698 A1 | 11/2008 | Johnson |
| 2009/0137565 A1 | 5/2009 | Frucht |
| 2009/0155357 A1 | 6/2009 | Muhuri |
| 2009/0220611 A1 | 9/2009 | Dargelas et al. |
| 2009/0317355 A1 | 12/2009 | Roth et al. |
| 2010/0112056 A1 | 5/2010 | Rourke et al. |
| 2010/0159001 A1 | 6/2010 | Cardinal et al. |
| 2010/0160363 A1 | 6/2010 | Cardinal et al. |
| 2010/0172989 A1 | 7/2010 | Roth et al. |
| 2010/0266701 A1 | 10/2010 | Guimberteau et al. |
| 2011/0034727 A1 | 2/2011 | Luchi et al. |
| 2011/0039929 A1 | 2/2011 | Cook et al. |
| 2011/0091537 A1 | 4/2011 | Castan et al. |
| 2011/0111027 A1 | 5/2011 | Rourke et al. |
| 2011/0119085 A1 | 5/2011 | Reardan et al. |
| 2011/0213004 A1 | 9/2011 | Kim et al. |
| 2011/0213298 A1 | 9/2011 | Pinnisi |
| 2011/0223241 A1 | 9/2011 | Tardi et al. |
| 2011/0293729 A1 | 12/2011 | Lebon et al. |
| 2012/0020833 A1 | 1/2012 | Cook et al. |
| 2012/0076865 A1 | 3/2012 | Allphin et al. |
| 2012/0148672 A1 | 6/2012 | Mehta et al. |
| 2012/0164228 A1 | 6/2012 | Suplie et al. |
| 2012/0202879 A1 | 8/2012 | Cook et al. |
| 2012/0202880 A1 | 8/2012 | Cook et al. |
| 2012/0207843 A1 | 8/2012 | Lebon et al. |
| 2013/0012565 A1 | 1/2013 | Tung et al. |
| 2013/0064814 A1 | 3/2013 | Gray |
| 2013/0143965 A1 | 6/2013 | Cook et al. |
| 2013/0230587 A1 | 9/2013 | Pilgaonkar et al. |
| 2013/0267595 A1 | 10/2013 | Cook et al. |
| 2013/0273159 A1 | 10/2013 | Howard et al. |
| 2013/0337078 A1 | 12/2013 | Mayer et al. |
| 2014/0004202 A1 | 1/2014 | Suplie et al. |
| 2014/0037745 A1 | 2/2014 | Liang et al. |
| 2014/0072624 A1 | 3/2014 | Jung et al. |
| 2014/0093578 A1 | 4/2014 | Mehta et al. |
| 2014/0127306 A1 | 5/2014 | Mehta et al. |
| 2014/0141090 A1 | 5/2014 | Wilson |
| 2014/0171506 A1 | 6/2014 | Allphin et al. |
| 2014/0188504 A1 | 7/2014 | Reardan et al. |
| 2014/0207480 A1 | 7/2014 | Reardan et al. |
| 2014/0207481 A1 | 7/2014 | Reardan et al. |
| 2014/0231300 A1 | 8/2014 | Mogna |
| 2014/0256709 A1 | 9/2014 | Glozman |
| 2014/0271896 A1 | 9/2014 | Abu Shmeis et al. |
| 2014/0275244 A1 | 9/2014 | Khayrallah et al. |
| 2014/0294916 A1 | 10/2014 | Tu et al. |
| 2014/0296830 A1 | 10/2014 | Gibson et al. |
| 2014/0316796 A1 | 10/2014 | Cox |
| 2014/0348917 A1 | 11/2014 | Rourke et al. |
| 2014/0371153 A1 | 12/2014 | Ellis et al. |
| 2015/0005334 A1 | 1/2015 | Shah et al. |
| 2015/0018414 A1 | 1/2015 | Khayrallah et al. |
| 2015/0073052 A1 | 3/2015 | Cook et al. |
| 2015/0182469 A1 | 7/2015 | Mehta et al. |
| 2015/0328168 A1 | 11/2015 | Daviaud-Venet et al. |
| 2016/0058704 A1 | 3/2016 | Tardi et al. |
| 2016/0068463 A1 | 3/2016 | Peoples et al. |
| 2016/0143854 A1 | 5/2016 | Tu et al. |
| 2016/0154947 A1 | 6/2016 | Reardan et al. |

(56) References Cited

U.S. PATENT DOCUMENTS

| | | |
|---|---|---|
| 2016/0180058 A1 | 6/2016 | Reardan et al. |
| 2016/0228379 A1 | 8/2016 | Kumar et al. |
| 2016/0271070 A1 | 9/2016 | Singh et al. |
| 2016/0310478 A1 | 10/2016 | Mehta et al. |
| 2016/0326086 A1 | 11/2016 | Tung et al. |
| 2016/0338966 A1 | 11/2016 | Guimberteau et al. |
| 2016/0346200 A1 | 12/2016 | Sommer et al. |
| 2016/0346216 A1 | 12/2016 | Chen |
| 2017/0042873 A1 | 2/2017 | Mehta et al. |
| 2017/0042874 A1 | 2/2017 | Mehta et al. |
| 2017/0119627 A1 | 5/2017 | Bhargava et al. |
| 2017/0224825 A1 | 8/2017 | Cook et al. |
| 2017/0319566 A1 | 11/2017 | Tu et al. |
| 2017/0340519 A9 | 11/2017 | Bhargava et al. |
| 2018/0000954 A1 | 1/2018 | Mehta et al. |
| 2018/0008539 A1 | 1/2018 | Singh et al. |
| 2018/0021284 A1 | 1/2018 | Mégret et al. |
| 2018/0042855 A1 | 2/2018 | Rourke et al. |
| 2018/0193277 A1 | 7/2018 | Suplie et al. |
| 2018/0200221 A1 | 7/2018 | Nelson et al. |
| 2018/0228822 A1 | 8/2018 | Krouse et al. |
| 2018/0263936 A1 | 9/2018 | Allphin et al. |
| 2018/0280357 A1 | 10/2018 | Maricich |
| 2018/0318222 A1 | 11/2018 | Allphin et al. |
| 2018/0346900 A1 | 12/2018 | Abribat |
| 2019/0015389 A1 | 1/2019 | Mehta et al. |
| 2019/0099395 A1 | 4/2019 | Khayrallah et al. |
| 2019/0151460 A1 | 5/2019 | Mehta et al. |
| 2019/0169589 A1 | 6/2019 | Friedrich et al. |
| 2019/0183806 A1 | 6/2019 | Guillard |
| 2019/0183836 A1 | 6/2019 | Mégret et al. |
| 2019/0194120 A1 | 6/2019 | Xiang et al. |
| 2019/0218168 A1 | 7/2019 | Xiang et al. |
| 2019/0269640 A1 | 9/2019 | Megret et al. |
| 2019/0269641 A1 | 9/2019 | Megret et al. |
| 2019/0274990 A1 | 9/2019 | Megret et al. |
| 2019/0282532 A1 | 9/2019 | Megret et al. |
| 2019/0328882 A1 | 10/2019 | Cook et al. |
| 2020/0085748 A1 | 3/2020 | Allphin et al. |
| 2020/0113840 A1 | 4/2020 | Allphin et al. |
| 2020/0113853 A1 | 4/2020 | Allphin et al. |
| 2020/0163926 A1 | 5/2020 | Nelson et al. |
| 2020/0163943 A1 | 5/2020 | Maricich et al. |
| 2020/0197347 A1 | 6/2020 | Megret et al. |
| 2020/0197377 A1 | 6/2020 | Maricich |
| 2020/0239416 A1 | 7/2020 | Xiang et al. |
| 2020/0261489 A1 | 8/2020 | Dimitrova et al. |
| 2020/0276142 A1 | 9/2020 | Grassot et al. |
| 2020/0290955 A1 | 9/2020 | Hurley et al. |
| 2020/0330393 A1 | 10/2020 | Walsh et al. |
| 2020/0338029 A1 | 10/2020 | Allphin et al. |
| 2020/0360293 A1 | 11/2020 | Guillard |
| 2020/0360319 A1 | 11/2020 | Grassot et al. |
| 2020/0368187 A1 | 11/2020 | Grassot et al. |
| 2020/0369599 A1 | 11/2020 | Xiang et al. |
| 2020/0375995 A1 | 12/2020 | Sudhakar et al. |
| 2020/0385367 A1 | 12/2020 | Richardson et al. |
| 2021/0015744 A1 | 1/2021 | Jain et al. |
| 2021/0015745 A1 | 1/2021 | Jain et al. |
| 2021/0020317 A1 | 1/2021 | Lillaney et al. |
| 2021/0032199 A1 | 2/2021 | Xiang et al. |
| 2021/0038588 A1 | 2/2021 | Tu et al. |
| 2021/0038734 A1 | 2/2021 | Mehta et al. |
| 2021/0047367 A1 | 2/2021 | Xiang et al. |
| 2021/0053912 A1 | 2/2021 | Hurley |
| 2021/0061791 A1 | 3/2021 | Xiang et al. |
| 2021/0069105 A1 | 3/2021 | Jain et al. |
| 2021/0069136 A1 | 3/2021 | Jain et al. |
| 2021/0077450 A1 | 3/2021 | Khayrallah et al. |
| 2021/0087177 A1 | 3/2021 | Xiang et al. |
| 2021/0093575 A1 | 4/2021 | Rourke et al. |
| 2021/0093603 A1 | 4/2021 | Hurley |
| 2021/0093623 A1 | 4/2021 | Tu et al. |
| 2021/0094925 A1 | 4/2021 | Xiang et al. |
| 2021/0121423 A1 | 4/2021 | Allphin et al. |
| 2021/0128502 A1 | 5/2021 | Eller |
| 2021/0162055 A1 | 6/2021 | Mehta et al. |
| 2021/0186907 A1 | 6/2021 | Skobieranda |
| 2021/0187004 A1 | 6/2021 | McMahon et al. |
| 2021/0205227 A1 | 7/2021 | Allphin et al. |
| 2021/0205257 A1 | 7/2021 | Carter et al. |
| 2021/0212970 A1 | 7/2021 | Eller |
| 2021/0213007 A1 | 7/2021 | Tu et al. |
| 2021/0244670 A1 | 8/2021 | Allphin et al. |
| 2021/0267928 A1 | 9/2021 | Megret et al. |
| 2021/0361601 A1 | 11/2021 | Skobieranda |
| 2022/0016066 A1 | 1/2022 | Megret et al. |
| 2022/0313635 A1 | 10/2022 | Grassot et al. |
| 2023/0210804 A1 | 7/2023 | Dubow et al. |
| 2024/0108594 A1 | 4/2024 | Mégret et al. |
| 2024/0165068 A1 | 5/2024 | Dubow et al. |
| 2024/0173286 A1 | 5/2024 | Dubow et al. |
| 2024/0180862 A1 | 6/2024 | Dubow et al. |
| 2024/0180864 A1 | 6/2024 | Dubow et al. |
| 2024/0226051 A1 | 7/2024 | Dubow et al. |

FOREIGN PATENT DOCUMENTS

| | | |
|---|---|---|
| AR | 109376 A1 | 11/2018 |
| AR | 112403 A1 | 10/2019 |
| AT | 536867 T | 12/2011 |
| AU | 775523 B2 | 8/2004 |
| AU | 2007269896 A1 | 1/2008 |
| AU | 2006214454 B2 | 5/2011 |
| AU | 2007290589 B2 | 4/2012 |
| AU | 2011359405 A1 | 8/2013 |
| AU | 2011232408 B2 | 7/2015 |
| AU | 2007227569 B9 | 4/2016 |
| AU | 2010352575 C1 | 11/2016 |
| AU | 2013359114 B2 | 1/2017 |
| AU | 2013302657 B2 | 8/2018 |
| AU | 2014248849 B2 | 8/2018 |
| AU | 2014223373 B2 | 12/2018 |
| AU | 2014240988 B9 | 1/2019 |
| AU | 2017202955 B2 | 1/2019 |
| AU | 2017300845 A1 | 1/2019 |
| AU | 2017324855 A1 | 3/2019 |
| AU | 2018278332 A1 | 1/2020 |
| AU | 2018287145 A1 | 2/2020 |
| AU | 2018309068 A8 | 2/2020 |
| AU | 2015314007 B2 | 3/2020 |
| AU | 2018312328 A1 | 3/2020 |
| AU | 2017406159 B2 | 5/2020 |
| AU | 2018375183 A1 | 6/2020 |
| AU | 2018398797 A1 | 6/2020 |
| AU | 2018388577 A1 | 7/2020 |
| AU | 2019206950 A1 | 8/2020 |
| AU | 2016328150 B2 | 10/2020 |
| AU | 2019252790 A1 | 10/2020 |
| AU | 2019383389 A1 | 5/2021 |
| AU | 2019283096 A1 | 7/2021 |
| AU | 2019420189 A1 | 7/2021 |
| AU | 2020231916 A1 | 8/2021 |
| BR | 9916063 A | 1/2002 |
| BR | PI0607003 A2 | 7/2009 |
| BR | PI0713801 A2 | 11/2012 |
| BR | PI0714907 A2 | 8/2014 |
| BR | 112015014007 A2 | 7/2017 |
| BR | 112015021403 A2 | 7/2017 |
| BR | 112013020537 A2 | 9/2017 |
| BR | 112019000848 A2 | 4/2019 |
| BR | 112019004479 A2 | 7/2019 |
| BR | 112015021012 A8 | 11/2019 |
| BR | 112015003120 A2 | 12/2019 |
| BR | 112019020464 A2 | 4/2020 |
| BR | 112019025286 A2 | 6/2020 |
| BR | 112020002289 A2 | 7/2020 |
| BR | 112019027479 A2 | 9/2020 |
| BR | 112020010976 A2 | 11/2020 |
| BR | 112020012417 A2 | 11/2020 |
| BR | 112020020865 A2 | 1/2021 |
| BR | 112020014189 A2 | 2/2021 |
| BR | 112012028035 B1 | 5/2021 |
| BR | PI0709606 B8 | 5/2021 |

(56) References Cited

FOREIGN PATENT DOCUMENTS

| | | |
|---|---|---|
| BR | 112021006027 A2 | 6/2021 |
| CA | 2217902 A1 | 1/1999 |
| CA | 2112663 C | 4/2002 |
| CA | 2510289 A1 | 7/2004 |
| CA | 2597910 A1 | 8/2006 |
| CA | 2654383 A1 | 1/2008 |
| CA | 2662197 A1 | 3/2008 |
| CA | 2423358 C | 5/2011 |
| CA | 2786819 A1 | 7/2011 |
| CA | 2880456 A1 | 2/2014 |
| CA | 2904045 A1 | 10/2014 |
| CA | 2917702 A1 | 1/2015 |
| CA | 2645855 C | 2/2015 |
| CA | 2540895 C | 8/2016 |
| CA | 2999367 A1 | 3/2017 |
| CA | 2798178 C | 6/2017 |
| CA | 2894876 C | 8/2017 |
| CA | 2740146 C | 11/2017 |
| CA | 3028878 A1 | 1/2018 |
| CA | 3036068 A1 | 3/2018 |
| CA | 3036071 A1 | 3/2018 |
| CA | 3039045 A1 | 4/2018 |
| CA | 2794171 C | 7/2018 |
| CA | 3056316 A1 | 9/2018 |
| CA | 2930900 C | 10/2018 |
| CA | 3058216 A1 | 10/2018 |
| CA | 3065522 A1 | 12/2018 |
| CA | 3068100 A1 | 12/2018 |
| CA | 3071544 A1 | 2/2019 |
| CA | 3071779 A1 | 2/2019 |
| CA | 2825991 C | 3/2019 |
| CA | 3083499 A1 | 6/2019 |
| CA | 3084120 A1 | 6/2019 |
| CA | 3085941 A1 | 6/2019 |
| CA | 3086153 A1 | 6/2019 |
| CA | 3097737 A1 | 6/2019 |
| CA | 3087912 A1 | 7/2019 |
| CA | 3095335 A1 | 10/2019 |
| CA | 2902948 C | 12/2019 |
| CA | 3102650 A1 | 12/2019 |
| CA | 3115122 A1 | 5/2020 |
| CN | 1236813 C | 1/2006 |
| CN | 101132780 A | 2/2008 |
| CN | 101478952 A | 7/2009 |
| CN | 101400343 B | 1/2012 |
| CN | 101528261 B | 7/2012 |
| CN | 102905688 A | 1/2013 |
| CN | 102917697 A | 2/2013 |
| CN | 102946869 A | 2/2013 |
| CN | 102958930 A | 3/2013 |
| CN | 103209966 A | 7/2013 |
| CN | 103209967 A | 7/2013 |
| CN | 102488652 B | 6/2014 |
| CN | 105073106 A | 11/2015 |
| CN | 105188677 A | 12/2015 |
| CN | 102917697 B | 1/2016 |
| CN | 102946869 B | 8/2016 |
| CN | 105848650 A | 8/2016 |
| CN | 105025892 B | 3/2018 |
| CN | 109789096 A | 5/2019 |
| CN | 109906078 A | 6/2019 |
| CN | 105873576 B | 7/2019 |
| CN | 109996540 A | 7/2019 |
| CN | 110049966 A | 7/2019 |
| CN | 110638804 A | 1/2020 |
| CN | 110638805 A | 1/2020 |
| CN | 110709386 A | 1/2020 |
| CN | 111094238 A | 5/2020 |
| CN | 111132663 A | 5/2020 |
| CN | 111201014 A | 5/2020 |
| CN | 111278807 A | 6/2020 |
| CN | 111315878 A | 6/2020 |
| CN | 111317730 A | 6/2020 |
| CN | 111356699 A | 6/2020 |
| CN | 111511355 A | 8/2020 |
| CN | 111770914 A | 10/2020 |
| CN | 111818937 A | 10/2020 |
| CN | 111836798 A | 10/2020 |
| CN | 106866733 B | 11/2020 |
| CN | 112004520 A | 11/2020 |
| CN | 112004802 A | 11/2020 |
| CN | 112135812 A | 12/2020 |
| CN | 112236149 A | 1/2021 |
| CN | 112566902 A | 3/2021 |
| CN | 108283000 B | 4/2021 |
| CN | 106866784 B | 5/2021 |
| CN | 107108588 B | 6/2021 |
| CN | 113061089 A | 7/2021 |
| CO | 2020001873 A2 | 4/2020 |
| DE | 60129122 T2 | 10/2007 |
| DK | 1278721 T3 | 10/2007 |
| DK | 2018160 T3 | 2/2012 |
| DK | 2428205 T3 | 10/2012 |
| DK | 2931268 T3 | 2/2018 |
| DK | 2961399 T3 | 2/2018 |
| DK | 2884961 T3 | 4/2019 |
| DK | 2675438 T3 | 5/2019 |
| DK | 2768484 T3 | 10/2019 |
| DK | 3335708 T3 | 2/2020 |
| DK | 3021838 T3 | 8/2020 |
| DK | 3335709 T3 | 10/2020 |
| EP | 0203768 A2 | 12/1986 |
| EP | 0235408 A1 | 9/1987 |
| EP | 0344704 A1 | 12/1989 |
| EP | 0616804 A1 | 9/1994 |
| EP | 0635265 A1 | 1/1995 |
| EP | 0709087 B1 | 12/1999 |
| EP | 0635265 B1 | 2/2000 |
| EP | 1140061 A2 | 10/2001 |
| EP | 1140061 B1 | 5/2003 |
| EP | 1316309 A1 | 6/2003 |
| EP | 1278721 B1 | 6/2007 |
| EP | 1853230 A2 | 11/2007 |
| EP | 2032125 A2 | 3/2009 |
| EP | 2056877 A2 | 5/2009 |
| EP | 2068933 A2 | 6/2009 |
| EP | 2018160 B1 | 12/2011 |
| EP | 1135150 B1 | 10/2012 |
| EP | 2428205 B1 | 10/2012 |
| EP | 2549987 A4 | 1/2015 |
| EP | 2968151 B1 | 4/2017 |
| EP | 2451486 B1 | 5/2017 |
| EP | 2760911 B1 | 11/2017 |
| EP | 2931268 B1 | 11/2017 |
| EP | 2961399 B1 | 11/2017 |
| EP | 1434572 B1 | 12/2017 |
| EP | 3353145 A1 | 8/2018 |
| EP | 2341910 B1 | 9/2018 |
| EP | 3418383 A1 | 12/2018 |
| EP | 2884961 B1 | 3/2019 |
| EP | 2675438 B1 | 4/2019 |
| EP | 3470067 A1 | 4/2019 |
| EP | 3487483 A1 | 5/2019 |
| EP | 2768484 B1 | 7/2019 |
| EP | 3353145 A4 | 7/2019 |
| EP | 3523275 A1 | 8/2019 |
| EP | 3572071 A1 | 11/2019 |
| EP | 3335708 B1 | 12/2019 |
| EP | 3595648 A1 | 1/2020 |
| EP | 3509581 A4 | 4/2020 |
| EP | 3642340 A1 | 4/2020 |
| EP | 3021838 B1 | 5/2020 |
| EP | 3509582 A4 | 5/2020 |
| EP | 3661484 A1 | 6/2020 |
| EP | 2566462 B1 | 7/2020 |
| EP | 3335709 B1 | 8/2020 |
| EP | 3695833 A1 | 8/2020 |
| EP | 3716997 A1 | 10/2020 |
| EP | 3727348 A1 | 10/2020 |
| EP | 3601235 A4 | 11/2020 |
| EP | 3737353 A1 | 11/2020 |
| EP | 3737665 A1 | 11/2020 |
| EP | 3740188 A1 | 11/2020 |
| EP | 3740189 A1 | 11/2020 |

(56) References Cited

FOREIGN PATENT DOCUMENTS

| | | |
|---|---|---|
| EP | 3668837 A4 | 12/2020 |
| EP | 3679051 A4 | 12/2020 |
| EP | 3773608 A1 | 2/2021 |
| EP | 3630072 A4 | 3/2021 |
| EP | 3661911 A4 | 4/2021 |
| EP | 3799867 A1 | 4/2021 |
| EP | 3802501 A1 | 4/2021 |
| ES | 2378573 T3 | 4/2012 |
| ES | 2396039 T3 | 2/2013 |
| ES | 2717469 T3 | 6/2019 |
| ES | 2721900 T3 | 8/2019 |
| GB | 922029 A | 3/1963 |
| GB | 2295390 A | 5/1996 |
| HK | 1156518 A | 6/2012 |
| HK | 1181639 A | 11/2013 |
| HK | 1201039 A1 | 8/2015 |
| HK | 1215181 A1 | 8/2016 |
| HK | 1215539 A1 | 9/2016 |
| HK | 1219236 A1 | 3/2017 |
| HK | 1256965 A1 | 10/2019 |
| HK | 1257965 A1 | 11/2019 |
| HK | 40002726 A | 3/2020 |
| HK | 40003964 A | 4/2020 |
| HK | 40009279 A | 6/2020 |
| HK | 40014757 A | 8/2020 |
| HK | 40027633 A | 1/2021 |
| HK | 40029219 A | 2/2021 |
| HK | 40029594 A | 2/2021 |
| HK | 40029856 A | 2/2021 |
| HK | 40031621 A | 3/2021 |
| HK | 40031646 A | 3/2021 |
| HK | 1182964 B | 4/2021 |
| HK | 1257033 B | 4/2021 |
| HK | 40033315 A | 4/2021 |
| HK | 40035049 A | 5/2021 |
| HK | 40038018 A | 6/2021 |
| ID | 201703439 A | 4/2017 |
| ID | 201906443 A | 8/2019 |
| ID | 201906490 A | 8/2019 |
| ID | 201907562 A | 10/2019 |
| IL | 143580 A | 5/2007 |
| IL | 194042 A | 6/2014 |
| IL | 239355 A | 5/2017 |
| IL | 222012 A | 11/2017 |
| IL | 222161 A | 11/2017 |
| IL | 227734 A | 8/2018 |
| IL | 236847 A | 5/2019 |
| IL | 240874 A | 6/2019 |
| IL | 241533 A | 2/2020 |
| IL | 275312 | 7/2020 |
| IL | 275444 | 8/2020 |
| IL | 265193 A | 4/2021 |
| IN | 200706499 P1 | 9/2007 |
| IN | 216331 B | 3/2008 |
| IN | 222233 B | 8/2008 |
| IN | 200808703 P1 | 5/2009 |
| IN | 200900401 P4 | 6/2009 |
| IN | 200901567 P1 | 6/2009 |
| IN | 201209462 P1 | 1/2016 |
| IN | 201505205 P4 | 7/2016 |
| IN | 201917009658 A | 6/2019 |
| IN | 201917013067 A | 6/2019 |
| IN | 201917017276 A | 8/2019 |
| IN | 342246 B | 7/2020 |
| IN | 342829 B | 7/2020 |
| IN | 202017008027 A | 8/2020 |
| IN | 202017008237 A | 10/2020 |
| IN | 202017045975 A | 2/2021 |
| IN | 361207 B | 3/2021 |
| JP | S5742651 A | 3/1982 |
| JP | S6212715 A | 1/1987 |
| JP | H0449212 A | 2/1992 |
| JP | H05508422 A | 11/1993 |
| JP | H06508839 A | 10/1994 |
| JP | H0753365 A | 2/1995 |
| JP | H08511257 A | 11/1996 |
| JP | H09104620 A | 4/1997 |
| JP | H10505604 A | 6/1998 |
| JP | 2001513552 A | 9/2001 |
| JP | 2002531515 A | 9/2002 |
| JP | 2004514732 A | 5/2004 |
| JP | 2006524207 A | 10/2006 |
| JP | 2007521231 A | 8/2007 |
| JP | 2007532689 A | 11/2007 |
| JP | 2008512386 A | 4/2008 |
| JP | 2008519847 A | 6/2008 |
| JP | 2008520633 A | 6/2008 |
| JP | 2008528571 A | 7/2008 |
| JP | 2009526825 A | 7/2009 |
| JP | 2009532331 A | 9/2009 |
| JP | 2011500865 A | 1/2011 |
| JP | 2012507532 A | 3/2012 |
| JP | 2012508784 A | 4/2012 |
| JP | 2013522373 A | 6/2013 |
| JP | 2014505094 A | 2/2014 |
| JP | 5479086 B2 | 4/2014 |
| JP | 5816091 B2 | 11/2015 |
| JP | 2016503002 A | 2/2016 |
| JP | 5925766 B2 | 5/2016 |
| JP | 5968300 B2 | 8/2016 |
| JP | 6215347 B2 | 10/2017 |
| JP | 6433440 B2 | 12/2018 |
| JP | 6516720 B2 | 5/2019 |
| JP | 6529495 B2 | 6/2019 |
| JP | 2019163298 A | 9/2019 |
| JP | 6683886 B2 | 4/2020 |
| JP | 2020100670 A | 7/2020 |
| JP | 6781150 B2 | 11/2020 |
| JP | 6824315 B2 | 2/2021 |
| JP | 6830671 B2 | 2/2021 |
| JP | 2021506752 A | 2/2021 |
| JP | 2021506984 A | 2/2021 |
| KR | 100602725 B1 | 7/2006 |
| KR | 20070104471 A | 10/2007 |
| KR | 20090031598 A | 3/2009 |
| KR | 20090043603 A | 5/2009 |
| KR | 101495146 B1 | 2/2015 |
| KR | 20150129695 A | 11/2015 |
| KR | 20160030955 A | 3/2016 |
| KR | 20160032127 A | 3/2016 |
| KR | 20180058738 A | 6/2018 |
| KR | 20190065311 A | 6/2019 |
| KR | 20190072561 A | 6/2019 |
| KR | 20190104510 A | 9/2019 |
| KR | 20190134711 A | 12/2019 |
| KR | 20200016889 A | 2/2020 |
| KR | 20200030065 A | 3/2020 |
| KR | 20200045489 A | 5/2020 |
| KR | 20200116102 A | 10/2020 |
| KR | 20200119234 A | 10/2020 |
| KR | 20200121780 A | 10/2020 |
| KR | 2180343 B1 | 11/2020 |
| KR | 2192554 B1 | 12/2020 |
| KR | 20210008478 A | 1/2021 |
| KR | 2239042 B1 | 4/2021 |
| KR | 20210094513 A | 7/2021 |
| MA | 29319 B1 | 3/2008 |
| MX | 01005884 A | 4/2002 |
| MX | 233001 B | 12/2005 |
| MX | 2007009923 A | 3/2008 |
| MX | 2008015083 A | 12/2008 |
| MX | 2009002310 A | 9/2009 |
| MX | 2015011242 A | 5/2016 |
| MX | 340591 B | 7/2016 |
| MX | 366681 B | 7/2019 |
| MX | 2019002606 A | 9/2019 |
| MX | 372447 B | 3/2020 |
| MX | 377251 B | 11/2020 |
| MX | 381381 B | 4/2021 |
| MY | 118612 A | 12/2004 |
| NO | 20073854 L | 11/2007 |
| NO | 326479 B1 | 12/2008 |
| NO | 20085158 L | 1/2009 |
| NO | 20091211 L | 5/2009 |

(56) References Cited

FOREIGN PATENT DOCUMENTS

| | | | |
|---|---|---|---|
| NZ | 512287 A | 12/2002 |
| NZ | 556562 A | 8/2010 |
| NZ | 572481 A | 3/2011 |
| NZ | 575744 A | 10/2011 |
| NZ | 595388 A | 12/2011 |
| OA | 14824 A | 1/2011 |
| PH | 12019500493 A1 | 5/2019 |
| PH | 12019500494 A1 | 6/2019 |
| PH | 12019500751 A1 | 8/2019 |
| PH | 12019502723 A1 | 7/2020 |
| PL | 192864 B1 | 12/2006 |
| PT | 1278721 E | 7/2007 |
| PT | 2931268 T | 2/2018 |
| PT | 2961399 T | 2/2018 |
| PT | 2768484 T | 10/2019 |
| PT | 3335708 T | 3/2020 |
| PT | 3021838 T | 9/2020 |
| PT | 3335709 T | 10/2020 |
| RS | 57077 B1 | 6/2018 |
| RU | 2210360 C1 | 8/2003 |
| RU | 2257917 C2 | 8/2005 |
| RU | 2435569 C2 | 12/2011 |
| RU | 2673239 C2 | 11/2018 |
| RU | 2725886 C1 | 7/2020 |
| RU | 2019110127 A | 10/2020 |
| RU | 2020101972 A | 7/2021 |
| SG | 136196 A1 | 11/2007 |
| SG | 11201504637 B | 10/2017 |
| SG | 11201505029 B | 11/2017 |
| SG | 11201901996 A1 | 4/2019 |
| SG | 11201901998 A1 | 4/2019 |
| SG | 11201903076 A1 | 5/2019 |
| SG | 11201911470 A1 | 12/2019 |
| SG | 11201912625 A1 | 1/2020 |
| SG | 11202000817 A1 | 2/2020 |
| SG | 11202000952 A1 | 2/2020 |
| SG | 11201507121 B | 5/2020 |
| SG | 11202004965 A1 | 6/2020 |
| SG | 11202006575 A1 | 8/2020 |
| TW | 513416 B | 12/2002 |
| TW | 200812649 A | 3/2008 |
| TW | 200815045 A | 4/2008 |
| TW | 200824693 A | 6/2008 |
| TW | I619492 B | 4/2018 |
| TW | 201831174 A | 9/2018 |
| TW | 201836596 A | 10/2018 |
| TW | 201840544 A | 11/2018 |
| TW | I639425 B | 11/2018 |
| TW | 201909904 A | 3/2019 |
| TW | 201919605 A | 6/2019 |
| TW | 201932448 A | 8/2019 |
| TW | I681770 B | 1/2020 |
| TW | 202014186 A | 4/2020 |
| TW | 202019880 A | 6/2020 |
| TW | I707677 B | 10/2020 |
| TW | I710552 B | 11/2020 |
| TW | I716458 B | 1/2021 |
| TW | I727362 B | 5/2021 |
| UY | 30442 A1 | 1/2008 |
| UY | 30561 A1 | 3/2008 |
| VN | 65599 A | 9/2019 |
| VN | 66223 A | 10/2019 |
| VN | 66257 A | 10/2019 |
| VN | 76195 A | 3/2021 |
| WO | 9428880 A1 | 12/1994 |
| WO | 9640105 A1 | 12/1996 |
| WO | 9909972 A1 | 3/1999 |
| WO | 0033862 A1 | 6/2000 |
| WO | 0038672 A2 | 7/2000 |
| WO | 0119361 A2 | 3/2001 |
| WO | 0224715 A2 | 3/2002 |
| WO | 0245684 A2 | 6/2002 |
| WO | 2004093884 A2 | 11/2004 |
| WO | 2005016318 A1 | 2/2005 |
| WO | 2005030174 A1 | 4/2005 |
| WO | 2005055983 A2 | 6/2005 |
| WO | 2005099671 A2 | 10/2005 |
| WO | 2006029155 A2 | 3/2006 |
| WO | 2006053186 A2 | 5/2006 |
| WO | 2006080029 A1 | 8/2006 |
| WO | 2006088814 A3 | 2/2007 |
| WO | 2007053698 A2 | 5/2007 |
| WO | 2007103200 A2 | 9/2007 |
| WO | 2007133203 A1 | 11/2007 |
| WO | 2007109104 A3 | 12/2007 |
| WO | 2008033351 A2 | 3/2008 |
| WO | 2008027395 A3 | 4/2008 |
| WO | 2008042218 A1 | 4/2008 |
| WO | 2008005240 A3 | 5/2008 |
| WO | 2008086804 A2 | 7/2008 |
| WO | 2008027357 A9 | 4/2009 |
| WO | 2009056550 A2 | 5/2009 |
| WO | 2009092818 A1 | 7/2009 |
| WO | 2009104080 A2 | 8/2009 |
| WO | 2010042759 A2 | 4/2010 |
| WO | 2010053691 A1 | 5/2010 |
| WO | 2010055260 A1 | 5/2010 |
| WO | 2010124046 A1 | 10/2010 |
| WO | 2011119839 A1 | 9/2011 |
| WO | 2011127252 A2 | 10/2011 |
| WO | 2011135461 A2 | 11/2011 |
| WO | 2011139271 A1 | 11/2011 |
| WO | 2011140310 A2 | 11/2011 |
| WO | 2012028688 A1 | 3/2012 |
| WO | 2012085656 A2 | 6/2012 |
| WO | 2012107652 A1 | 8/2012 |
| WO | 2012112140 A1 | 8/2012 |
| WO | 2012112492 A1 | 8/2012 |
| WO | 2012114342 A1 | 8/2012 |
| WO | 2013119231 A1 | 8/2013 |
| WO | 2014028610 A1 | 2/2014 |
| WO | 2014078014 A2 | 5/2014 |
| WO | 2014093791 A1 | 6/2014 |
| WO | 2014134380 A1 | 9/2014 |
| WO | 2014159340 A1 | 10/2014 |
| WO | 2015006685 A1 | 1/2015 |
| WO | 2015010014 A1 | 1/2015 |
| WO | 2015076821 A1 | 5/2015 |
| WO | 2015120006 A1 | 8/2015 |
| WO | 2015120110 A2 | 8/2015 |
| WO | 2015166473 A1 | 11/2015 |
| WO | 2016087952 A1 | 6/2016 |
| WO | 2016178132 A1 | 11/2016 |
| WO | 2017049470 A1 | 3/2017 |
| WO | 2017050259 A1 | 3/2017 |
| WO | 2017147375 A1 | 8/2017 |
| WO | 2017182851 A1 | 10/2017 |
| WO | 2018015563 A1 | 1/2018 |
| WO | 2018048862 A1 | 3/2018 |
| WO | 2018048871 A1 | 3/2018 |
| WO | 2018067971 A1 | 4/2018 |
| WO | 2018167303 A1 | 9/2018 |
| WO | 2018176343 A1 | 10/2018 |
| WO | 2018222954 A1 | 12/2018 |
| WO | 2018234492 A1 | 12/2018 |
| WO | 2019027941 A1 | 2/2019 |
| WO | 2019033330 A1 | 2/2019 |
| WO | 2019041361 A1 | 3/2019 |
| WO | 2019109018 A1 | 6/2019 |
| WO | 2019123269 A1 | 6/2019 |
| WO | 2019126214 A1 | 6/2019 |
| WO | 2019126215 A1 | 6/2019 |
| WO | 2019126218 A1 | 6/2019 |
| WO | 2019137381 A1 | 7/2019 |
| WO | 2019028340 A9 | 8/2019 |
| WO | 2019126216 A8 | 10/2019 |
| WO | 2019200251 A1 | 10/2019 |
| WO | 2019232724 A1 | 12/2019 |
| WO | 2019233447 A1 | 12/2019 |
| WO | 2020019247 A1 | 1/2020 |
| WO | 2020020189 A1 | 1/2020 |
| WO | 2020062251 A1 | 4/2020 |
| WO | 2020106735 A1 | 5/2020 |
| WO | 2020118165 A1 | 6/2020 |

(56) References Cited

FOREIGN PATENT DOCUMENTS

| WO | 2020143198 A1 | 7/2020 |
|---|---|---|
| WO | 2020178695 A1 | 9/2020 |
| WO | 2021078988 A1 | 4/2021 |
| WO | 2021127461 A1 | 6/2021 |
| WO | 2021133778 A1 | 7/2021 |
| WO | 2021168403 A1 | 8/2021 |
| ZA | 200104585 B | 6/2002 |
| ZA | 202000676 B | 1/2021 |

OTHER PUBLICATIONS

Office Action for U.S. Appl. No. 17/731,562, mailed on Apr. 14, 2023, 9 pages.
Office Action for U.S. Appl. No. 17/731,562, mailed on Jun. 14, 2023, 56 pages.
Office Action for U.S. Appl. No. 17/731,562, mailed on May 15, 2023, 19 pages.
Office Action for U.S. Appl. No. 17/896,483, mailed on Dec. 15, 2022,23 pages.
Office Action for U.S. Appl. No. 18/075,980, mailed on Apr. 6, 2023, 23 pages.
Office Action for U.S. Appl. No. 18/096,508, mailed on Apr. 25, 2023, 164 pages.
Office Action for U.S. Appl. No. 17/666,201 mailed on Aug. 26, 2022, 18 pages.
Ohta K.M., et al., "Development of a Simple Method for the Preparation of a Silica Gel Based Controlled Delivery System With a High Drug Content," European Journal of Pharmaceutical Sciences, 2005, vol. 26 (1), pp. 87-96.
Okun M.S., et al., "GHB: An Important Pharmacologic and Clinical Update," Journal of Pharmaceutical Sciences, 2001, vol. 4 (2), pp. 167-175.
Ondo W.G., et al., "Sodium Oxybate for Excessive Daytime Sleepiness in Parkinson's Disease: An Open-Lable Polysomnographic Study," Arch Neural, Oct. 2008, vol. 65 (10), pp. 1337-1340.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES).
Outlaw W.M., et al., "Dyspepsia and its Overlap with Irritable Bowel Syndrome," Current Gastroenterology Reports, 2006, vol. 8 (4), pp. 266-272.
Pai M.P., et al., "Drug Dosing Based on Weight and Body Surface Area: Mathematical Assumptions and Limitations in Obese Adults," Pharmacotherapy, Sep. 2012, vol. 32, No. 9, pp. 856-868.
Palatini P., et al., "Dose Dependent Absorption and Elimination of Gamma-Hydroxybutyric Acid in Healthy Volunteers," European Journal of Clinical Pharmacology, 1993, vol. 45 (4), pp. 353-356.
Pardi D., et al., "y-Hydroxybutyrate/Sodium Oxybate; Neurobiology, and Impact on Sleep and Wakefulness," Central Nervous System Drugs, 2006, vol. 20 (12), pp. 993-1018.
Parmar A., et al., "Clinical Characteristics of Cataplectic Attacks in Type 1 Narcolepsy," Current Neurology and Neuroscience Reports, 2020, vol. 20 (38), 9 pages.
Patil P., et al., "A Review on Ionotropic Gelation Method: Novel Approach for Controlled Gastroretentive Gelispheres," International Journal of Pharmacy and Pharmaceutical Sciences, 2012, vol. 4, Suppl. 4, pp. 27-32.
"Pharma Excipients," Eudragit® L 100-55, Description, Additional Information, Mar. 2022, 2 pages, Retrieved from the internet URL: https://www.pharmaexcipients.com/product/eudragit-l-100-55/.
"Phospholine Iodide," Physicians Desk Reference, 50th Edition, 1996, p. 2784.
Puguan J.M.C., et al., "Diffusion Characteristics of Different Molecular Weight Solutes in Ca-Alginate Gel Beads," Colloids and Surfaces A: Physicochemical and Engineering Aspects, 2015, vol. 469, pp. 158-165.
Raybon J.J., et al., "Pharmacokinetics and Pharmacodynamics of y-Hydroxybutyric Acid during Tolerance in Rats: Effects on Extracellular Dopamine," The Journal of Pharmacology and Experimental Therapeutics, 2007, vol. 320 (3), pp. 1252-1260.
Raymond C.R., "Polymethacrylates," Handbook of Pharmaceutical Excipients, Fifth Edition, Pharmaceutical Press, London, 2006, pp. 553-560.
Ritzhaupt A., et al., "The Characterization of Butyrate Transport across Pig and Human Colonic Luminal Membrane," Journal of Physiology, 1998, vol. 507 (3), pp. 819-830.
Roth R.H., et al., "y-Butyrolactone and y-Hydroxybutyric Acid-I, Distribution and Metabolism," Biochemical Pharmacology, 1966, vol. 15 (9), pp. 1333-1348.
Roth R.H., et al., "y-Butyrolactone and y-Hydroxybutyric Acid-II, The Pharmacologically Active Form," International Journal of Neuropharmacology, 1966, vol. 5 (6), pp. 421-428.
Roth T., et al., "Effect of Sodium Oxybate on Disrupted Night Time Sleep in Patients with Narcolepsy," Journal of Sleep Research, 2017, vol. 26, pp. 407-414.
Roxane Laboratories Inc., "Answer, Affirmative Defenses and Counterclaims to Plaintiff's Complaint," dated Jun. 1, 2011, 12 pages.
Roxane Laboratories Inc.," Answer, Affirmative Defenses and Counterclaims to Plaintiff's Complaint," dated Mar. 9, 2011, 13 pages.
Roxane Laboratories Inc., "Answer, Affirmative Defenses and Counterclaims to Plaintiff's Complaint," dated Nov. 9, 2012, 18 pages.
Roxane Laboratories Inc., "Answer, Affirmative Defenses and Counterclaims to Plaintiff's Complaint," dated Dec. 29, 2010, 21 pages.
Roxane Laboratories Inc., "Answer and Affirmative Defenses to Plaintiff's Complaint," dated Jan. 4, 2013, 8 pages.
Roxane Laboratories Inc., "Intitial Invalidity and Noninfringement Contentions Pursuant to Local Patent Rule 3.6," dated Apr. 14, 2011, 23 pages.
Rubbens J., et al., "Gastric and Duodenal Ethanol Concentrations after Intake of Alcoholic Beverages in Postprandial Conditions," Molecular Pharmaceutics, 2017, vol. 14 (12), pp. 4202-4208.
Rujivipat., et al., "Improved Drug Delivery to the Lower Intestinal Tract with Tablets Compression-Coated with Enteric/Nonenteric Polymer Powder Blends," European Journal of Pharmaceutics and Biopharmaceutics, 2010, vol. 76, pp. 486-492.
Russell I.J., et al., "Sodium Oxybate Relieves Pain and Improves Function in Fibromyalgia Syndrome," Arthritis Rheumatism, Jan. 2009, vol. 60 (1), pp. 299-309.
Russell J., et al., "Sodium Oxybate Reduces Pain, Fatigue, and Sleep Disturbance and Improves Functionality in Fibromyalgia: Results from a 14-week, Randomized, Double-Blind, Placebo-Controlled Study," Pain, 2011, vol. 152 (5), pp. 1007-1017.
Russell J., et al., "Sodium Oxybate Relieves Pain and Improves Function in Fibromyalgia Syndrome. A Randomized, Double-Blind, Placebo-Controlled, Multicenter Clinical Trial," Arthritis Rheumatism, 2009, vol. 60 (1), pp. 299-309.
Scammell T.E., "Narcolepsy," The New England Journal of Medicine, Dec. 31, 2015, vol. 373, No. 27, pp. 2654-2662.
Scharf M.B., et al., "Effect of Gamma-Hydroxybutyrate on Pain, Fatigue, and the Alpha Sleep Anomaly in Patients with Fibromyalgia. Preliminary Report," 1998, Journal of Rheumatology, 1998, vol. 25 (10), pp. 1986-1990.
Scharf M.B., et al., "GHB-New Hope for Narcoleptics?," Biol Psychiatry, 1989, vol. 26 (4), pp. 329-330.
Scharf M.B., et al., "Pharmacokinetics of Gammahydroxybutyrate (GHB) in Narcoleptic Patients," Sleep, 1998, vol. 21 (5), pp. 507-514.
Scharf M.B., et al., "The Effects of Sodium Oxybate on Clinical Symptoms and Sleep Patterns in Patients with Fibromyalgia," Journal of Rheumatology, May 2003, vol. 30 (5) pp. 1070-1074.
Scharf M.B., "The Effects and Effectiveness of y-Hydroxybutyrate in Patients with Narcolepsy," Journal of Clinical Psychiatry, Jun. 1985, vol. 46 (6), pp. 222-225.
Schie M.K.M.V., et al., "Improved Vigilance after Sodium Oxybate Treatment in Narcolepsy: A Comparison between In-Field and In-Laboratory Measurements," Journal of Sleep Research, 2016, vol. 25, pp. 486-496.
Scrima L., et al., "Effect of Gamma-Hydroxybutyrate on a Patient with Obstructive Sleep Apnea," Sleep Research, 1987, vol. 16, p. 137.

(56) References Cited

OTHER PUBLICATIONS

Scrima L., et al., "Effect of High Altitude on a Patient with Obstructive Sleep Apnea," Sleep Research, 1987, vol. 16, p. 427.
Scrima L., et al., "Efficacy of Gamma-Hydroxybutyrate Versus Placebo in Treating Narcolepsy-Cataplexy: Double- Blind Subjective Measures, "Biological Psychiatry, 1989, vol. 26 (4), pp. 331-343.
Scrima L., et al., "Gamma-Hydroxybutyrate Effects on Cataplexy and Sleep Attacks in Narcoleptics," Sleep Research, 1987, vol. 16, p. 134.
Scrima L., et al., "Narcolepsy," The New England Journal of Medicine, Jan. 24, 1991, vol. 324 (4), pp. 270-272.
Notice of Allowance for U.S. Appl. No. 16/527,633, mailed Jun. 9, 2021, 11 pages.
Notice of Allowance for U.S. Appl. No. 16/987,510, mailed Jan. 13, 2021, 8 pages.
Notice of Allowance for U.S. Appl. No. 17/194,780, mailed Sep. 13, 2023, 9 pages.
Notice of Allowance for U.S. Appl. No. 17/530,096 mailed on Mar. 26, 2024, 10 pages.
Notice of Allowance for U.S. Appl. No. 17/731,562, mailed on Feb. 23, 2024, 9 pages.
Notice of Allowance for U.S. Appl. No. 18/075,980, mailed Aug. 2, 2023, 9 pages.
Notice of Allowance for U.S. Appl. No. 18/096,508, mailed Aug. 9, 2023, 9 pages.
Notice of Allowance for U.S. Appl. No. 18/231,581, mailed on Nov. 13, 2023, 8 pages.
Notice of Allowance for U.S. Appl. No. 18/531,056, mailed on Jun. 5, 2024, 21 pages.
Notice of Allowance for U.S. Appl. No. 18/537,342, mailed on Jun. 6, 2024, 10 pages.
Notification of Issue for U.S. Appl. No. 16/281,235, issued Aug. 11, 2020, filed May 29, 2000, 1 Page.
Office Action for Argentina Patent Application No. 20170102053, mailed Nov. 9, 2021, 5 Pages.
Office Action for Australian Application No. 2017300845, mailed on Nov. 2, 2022, 3 pages.
Office Action for Australian Patent Application No. 2018389797, mailed on Sep. 16, 2023,4 Pages.
Office Action for Brazilian Application No. 1120201112417 mailed on Sep. 1, 2022, 5 pages.
Office Action for Brazilian Application No. BR112019000848-9, mailed on Mar. 28, 2024, 10 pages.
Office Action for Canada Application No. 3,028,878, mailed Feb. 18, 2020, 3 pages.
Office Action for Canadian Application No. 3,084,120 mailed on Jan. 25, 2023, 4 pages.
Office Action for Canadian Application No. 3,126,493 mailed on Aug. 23, 2022, 6 pages.
Office Action for Canadian Application No. 3,173,256, mailed on Feb. 14, 2024, 4 pages.
Office Action for Canadian Patent Application No. 3084120, mailed Aug. 26, 2021, 5 Pages.
Office Action for Canadian Patent Application No. 3,084,120 mailed on Jul. 25, 2022, 3 pages.
Office Action for Chinese Application No. 201880082447.4 mailed on Nov. 14, 2022, 16 pages.
Office Action for Chinese Application No. 202210041938.2, mailed on Dec. 1, 2022,13 pages.
Office Action for Chinese Patent Application No. 201880082447.4, mailed Oct. 12, 2021, 20 Pages.
Office Action for Chinese Patent Application No. 201880082447.4 mailed on May 23, 2022, 13 pages.
Office Action for Chinese Patent Application No. 202210041938.2, mailed on Jun. 15, 2023, 12 pages.
Office Action for European Application No. 18842651.4 mailed on Aug. 2, 2022, 5 pages.
Office Action for European Application No. 18842651.4 mailed on Sep. 1, 2023, 5 pages.
Office Action for European Application No. 20711328.3, mailed on Jul. 26, 2023, 5 pages.
Office Action for European Patent Application No. 17742441.3, mailed Mar. 11, 2022, 7 Pages.
Office Action for European Patent Application No. 17742441.3, mailed Nov. 13, 2023, 10 Pages.
Office Action for Japanese Application No. 2020-529210, mailed on Apr. 21, 2023, 7 pages.
Office Action for Japanese Application No. 2020-529210, mailed on Oct. 27, 2022, 7 pages.
Office Action for Japanese Application No. 2023-008736, mailed on Jan. 4, 2024, 11 Pages.
Office Action for Japanese Patent Application No. 2020-055505, mailed Mar. 12, 2020, 9 Pages.
Office Action for Japanese Patent Application No. 2020-055505, mailed Jul. 20, 2023, 5 Pages.
Office Action for Japanese Patent Application No. 2020055505, mailed Feb. 21, 2022, 11 Pages.
Office Action for Japanese Patent Application No. 2020055505, mailed Oct. 28, 2021, 11 Pages.
Office Action for Japanese Patent Application No. 2021-543388, mailed on Mar. 6, 2024, 12 Pages.
Office Action for U.S. Appl. No. 17/194,780, mailed on May 10, 2023, 205 pages.
Office Action for U.S. Appl. No. 17/231,455, mailed on Dec. 13, 2022, 29 pages.
Office Action for U.S. Appl. No. 17/497,381, mailed on Dec. 12, 2022,17 pages.
Office Action for U.S. Appl. No. 17/497,393, mailed on Dec. 21, 2022,14 pages.
Office Action for U.S. Appl. No. 17/497,393, mailed on Nov. 30, 2022, 24 pages.
Office Action for U.S. Appl. No. 17/497,393, mailed on Oct. 20, 2022,18 pages.
Office Action for U.S. Appl. No. 17/530,096, mailed on Mar. 6, 2023, 36 pages.
Office Action for U.S. Appl. No. 17/530,096, mailed on Nov. 22, 2022, 20 pages.
Office Action for U.S Appl. No. 17/666,192, mailed on Apr. 6, 2023, 20 pages.
Office Action for U.S. Appl. No. 17/666,192 mailed on Sep. 6, 2022, 15 pages.
Non-Final Office Action for U.S. Appl. No. 18/643,773 mailed on Jun. 28, 2024, 9 Pages.
Scrima L., et al., "The Effects of γ-Hydroxybutyrate on the Sleep of Narcolepsy Patients: A Double-Blind Study," Sleep, 1990, vol. 13 (6), pp. 479-490.
Second Office Action for Canadian Patent Application No. 3028878, mailed Apr. 1, 2021, 4 Pages.
Second Office Action for Chinese Patent Application No. 201780057633, mailed Jun. 30, 2021, 12 Pages.
Seno M., et al., "The Rheological Behaviour of Suspensions of Ion-exchange Resin Particles," Bulletin of the Chemical Society of Japan, Apr. 1966, vol. 39 (4), pp. 776-778.
Series F., et al., "Effects of Enhancing Slow-Wave Sleep by Gamma-Hydroxybutyrate on Obstructive Sleep Apnea," The American Review of Respiratory Disease, Jun. 1992, vol. 145 (6), pp. 1378-1383.
Shah V.P., et al., "In Vitro Dissolution Profile Comparison—Statistics and Analysis of the Similarity Factor, f2," Pharmaceutical Research, 1998, vol. 15 (6), pp. 889-896.
Singh I., et al., "Ion Exchange Resins: Drug Delivery and Therapeutic Applications," Fabad Journal of Pharmaceutical Sciences, 2007, vol. 32, pp. 91-100.
Snead O.C., et al., "Ontogeny of γ-Hydroxybutyric Acid. I. Regional Concentration in Developing Rat, Monkey and Human Brain," Brain Research, 1981, vol. 227 (4), pp. 579-589.
Snead O.C., "γ-Hydroxybutyrate Model of Generalized Absence Seizures: Further Characterization and Comparison with Other Absence Models," Epilepsia, 1988, vol. 29 (4), pp. 361-368.
Srikanth M.V., et al., "Ion-Exchange Resins as Controlled Drug Delivery Carriers," Journal of Scientific Research, 2010, vol. 2 (3), pp. 597-611.

(56) References Cited

OTHER PUBLICATIONS

Stock G., "Increase in Brain Dopamine After Axotomy or Treatment With Gamma Hydroxybutyric Acid Due to Elimination of the Nerve Impulse Flow," Naunyn-Schmiedeberg's Arch. Pharmacol, 1973, vol. 278 (4), pp. 347-361.
Strand M.C., et al., "Driving Under the Influence of Non-Alcohol Drugs—An Update. Part II: Experimental Studies," Forensic Science Review, 2016, vol. 28 (2), pp. 100-101.
Strong A.J., "y-Hydroxybutyric Acid and Intracranial Pressure," The Lancet, Jun. 9, 1984, vol. 1 (8389), p. 1304.
Suner S., et al., "Pediatric Gamma Hydroxybutyrate Intoxication," Academic Emergency Medicine, 1997, vol. 4 (11), pp. 1041-1045.
Susta M., et al., "Emotion Stimulus Processing in Narcolepsy with Cataplexy," Journal of Sleep Research, 2017, vol. 26, pp. 30-37.
Takahara J., et al., "Stimulatory Effects of Gamma-Hydroxybutyric Acid on Growth Hormone and Prolactin Release in Humans," Journal of Clinical Endocrinology Metabolism, 1977, vol. 44 (5), pp. 1014-1017.
Takka S., et al., "Evaluation of Chitosan/Alginate Beads Using Experimental Design: Formulation and in Vitro Characterization," AAPS Pharm Sci Tech, Mar. 2010, vol. 11 (1), pp. 460-466.
"Taxotere," Physicians Desk Reference, 51st Edition, 1997, pp. 2204-2207.
Thai D., et al., "GHB and Ethanol Effects and Interactions in Humans," Journal of Clinical Psychopharmacology, 2006, vol. 26 (5), pp. 524-529.
Thorpy M., et al., "Reducing the Clinical and Socioeconomic Burden of Narcolepsy by Earlier Diagnosis and Effective Treatment," Sleep Medicine Clinics, 2017, vol. 12 (1), pp. 61-71.
Thorpy M.J., "Recently Approved and Upcoming Treatments for Narcolepsy," CNS Drugs, 2020, vol. 34, pp. 9-27.
Thorpy M.J., "Update on Therapy for Narcolepsy" Current Treatment Options in Neurology, 2015, 17(20), pp. 1-12.
Thorpy M.J., "Update on Therapy for Narcolepsy," Current Treatment Options in Neurology, vol. 17, No. 20, May 2015, pp. 20-32.
Tittarelli R., et al., "Ultra-High-Performance Liquid Chromatography Tandem Mass Spectrometry Determination of GHB, GHB-Glucuronide in Plasma and Cerebrospinal Fluid of Narcoleptic Patients under Sodium Oxybate Treatment," Forensic Science International, 2017, vol. 274, pp. 70-74.
"Transcript of a Markman Hearing," In the Case of *Jazz Pharmaceuticals, Inc.*, Plaintiff, v. *Roxane Laboratories, Inc.*, Defendant (United States District Court for the District of New Jersey, Civil 106108 ES), Apr. 26, 2012, 231 pages.
Tunnicliff G., "Sites of Action of Gamma-Hydroxybutyrate (GHB)—A Neuroactive Drug with Abuse Potential," Clinical Toxicology, 1997, vol. 35 (6), pp. 581-590.
Turnberg L.A., "Abnormalities in Intestinal Electrolyte Transport in Congenital Chloridorrhoea," Gut, 1971, vol. 12 (7), pp. 544-551.
United States Pharmacopeial Convention, Inc.: The National Formulary, 23/NF18, Jan. 1, 1995, p. 2205.
U.S. Department of Health and Human Services., et al., "Dissolution Testing of Immediate Release Solid Oral Dosage Forms," Food and Drug Administration, CDER, Aug. 1997, 18 pages.
U.S. Department of Health and Human Services., et al., "Extended Release Oral Dosage Forms: Development, Evaluation, and Application of In Vitro/In Vivo Correlations," Food and Drug Administration, CDER, Sep. 1997, 28 pages.
U.S. Department of Health and Human Services., "Guidance for Industry, Food- Effect Bioavailability and Fed Bioequivalence Studies," Food and Drug Administration, Center for Drug Evaluation and Research, Dec. 2002, BP, 12 pages.
Van A.G., et al., "Placentatransfer of 4-Hydroxybutyric Acid in Man," Anaesthesiology and Intensive Care Medicine, 1978, vol. 110, pp. 55-64.
Van Ginneken C.A.M., et al., "Linear and Nonlinear Kinetics of Drug Elimination. I. Kinetics on the Basis of a Single Capacity-Limited Pathway of Elimination with or Without Simultaneous Supply-Limited Elimination," Journal of Pharmacokinetics and Biopharmaceutics, 1974, vol. 2 (5), pp. 395-415.

Mckers M.D., "Gammahydroxybutyric Acid," International Anesthesiology Clinics, 1969, vol. 7 (1), pp. 75-89.
Vogel., et al., "Toxicologic/transport properties of NCS-382, a y-hydroxybutyratc (GHB) receptor ligand, in neuronal and epithelial cells: Therapeutic implications for SSADH deficiency, a GABA metabolic disorder," Toxicol in Vitro, 2018, vol. 46, pp. 203-212.
Wade A., et al., "Malic Acid," The Handbook of Pharmaceutical Excipients, Second Edition, 1994, pp. 285-286, 633.
Walden M., et al., "The Effect of Ethanol on the Release of Opioids 30 from Oral Sustained-Release Preparations," Drug Development and Industrial Pharmacy, 2007, vol. 33 (10), pp. 1101-1111.
Wang Q., et al., "Characterization of Monocarboxylate Transport in Human Kidney HK-2 Cells," Molecular Pharmaceutics, 2006, vol. 3 (6), pp. 675-685.
Wang Q., et al., "Flavonoids Modulate Monocarboxylate Transporter-1-Mediated Transport of y-Hydroxybutyrate In Vitro and In Vivo," Drug Metabolism and Disposition, 2007, vol. 35 (2), pp. 201-208.
Wang Q., et al., "Monocarboxylate Transporter (MOT) Mediates the Transport of y-Hydroxybutyrate in Human Kidney HK-2 cells," Pharmaceutical Research, 2007, vol. 24 (6), pp. 1067-1078.
Wang Q., et al., "Pharmacokinetic Interaction between the Flavonoid Luteolin and y-Hydroxybutyrate in Rats: Potential Involvement of Monocarboxylate Transporters," The American Association of Pharmaceutical Scientists, 2008, vol. 10 (1), pp. 47-55.
Wang Q., et al., "The Role of Monocarboxylate Transporter 2 and 4 in the Transport of y-Hydroxybutyric Acid in Mammalian Cells," Drug Metabolism and Disposition, 2007, vol. 35 (8), pp. 1393-1399.
Wang Q., et al., "Transport of y-Hydroxybutyrate in Rat Kidney Membrane Vesicles: Role of Monocarboxylate Transporters," Journal of Pharmacology and Experimental Therapeutics, 2006, vol. 318 (2), pp. 751-761.
World Health Organization, "Annex 7: Multisource (Generic) Pharmaceutical Products: Guidelines on Registration Requirements to Establish Interchangeability," WHO Expert Committee on Specifications for Pharmaceutical Preparations, Fortieth Report, Retrieved from URL: http://apps.who.int/prequal/infogeneral/documents/TRS937/WHOTRS937_eng.pdf#page=359, 2006, pp. 347-390.
World Health Organization (WHO), "Guidelines on Packaging for Pharmaceutical Products," WHO Technical Report Series, Annexure 9, 2002, pp. 119-156.
XYREM: "Mean Oxybate Plasma Concentration in Healthy Volunteers," retrieved from URL: https://www.xyremhcp.com/xyrem-pharmacokinetics-adults, downloaded in Jul. 2021, 10 Pages.
Xyrem (Sodium Oxybate)., "Highlights of Prescribing Information and Full Prescribing Information," Jazz Pharmaceuticals Inc, Apr. 2015, 31 pages.
Yamada Y., et al., "Effect of Butyrolactone and Gamma-Hydroxybutyrate on the EEG and Sleep Cycle in Man," Electroencephalography and Clinical Neurophysiology, 1967, vol. 22 (6), pp. 558-562.
Zheng J., "Formulation and Analytical Development for Low-Dose Oral Drug Products," John Wiley Sons Inc, Hoboken, New Jersey, Table 4.1, 2009, 28 pages.
Non-Final Office Action for U.S. Appl. No. 18/539,960 mailed on Jun. 7, 2024, 28 Pages.
Kollb-Sielecka M., et al., "The European Medicines Agency Review of Pitolisant for Treatment of Narcolepsy: Summary of the Scientific Assessment by the Committee for Medicinal Products for Human Use," Sleep Medicine, 2017, vol. 33, pp. 125-129.
Kornum B.R., et al., "Narcolepsy," Nature Reviews/Disease Primers, Feb. 9, 2017, vol. 3, pp. 1-19.
Kothare S.V., et al., "Pharmacotherapy of Narcolepsy: Focus on Sodium Oxybate," Clinical Medicine Insights: Therapeutics, 2010, vol. 2, pp. 37-52.
Kovalska P., et al., "Higher Body Mass Index in Narcolepsy with Cataplexy: Lifelong Experience", Sleep Medicine, 2017, vol. 32, 1 page.
Kovalska P., et al., "Narcolepsy with Cataplexy in Patients Aged Over 60 years: A Case-Control Study," Sleep Medicine, 2016, vol. 26, pp. 79-84.
Krahn L.E., "Understanding the Needs of Older Patients with Narcolepsy," Sleep Medicine, 2016, vol. 26, 3 pages.

(56) References Cited

OTHER PUBLICATIONS

Kristoffersen L., et al., "Determination of Safety Margins for Whole Blood Concentrations of Alcohol and Nineteen Drugs in Driving Under the Influence Cases," Forensic Science International, 2016, vol. 259, pp. 119-126.

Laborit H., "Gamma-Hydroxybutyrate, Succinic Semialdehyde and Sleep," Laboratoire d'Eutonologie, 1973, pp. 257-274.

Ladinsky H., et al., "Mode of Action of Gamma-Butyrolactone on the Central Cholinergic System," Naunyn-Schmiedeberg's, Arch Pharmacol, 1983, vol. 322 (1), pp. 42-48.

Lam W.K., et al., "Monocarboxylate Transporter-Mediated Transport of y-Hydroxybutyric Acid in Human Intestinal Caco-2 Cells," Drug Metabolism and Disposition, 2010, vol. 38 (3), pp. 441-447.

Lammers G.J., et al., "Gamma-Hydroxybutyrate and Narcolepsy: A Double-Blind Placebo-Controlled Study," Sleep, 1993, vol. 16 (3), pp. 216-220.

Lapierre, et al., "The Effect of Gamma-Hydroxybutyrate: A Double-Blind Study of Normal Subjects," Sleep Research, 1988, vol. 17 (99), 6 pages.

Lapierre O., et al., "The Effect of Gamma-Hydroxybutyrate on Nocturnal and Diurnal Sleep of Normal Subjects: Further Considerations on REM Sleep-Triggering Mechanisms," Sleep, 1990, vol. 13 (1), pp. 24-30.

Lecendreux M., et al., "Narcolepsy Type 1 Is Associated with a Systemic Increase and Activation of Regulatory T Cells and with a Systemic Activation of Global T Cells," PLoS ONE, Jan. 20, 2017, pp. 1-14.

Lee C.R., "Evidence for the Beta-Oxidation of Orally Administered 4-Hydroxybutyrate in Humans," Biochemical Medicine, 1977, vol. 17 (3), pp. 284-291.

Lernmark A., "Environmental Factors in the Etiology of Type 1 Diabetes, Eliac Disease and Narcolepsy," Pediatric Diabetes, Jul. 2016, vol. 17 (22), pp. 65-72.

Lettieri J., et al., "Improved Pharmacological Activity via Pro-Drug Modification: Comparative Pharmacokinetics of Sodium Gamma-hydroxybutyrate and Gamma-butyrolactone," Research Communications in Chemical Pathology and Pharmacology, Oct. 1, 1978, vol. 22 (1), pp. 107-118.

Leu-Semenescu., et al., "Benefits and risk of sodium oxybate in idiopathic hypersomnia versus narcolepsy type 1: a chart review," Sleep Medicine, Jan. 2016, vol. 17, pp. 38-44.

Liakoni E., et al., "Presentations to an Urban Emergency Department in Switzerland Due to Acute Y-hydroxybutyrate Toxicity," Scandinavian Journal of Trauma, Resuscitation and Emergency Medicine, 2016, vol. 24 (107), pp. 1-9.

Liechti M.E., et al., "Pharmacokinetics and Pharmacodynamics of y-Hydroxybutyrate in Healthy Subjects," British Journal of Clinical Pharmacology, 2016, vol. 81, pp. 980-988.

Lin R.Y., et al., "Human Monocarboxylate Transporter 2 (MCT2) Is a High Affinity Pyruvate Transporter," The Journal of Biological Chemistry, Oct. 30, 1998, vol. 273 (44), pp. 28959-28965.

Lingford-Hughes A., et al., "Improving GHB Withdrawal with Baclofen: Study Protocol for a Feasibility Study for a Randomized Controlled Trial," Trials, 2016, vol. 17, pp. 1-11.

Linselle M., et al., "Can Drugs Induce or Aggravate Sleep Apneas? A Case Non Case Study in Vigibase the WHO Pharmacovigilance Database," Fundamental Clinical Pharmacology, 2017, vol. 31 (3), pp. 359-366.

Lubrano E., et al., "Fibromyalgia in Patients with Irritable Bowel Syndrome. An Association with the Severity of the Intestinal Disorder," International Journal of Colorectal Disease, 2001, vol. 16 (4), pp. 211-215.

Luhn O., "Using Excipients In Powder Formulations," Pharmaceutical Technology Europe, Retrieved from URL: https://www.pharmtech.com/view/using-excipients-powder-formulations, Jan. 7, 2011, vol. 23 (1), 2 pages.

Lusina M., et al., "Stability Study of Losartan/hydrochlorothiazide Tablets," International Journal of Pharmaceutics, 2005, vol. 291 (1-2), pp. 127-137.

Mahore J.G., et al., "Ion Exchange Resins: Pharmaceutical Applications and Recent Advancement," International Journal of Pharmaceutical Sciences Review and Research, Mar.-Apr. 2010, vol. 1 (2), pp. 8-13.

Maitre M., et al., "Mechanisms for the Specific Properties of y-Hydroxybutyrate in Brain," Medicinal Research Reviews, 2016, vol. 36, pp. 1-25.

Mamelak M., et al., "A Pilot Study on the Effects of Sodium Oxybate on Sleep Architecture and Daytime Alertness in Narcolepsy," Sleep, 2004, vol. 27 (7), pp. 1327-1334.

Mamelak M., et al., "Sleep-Inducing Effects of Gammahydroxybutyrate," The Lancet, Aug. 11, 1973, vol. 302 (7824), pp. 328-329.

Mamelak M., et al., "The Effects of y-Hydroxybutyrate on Sleep," Biological Psychiatry, 1977, vol. 12 (2), pp. 273-288.

Mamelak M., et al., "Treatment of Narcolepsy and Sleep Apnea with Gammahydroxybutyrate: A Clinical and Polysomnographic Case Study," Sleep, 1981, vol. 4 (1), pp. 105-111.

Mamelak M., et al., "Treatment of Narcolepsy with y-Hydroxybutyrate. A Review of Clinical and Sleep Laboratory Findings," Sleep, 1986, vol. 9 (1), pp. 285-289.

Mamelak M., "Gamma-hydroxybutyrate: An Endogenous Regulator of Energy Metabolism," Neuroscience and Biobehavioral Reviews, 1989, vol. 13 (4), pp. 187-198.

Maresova P., et al., "Treatment Cost of Narcolepsy with Cataplexy in Central Europe," Therapeutics and Clinical Risk Management, 2016, vol. 12, pp. 1709-1715.

Markman Opinion, filed Sep. 14, 2012, In the Case of *Jazz Pharmaceuticals, Inc.*, Plaintiff, v. *Roxane Laboratories, Inc.*, Defendant (United States District Court for the District of New Jersey, Civil 10-6108 ES, 43 pages.

Martin John., "Capsule Endoscopy: How Long Does it Take to Pass," Pill Cam, https://www.topdoctors.co.uk/medical-articles/capsule-endoscopy-how-long-does-it-take-to-pass, Oct. 5, 2019, 4 Pages.

Martinez-Orozco F.J., et al., "Comorbidity of Narcolepsy Type 1 With Autoimmune Diseases and Other Immunopathological Disorders: A Case-Control Study," Journal of Clinical Medicine Research, 2016, vol. 8 (7), pp. 495-505.

Maruyama T., et al., The Pathogenesis of Narcolepsy, Current Treatments and Prospective Therapeutic Targets, Expert Opinion on Orphan Drugs, 2016, vol. 4, No. 1, pp. 63-82.

Mason P. E., et al., "Gamma Hydroxybutyric Acid (GHB) Intoxication," Academic Emergency Medicine, 2002, vol. 9 (7), pp. 730-739.

Mazarr-Proo S., et al., "Distribution of GHB in Tissues and Fluids Following a Fatal Overdose," Journal of Analytical Toxicology, 2005, vol. 29 (5), pp. 398-400.

Medicines for Children, "Oral Rehydration Salts," Leaflet information by Neonatal and Paediatric Pharmacists Group (NPPG), Retrieved from URL: https://www.medicinesforchildren.org.uk/oral-rehydration-salts, published Jul. 25, 2013, 3 pages.

Mesmer, et al., "Determination of Gamma-Hydroxybutyrate (GHB) and Gamma-Butyrolactone (GBL) by HPLC/UV-VIS Spectrophotometry and HPLC/Thermospray Mass Spectrometry," Journal of Forensic Sciences, 1998, vol. 43 (3), pp. 489-492.

Moldofsky H., "A Chronobiologic Theory of Fibromyalgia," Journal of Musculoskeletal Pain, 1993, vol. 1 (1), pp. 49-59.

Moldofsky H., et al., "Muskuloskeletal Symptoms and Non-REM Sleep Disturbance in Patients with 'Fibrositis Syndrome' and Healthy Subjects," Psychosomatic Medicine, Jul.-Aug. 1975, vol. 37 (4), pp. 341-351.

Momenzadeh S., et al., "Evaluation of in Vivo Transfection Efficiency of Eudragit Coated Nanoparticles of Chitosan-DNA: A pH-sensitive System Prepared for Oral DNA Delivery," Iran Red Crescent Med J, Apr. 2015, vol. 17, No. 4, DOI: 10.5812/ircmj. 16761, 7 Pages.

Moresco M., et al., "Pharmacogenetics and Treatment Response in Narcolepsy Type 1: Relevance of the Polymorphisms of the Drug Transporter Gene ABCB1," Clinical Neuropharmacology, 2016, vol. 39 (1), pp. 18-23.

(56) References Cited

OTHER PUBLICATIONS

Morgenthaler T.I., "Practice Parameters for the Treatment of Narcolepsy and other Hypersomnias of Central Origin," Sleep, 2007, vol. 30 (12), 16 pages.
Morris M.E., et al., "Overview of the Proton-coupled Mct (SLC16A) Family of Transporters: Characterization, Function and Role in the Transport of the Drug of Abuse Y-Hydroxybutyric Acid," The American Association of Pharmaceutical Scientists, 2008, vol. 10 (2), pp. 311-321.
Morris M.E., et al., "Renal Clearance of y-Hydroxybutyric Acid in Rats: Increasing Renal Elimination as a Detoxification Strategy," Journal of Pharmacology and Experimental Therapeutics, 2005, vol. 313 (3), pp. 1194-1202.
Chen., et al., "Pharmacokinetics, Relative Bioavailability and Food Effect of JZP-258 and Sodium Oxybate: Results of two Phase 1, Open-Label, randomised crossover studies in healthy volunteers," Sleep Medicine, Abstracts, 2019, vol. 64, pp. S65-S66.
Ciolino L.A., et al., "The Chemical Interconversion of GHB and GBL: Forensic Issues and Implications," Journal of Forensic Sciences, 2001, vol. 46 (6), pp. 1315-1323.
Code of Federal Regulations (C.F.R.), Title 21 "Food and Drugs," Part 211 "Current Good Manufacturing Practice for finished Pharmaceuticals," Stability testing, vol. 4, Revised as of Apr. 1, 2019, 3 pages.
Communication Pursuant to Article 94(3) EPC for European Patent Application No. 18842651.4, mailed on Apr. 29, 2024, 5 pages.
Consolo S., et al., "Mediation by the Corticostriatal Input of the In Vivo Increase in Rat Striatal Acetylcholine Content Induced by 2-Chloroadenosine," Biochemical Pharmacology, 1983, vol. 32 (19), pp. 2993-2996.
Cook S.I., et al., "Review Article: Short Chain Fatty Acids in Health and Disease," Alimentary Pharmacology & Therapeutics, 1998, vol. 12, pp. 499-507.
Cremaschi R.C., et al., "Narcolepsy Type 1 and Type 2—A 10-Year Follow-up: Body Mass Index and Comorbidities," Sleep Medicine, 2017, vol. 32, pp. 285-286.
Dauvilliers Y., et al., "Narcolepsy with Cataplexy," The Lancet, 2007, vol. 369, pp. 499-511.
Dauvilliers Y., et al., "Vitamin D Deficiency in Type 1 Narcolepsy: A Reappraisal," Sleep Medicine, 2017, vol. 29, pp. 1-6.
Davis G.R., et al., "Active Chloride Secretion in the Normal Human Jejunum," Journal of Clinical Investigation, Dec. 1980, vol. 66 (6), pp. 1326-1333.
Donjacour C.E.H.M., et al., "Sodium Oxybate Increases Prolactin Secretion in Narcolepsy Patients and Healthy Controls," European Journal of Endocrinology, 2011, vol. 164, pp. 363-370.
Dornbierer D.A., et al., "Nocturnal Gamma-Hydroxybutyrate Reduces Cortisol-Awakening Response and Morning Kynurenine Pathway Metabolites in Healthy Volunteers," International Journal of Neuropsychopharmacology, 2019, vol. 22, No. 10, pp. 631-639.
Drakatos P., et al., "Sleep-Stage Sequencing of Sleep-Onset REM Periods in MSLT Predicts Treatment Response in Patients with Narcolepsy," Journal of Sleep Research, 2016, vol. 25, pp. 203-210.
Dye T.J., et al., "Epidemiology and Pathophysiology of Childhood Narcolepsy," Paediatric Respiratory Reviews, 2018, vol. 25, pp. 14-18.
Erowid, "Gamma-hydroxybutyrnte (GHB) Basic Synthesis Procedure," Retrieved from the internet URL: http://www.erowid.org/chemicals/ghb/ghb_synthesis.shtml (as downloaded on Aug. 8, 2013) 2 pages.
Examination Report No. 1 for Australian Patent Application No. 2023203055, mailed on May 6, 2024, 3 pages.
Examination Report No. 1 for Australian Patent Application No. 2017300845 dated May 17, 2022, 6 Pages.
Extended European Search Report for European Application No. 23156035.0, mailed on Jul. 6, 2023, 12 pages.
Fallingborg J., "Intraluminal pH of the Human Gastrointestinal Tract," Danish Medical Bulletin, Jun. 1999, vol. 46 (3), pp. 183-196, PMID: 10421978, Retrieved from the Internet: URL: https://pubmed.ncbi.nlm.nih.gov/10421978/.
FDA Guideline, Revised Guidance for Industry on Bioavailability and Bioequivalence Studies for Orally Administered Drug Products—General Considerations; Availability, Federal Register, Mar. 19, 2003, vol. 68 (53), 1 page.
FDA: "Impurities in New Drug Products," Guidance for Industry Q3B(R2), Aug. 2006, Revision 3, 18 pages, Retrieved from the Internet: https://www.fda.gov/media/71733/download.
Felmlee M.A., et al., "Concentration-Effect Relationships for the Drug of Abuse y-Hydroxybutyric Acid," The Journal of Pharmacology and Experimental Therapeutics, 2010, vol. 333 (3), pp. 764-771.
Felmlee M.A., et al., "Mechanistic Toxicokinetic Model for y-Hydroxybutyric Acid: Inhibition of Active Renal Reabsorption as a Potential Therapeutic Strategy," The American Association of Pharmaceutical Scientists, 2010, vol. 12 (3), pp. 407-416.
Ferrara S.D., et al., "Pharmacokinetics of y-Hydroxybutyric Acid in Alcohol Dependent Patients After Single and Repeated Oral Doses," British Journal of Clinical Pharmacology, 1992, vol. 34, pp. 231-235.
Ferrara S.D., et al., "Therapeutic Gamma-Hydroxybutyric Acid Monitoring in Plasma and Urine by Gas Chromatographymass Spectrometry," Journal of Pharmaceutical & Biomedical Analysis, 1993, vol. 11 (6), pp. 483-487.
Ferris T.J., et al., "Synthesis, Characterisation and Detection of Gamma-Hydroxybutyrate Salts," Forensic Science International, 2012, vol. 216, pp. 158-162.
Fides, "Solutions of 4-hydroxybutyric acid salts for injection," Chem Abstract ES302338. Laboratorio M. Cuatecases, S.A., 2011. 1 page.
Final Office Action for U.S. Appl. No. 16/223,940, mailed Sep. 10, 2020, 22 pages.
Final Office Action for U.S. Appl. No. 16/281,235, mailed Apr. 15, 2020, 6 pages.
Final Office Action for U.S. Appl. No. 16/419,516, mailed Feb. 24, 2021, 13 pages.
Final Office Action for U.S. Appl. No. 16/419,616, mailed Aug. 19, 2020, 13 pages.
Final Office Action for U.S. Appl. No. 16/419,616, mailed Nov. 24, 2020, 10 pages.
Final Office Action for U.S. Appl. No. 16/420,321, mailed Nov. 24, 2020, 11 pages.
Final Office Action for U.S. Appl. No. 16/431,219, mailed Feb. 24, 2021, 11 pages.
Final Office Action for U.S. Appl. No. 16/984,645, mailed Mar. 4, 2022, 51 pages.
Final Office Action for U.S. Appl. No. 17/322,299, mailed Oct. 25, 2021, 28 pages.
Final Office Action for U.S. Appl. No. 17/484,916 mailed Feb. 15, 2022, 47 Pages.
Final Office Action for U.S. Appl. No. 17/497,381 mailed Aug. 10, 2022, 15 Pages.
Final Office Action for U.S. Appl. No. 17/666,205 mailed Jun. 29, 2022, 15 Pages.
Final Office Action for U.S. Appl. No. 17/837,740 mailed on May 2, 2024, 6 Pages.
Final Office Action for U.S. Appl. No. 18/368,403 mailed on May 2, 2024, 15 Pages.
Final Office Action for U.S. Appl. No. 18/388,699 mailed on May 2, 2024, 26 Pages.
Final Office Action for U.S. Appl. No. 16/987,515, mailed Apr. 21, 2021, 78 pages.
First Office Action and Search Report for Chinese Patent Application No. 202080016490.8, dated Jun. 5, 2024, 10 pages.
First Office Action and Search Report for Chinese Patent Application No. 202180027893.7, dated Apr. 3, 2024, 14 pages.
First Office Action for Brazilian Patent Application No. 112019000848.9, mailed Jun. 29, 2021, 5 Pages.
First Office Action for Chinese Patent Application No. 201780057633, mailed Oct. 21, 2020, 14 Pages.
First Office Action for European Patent Application No. 18842651.4, mailed May 18, 2021, 5 Pages.
Flamel: "Flamel's Drug Delivery Platforms," publication date: Jun. 2015, pp. 1-43.

(56) References Cited

OTHER PUBLICATIONS

Flores N.M., et al., "The Humanistic and Economic Burden of Narcolepsy," Journal of Clinical Sleep Medicine, 2016, vol. 12 (3), pp. 401-407.
Food and Drug Administration (FDA), U.S. Department of Health and Human Services, Center for Drug Evaluation and Research (CDER), Center for Biologics Evaluation and Research (CBER), "Guidance for Industry Container Closure Systems for Packaging Human Drugs and Biologics, Chemistry, Manufacturing, And Controls Documentation," May 1999, 56 pages.
"Food and Drug Administration, HHS," 21 C.F.R., Part 184, 1998, pp. 441-535.
Franco P., et al., "High Bicarbonate Levels in Narcoleptic Children," Journal of Sleep Research, 2016, vol. 25, pp. 194-202.
Frucht S.J., et al., "A Pilot Tolerability and Efficacy Trial of Sodium Oxybate in Ethanol-Responsive Movement Disorders," Movement Disorders, 2005, vol. 20 (10), pp. 1330-1337.
Frucht S.J., et al., "A Single-Blind, Open-Label Trial of Sodium Oxybate for Myoclonus and Essential Tremor," Neurology, 2005, vol. 65 (12), pp. 1967-1970.
Fuller D.E., et al., "The Xyrem Risk Management Program," Drug Safety, 2004, vol. 27 (5), pp. 293-306.
Fung H., et al., "Pharmacokinetics of 1,4-Butanediol in Rats: Bioactivation to y-Hydroxybutyric Acid, Interaction with Ethanol, and Oral Bioavailability," The American Association of Pharmaceutical Scientists, 2008, vol. 10 (1), pp. 56-69.
Gadroen K., et al., "Patterns of Spontaneous Reports on Narcolepsy following Administration of Pandemic Influenza Vaccine; A Case Series of Individual Case Safety Reports in Eudravigilance," Vaccine, 2016, vol. 34, pp. 4892-4897.
Gallimberti L., et al., "Clinical Efficacy of Gamma-Hydroxybutyric Acid in Treatment of Opiate Withdrawal," Eur Arch Psychiatry Clin Neurosci, 1994, vol. 244 (3), pp. 113-114.
Gallimberti L., et al., "Gamma-Hydroxybutyric Acid for Treatment of Opiate Withdrawal Syndrome," Neuropsychopharmacology, 1993, vol. 9 (1), pp. 77-81.
Gallimberti L., "Gamma-hydroxybutyric Acid for Treatment of Alcohol Withdrawal Syndrome," The Lancet, Sep. 30, 1989, vol. 2 (8666), pp. 787-789.
Gallimberti L., "Gamma-Hydroxybutyric Acid in the Treatment of Alcohol Dependence: A Double Blind Study," Alcoholism: Clinical and Experimental Research, Jul./Aug. 1992, vol. 16 (4), pp. 673-676.
Gennaro A.R., "Oral Solid Dosage Forms," 20th Edition, Chapter 45, The Science and Practice of Pharmacy, 2000, pp. 858-893.
Gennaro A.R., "Remington: The Science and Practice of Pharmacy," 20th Edition, 2000, pp. 860-863.
George C.F.P., et al., "A 2-week, Polysomnographic, Safety Study of Sodium Oxybate in Obstructive Sleep Apnea Syndrome," Sleep Breath, 2011, vol. 15, pp. 13-20.
Gerra G., et al., "Flumazenil Effects on Growth Hormone Response to Gamma-Hydroxybutyric Acid," International Clinical Psychopharmacology, 1994, vol. 9, pp. 211-215.
Gessa G.L., et al., "Gamma-Hydroxybutyric acid (GHB) for Treatment of Ethanol Dependence," European Neuropsychopharmacology, 1993, vol. 3 (3), pp. 224-225.
Gessa G.L., et al., "Gamma-Hydroxybutyric Acid in the Treatment of Alcohol Dependence," Clinical Neuropharmacology, 1992, vol. 15, Suppl. 1, Pt. A, pp. 303A-304A.
Gill R.K., et al., "Expression and Membrane Localization of MCT Isoforms along the Length of the Human Intestine," American Journal of Physiology-Cell Physiology, 2005, vol. 289, pp. C846-C852.
Goyanes A., et al., "Gastrointestinal Release Behaviour of Modified-Release Drug Products: Dynamic Dissolution Testing of Mesalazine Formulations," International Journal of Pharmaceutics, 2015, vol. 484, No. 1-2, pp. 103-108, Retrieved from the Internet: URL: https://discovery.ucl.ac.uk/id/eprint/1462647/3/Basit. 1462647_5-ASA. pdf.
Grenier V., et al., "Enzymatic Assay for GHB Determination in Forensic Matrices," Journal of Analytical Toxicology, 2012, vol. 36, pp. 523-528.
Grove-White I.G., et al., "Critical Flicker Frequency after Small Doses of Methohexitone, Diazepam and Sodium 4-Hydroxybutyrate," British Journal of Anaesthesia, Feb. 1971, vol. 43 (2), pp. 110-112.
Grove-White I.G., et al., "Effect of Methohexitone, Diazepam and Sodium 4-Hydroxybutyrate on Short-Term Memory," British Journal of Anaesthesia, Feb. 1971, vol. 43 (2), pp. 113-116.
Guiraud J., et al., "Treating Alcohol Dependence with an Abuse and Misuse Deterrent Formulation of Sodium Oxybate: Results of a Randomised, Double-Blind, Placebo-Controlled Study," European Neuropsychopharmacology, vol. 52, Retrieved from Internet URL: www.elsevier.com/locate/euroneuro, accepted on Jun. 7, 2021, pp. 18-30.
Haller C., et al., "GHB Urine Concentrations After Single-Dose Administrationin Humans," Journal of Analytical Toxicology, 2006, vol. 30, pp. 360-364.
Haque T., et al., "Model Dependent and Independent Approaches to Compare in Vito Release Profiles From Ethylcellulose and Eudragit L100 Based Matrix Tablets," Dhaka University Journal of Pharmaceutical Sciences, 2009, vol. 8 (1), pp. 89-98.
Hasenbos M.A.W.M., et al., "Anaesthesia for Bullectomy, A Technique With Spontaneous Ventilation and Extradural Blockade," Anaesthesia, 1985, vol. 40 (10), pp. 977-980.
Heide A.V.D., et al., "Core Body and Skin Temperature in Type 1 Narcolepsy in Daily Life; Effects of Sodium Oxybate and Prediction of Sleep Attacks," Sleep, 2016, vol. 39 (11), pp. 1941-1949.
Helrich M., et al., "Correlation of Blood Levels of 4-Hydroxybutyrate with State of Consciousness," Anesthesiology, 1964, vol. 25 (6), pp. 771-775.
Hennessy S.A., et al., "The Reactivity of Gamma-Hydroxybutyric acid (GHB) and Gamma-Butyrolactone (GBL) in Alcoholic Solutions," Journal of Forensic Sciences, 2004, vol. 49 (6), pp. 1-10.
"Hib-Imune," Physicians Desk Reference, 41st Edition, 1987, pp. 1095-1096.
"HibVAX," Physicians Desk Reference, 41st Edition, 1987, p. 870.
Hoes M.J.A.J.M., et al., "Gamma-Hydroxybutyric Acid (*) as Hypnotic, Clinical and Pharmacokinetic Evaluation of Gamma Hydroxybutyric Acid as Hypnotic in Man," L'Encephale: Revue de psychiatry clinique biologique et therapeutique, 1980, vol. 6 (1), pp. 93-99.
International Preliminary Report on Patentability for International Application No. PCT/EP2017/068552, mailed Jan. 31, 2019, 9 pages.
International Search Report and Written Opinion for International Application No. PCT/B2018/060278, mailed Apr. 15, 2019, 8 pages.
International Search Report and Written Opinion for International Application No. PCT/EP2017/068552, mailed Sep. 15, 2017, 10 pages.
International Search Report and Written Opinion for International Application No. PCT/IB2020/051726, mailed May 18, 2020, 13 pages.
Jazz Pharmaceuticals, Inc., "Xyrem (Sodium Oxybate) Oral Solution, CIII," Highlights of Prescribing Information, Revised, Sep. 2020, 35 pages.
Jazz Pharmaceuticals, Inc., "Xyrem® (sodium oxybate) oral solution Prescribing Information," XYREM® US Package Insert available at http://pp.jazzpliamia.com/pi/xyem.en.USPI.pdf (downloaded Sep. 12, 2017, 32 pages.
Jazz Pharmaceuticals, Inc., "Xywav (Calcium, Magnesium, Potassium, and Sodium Oxybates) Oral Solution, CIII," Highlights of Prescribing Information, Aug. 2021, 40 pages.
Jazz Pharmaceuticals., "Jazz Pharmaceuticals Announces Positive Top-line Results from Phase 3 Study of JZP-258 in Adult Narcolepsy Patients with Cataplexy and Excessive Daytime Sleepiness," Retrieved from URL: https://investor.jazzpharma.com/node/16206/pdf, Mar. 26, 2019, 2 pages.
Jefferies, Flamel Technologies SA publication, https://www.jefferies.com/CMSFiles/Jefferies.com/files/Flamel.pdf, May 1, 2015, 1 Page.

(56) References Cited

OTHER PUBLICATIONS

Jennum P., et al., "Morbidity of Childhood Onset Narcolepsy: A Controlled National Study," Sleep Medicine, 2017, vol. 29, pp. 13-17.

Jha M.K., "Modified Release Formulations to Achieve the Quality Target Product Profile (QTPP)," IJPSR, 2012, vol. 3, No. 8, pp. 2376-2386.

Johnson M.W., et al., "Comparative Abuse Liability of GHB and Ethanol in Humans, " Experimental and Clinical Psychopharmacology, 2013, vol. 21 (2), pp. 112-123.

Jones A.W., et al., "Concentration-Time Profiles of Gamma-Hydroxybutyrate in Blood After Recreational Doses are Best Described by Zero-Order Rather Than First-Order Kinetics," Journal of Analytical Toxicology, 2009, vol. 33, pp. 332-335.

Kallweit U., et al., "Pharmacological Management of Narcolepsy with and without Cataplexy," Expert Opinionon Pharmacotherapy, 2017, vol. 18 (8) pp. 809-817.

Keating G.M., "Sodium Oxybate: A Review of Its Use in Alcohol Withdrawal Syndrome and in the Maintenance of Abstinence in Alcohol Dependence," Clinical Drug Investigation, 2014, vol. 34, pp. 63-80.

Khatami R., et al., "The European Narcolepsy Network (EU-NN) database," Journal of Sleep Research, 2016, vol. 25, pp. 356-364.

Khediri F., et al., "Efficacy of Diosmectite (Smecta) in the Treatment of Acute Watery Diarrhea in Adults: A Multicenter, Randomized, Double-Blind, Placebo-Controlled, Parallel Group Study," Hindawi Publishing Corporation, Gastroenterology Research and Practice, 2011, vol. 2011, Article ID 783196, 9 pages.

A Double-Blind, Placebo-Controlled Study Demonstrates Sodium Oxybate is Effective for the Treatment of Excessive Daytime Sleepiness in Narcolepsy, Xyrem International Study Group, Journal of Clinical Sleep Medicine, 2005, vol. 1 (4), pp. 391-397.

Abad V.C., et al., "New Developments in the Management of Narcolepsy," Nature and Science of Sleep, 2017, vol. 9, pp. 39-57.

Abanades S., et al., "Relative Abuse Liability of y-Hydroxybutyric Acid, Flunitrazepam, and Ethanol in Club Drug Users," Journal of Clinical Psychopharmacology, 2007, vol. 27 (6), pp. 625-638.

Abanades S., et al., "y-Hydroxybutyrate (GHB) in Humans, Pharmacodynamics and Pharmacokinetics," Annals New York Academy of Sciences, 2006, vol. 1074, pp. 559-576.

"Activase," Physicians Desk Reference, 50th Edition, 1996, pp. 312, 1058-1061.

Ahmed S.M., et al., "Narcolepsy and Influenza Vaccination-Induced Autoimmunity," Annals of Translational Medicine, 2017, vol. 5 (1), pp. 1-4.

Ahmed S.M., et al., "The Safety of Adjuvanted Vaccines Revisited: Vaccine-Induced Narcolepsy," The Israel Medical Association Journal, 2016, vol. 18, pp. 216-220.

Akala E.O., "Effect of Packaging on Stability of Drugs and Drug Products," Pharmaceutical Manufacturing Handbook: Regulations and Quality, 2008, pp. 641-686.

Akifuddin S.K., et al., "Preparation, Characterization and In-Vitro Evaluation of Microcapsules for Controlled Release of Diltiazem Hydrochloride by Ionotropic Gelation Technique," Journal of Applied Pharmaceutical Science, Apr. 2013, vol. 3 (4), pp. 35-42.

Aldrete J.A., et al., "Does Magnesium Produce Anesthesia Evaluation of Its Effects on the Cardiovascular and Neurologic Systems," Anesthesia and Analgesia, 1968, vol. 47 (4), pp. 428-433.

Alshaikh M.K., et al., "Sodium Oxybate for Narcolepsy with Cataplexy: Systematic Review and Meta-Analysis," Journal of Clinical Sleep Medicine, 2012, vol. 8 (4), pp. 451-458.

"Amberlite IRN78 Resin, Nuclear Grade Strong Base Anion Resin," The Dow Chemical Company, Product Data Sheet, Form No. 177-02230-0311, Rev. 0, 3 pages.

Anand V., et al., "Ion-Exchange Resins: Carrying Drug Delivery Forward," Drug Discovery Today 2001, Sep. 17, 2001, vol. 6 (17), pp. 905-914.

Anonymous., "How Much Protein Is In Your Cup of Milk?", Retrieved from Internet URL: https://milklife.com/articles/nutrition/how-much-protein-your-cup-milk, Retrieved on Aug. 30, 2022, 2 pages.

Anonymous, "Relative Humidity in Production and Process Environments," The Engineering Toolbox, 2003, 3 pages, Retrieved from internet URL: https://www.engineeringtoolbox.com/relative-humidity-production-process-d_511.html.

Arena C., et al., "Absorption of Sodium y-Hydroxybutyrate and Its Prodrug y-Butyrolactone: Relationship between In Vitro Transport and In Vivo Absorption," Journal of Pharmaceutical Sciences, 1980, vol. 69 (3), pp. 356-358.

Baldrick P., "Pharmaceutical Excipient Development: The Need for Preclinical Guidance," Regulatory Toxicology and Pharmacology, Oct. 2000, vol. 32 (2), pp. 210-218.

Barateau L., et al., "Hypersomnolence, Hypersomnia, and Mood Disorders," Current Psychiatry Reports, 2017, vol. 19, pp. 1-11.

Barateau L., et al., "Management of Narcolepsy," Current Treatment Options in Neurology, 2016, vol. 18, pp. 1-13.

Barateau L., et al., "Treatment Options for Narcolepsy," CNS Drugs, 2016, vol. 30, pp. 369-379.

Bayram A.K., et al., "Efficiency of a Combination of Pharmacological Treatment and Nondrug Interventions in Childhood Narcolepsy," Neuropediatrics, 2016, vol. 47 (6), pp. 380-387.

Bedard M.A., et al., "Nocturnal y-Hydroxybutyrate—Effect on Periodic Leg Movements and Sleep Organization of Narcoleptic Patients," Clinical Neuropharmacology, Feb. 1989, vol. 12 (1), pp. 29-36.

Berthier M., et al., "Possible Involvement of a Gamma-Hydroxybutyric Acid Receptor in Startle Disease," Acta Paediatr, 1994, vol. 83, pp. 678-680.

Bhattacharya I., et al., "Feasibility of D-Glucuronate to Enhance y-Hydroxybutyric Acid Metabolism During y-Hydroxybutyric Acid Toxicity: Pharmacokinetic and Pharmacodynamic Studies," Biopharmaceutics Drug Disposition, 2007, vol. 28, pp. 1-11.

Bhattacharya I., et al., "Potential y-Hydroxybutyric acid (GHB) Drug Interactions Through Blood-Brain Barrier Transport Inhibition: A Pharmacokinetic Simulation-Based Evaluation," Journal of Pharmacokinetics and Pharmacodynamics, 2006, vol. 33 (5), pp. 657-681.

Biospace: "Flamel Technologies Announces Positive Results of a Second Clinical Trial with Micropump® Sodium Oxybate," BioSpace, Published on: Dec. 22, 2014, 6 Pages.

Black J., et al., "Medical Comorbidity in Narcolepsy: Findings from the Burden of Narcolepsy Disease (BOND) Study," Sleep Medicine, 2017, vol. 33, pp. 13-18.

Black J., et al., "Sodium Oxybate Improves Excessive Daytime Sleepiness in Narcolepsy," Sleep, Jul. 2006, vol. 29, No. 7, pp. 939-946.

Black J., et al., "The Nightly Use of Sodium Oxybate Is Associated with a Reduction in Noctural Sleep Disruption: A Double-Blind, Placebo-Controlled Study in Patients with Narcolepsy," Journal of Clinical Sleep Medicine, 2010, vol. 6 (6), pp. 596-602.

Black S.W., et al., "Challenges in the Development of Therapeutics for Narcolepsy," Prog NeurobioL, 2017, vol. 152, pp. 89-113.

Bodmeier R., "Tableting of Coated Pellets," European Journal of Pharmaceutics and Biopharmaceutics, 1997, vol. 43 (1), pp. 1-8.

Bogan R., et al., "Evaluation of Quality of Life in Patients With Narcolepsy Treated with Sodium Oxybate: Use of the 36-Item Short-Form Health Survey in a Clinical Trial," Neurology and Therapy, 2016, vol. 5, pp. 203-213.

Borgen L., et al., "Xyrem (sodium oxybate): A Study of Dose Proportionality in Healthy Human Subjects," Journal of Clinical Pharmacology, 2000, vol. 40, p. 1053.

Borgen L.A., et al., "The Influence of Gender and Food on the Pharmacokinetics of Sodium Oxybate Oral Solution in Healthy Subjects," Journal of Clinical Pharmacology, 2003, vol. 43, pp. 59-65.

Borgen L.A., et al., "The Pharmacokinetics of Sodium Oxybate Oral Solution following Acute and Chronic Administration to Narcoleptic Patients," Journal of Clinical Pharmacology, 2004, vol. 44, pp. 253-257.

(56) References Cited

OTHER PUBLICATIONS

Boscolo-Berto R., et al., "Narcolepsy and Effectiveness of Gamma-Hydroxybutyrate (GHB): A Systematic Review and Meta-analysis of Randomized Controlled Trials," Sleep Medicine Reviews, 2012, vol. 16, pp. 431-443.
Bowker M.J., et al., "Preparation of Water-Soluble Compounds Through Salt Formulation," Edited by Wermuth C.G., The Practice of Medicinal Chemistry, Academic Press, Third Edition, Chapter 37, 2008, pp. 749-766.
Brailsford A.D., et al., "Increases in Serum Growth Hormone Concentrations Associated with GHB Administration," Journal of Analytical Toxicology, 2017, vol. 41, pp. 54-59.
Brenneisen R., et al., "Pharmacokinetics and Excretion of Gamma-Hydroxybutyrate (GHB) in Healthy Subjects," Journal of Analytical Toxicology, 2004, vol. 28, pp. 625-630.
Broughton R., et al., "Effects of Nocturnal Gamma-Hydroxybutyrate on Spell/Waking Patterns in Narcolepsy-Cataplexy," The Canadian Journal of Neurological Sciences, Feb. 1980, vol. 7 (1), pp. 23-31.
Broughton R., et al., "Gamma-Hydroxy-Butyrate in the Treatment of Narcolepsy: A Preliminary Report," Narcolepsy, Spectrum Publications, Inc, N.Y., 1976, pp. 659-667.
Broughton R., et al., "The Treatment of Narcolepsy-Cataplexy with Nocturnal Gamma- Hydroxybutyrate," The Canadian Journal of Neurological Sciences, 1979, vol. 6 (1), pp. 1-6.
Caballero F., et al., "Characterization of Alginate Beads Loaded With Ibuprofen Lysine Salt and Optimization of the Preparation Method," International Journal of Pharmaceutics, 2014, vol. 460 (1), pp. 181-188.
Calik M.W., "Update on the Treatment of Narcolepsy: Clinical Efficacy of Pitolisant," Nature and Science of Sleep, 2017, vol. 9, pp. 127-133.
Carlier L., et al., "Gamma-Hydroxybutyrate (GHB), An Unusual Cause of High Anion Gap Metabolic Acidosis," Canadian Journal of Emergency Medicine | Journal Canadien De La Medecine D'urgence, 2018, vol. 20, pp. S2-S5.
Carter L.P., et al., "Behavioural Analyses of GHB: Receptor Mechanisms," Pharmacology & Therapeutics, 2009, vol. 121 (1), pp. 100-114.
Carter L.P., et al., "Cognitive, Psychomotor, and Subjective Effects of Sodium Oxybate and Triazolam in Healthy Volunteers," Psychopharmacology (Berl), 2009, vol. 206 (1), pp. 141-154.
Chang R.K., et al., "Polymethacrylates," Handbook of Pharmaceutical Excipients, 2006, Fifth Edition, Pharmaceutical Press, London, pp. 553-560.
Chem Abstract, ES302338, SciFinder, 1964, 1 page.
Chemical Book, CAS DataBase List, Ethyl cellulose, downloaded in Oct. 2021, 5 Pages, (Year: 2021).
Morrison, Robert T., et al., "Organic Chemistry", Chapter 20: "Functional Derivatives of Carboxylic Acids," 3rd Edition, 1973, pp. 658-700.
Morrison R.T., et al., "Organic Chemistry," 3rd Edition, 1973, pp. 672-677.
Morse B.L., et al., "Effects of Monocarboxylate Transporter Inhibition on the Oral Toxicokinetics/Toxicodynamics of y-Hydroxybutyrate and y-Butyrolactone," The Journal of Pharmacology and Experimental Therapeutics, 2013, vol. 345, pp. 102-110.
Nellore A., et al., "Narcolepsy and Influenza Vaccination—the Inappropriate Awakening of Immunity," Annals of Translational Medicine, 2016, vol. 4 (29), pp. 1-6.
Nema S., et al., "Excipients and Their Use in Injectable Products," PDA Journal of Pharmaceutical Science and Technology, Jul.-Aug. 1997, vol. 51 (4), pp. 166-171.
Neuman A., "GHB's Path to Legitimacy: An Administrative and Legislative History of Xyrem," Harvard Law School, Class of 2005, Food and Drug Law, Winter Term 2004, Professor Peter Barton Hutt, Apr. 2004, pp. 1-39.
Non Final Office Action for U.S. Appl. No. 16/223,940, mailed Apr. 15, 2020, 22 pages.
Non Final Office Action for U.S. Appl. No. 16/804,966, mailed Dec. 10, 2021, 13 pages.
Non Final Office Action for U.S. Appl. No. 17/484,916, mailed Nov. 10, 2021, 34 pages.
Non Final Office Action for U.S. Appl. No. 17/497,366 mailed on Aug. 1, 2022, 33 pages.
Non Final Office Action for U.S. Appl. No. 17/837,740 mailed on Mar. 5, 2024, 8 Pages.
Non Final Office Action for U.S. Appl. No. 18/231,581 mailed on Oct. 4, 2023, 19 Pages.
Non Final Office Action for U.S. Appl. No. 18/368,403, mailed on Jan. 16, 2024, 32 pages.
Non Final Office Action for U.S. Appl. No. 18/388,699, mailed on Jan. 30, 2024, 31 pages.
Non Final Office Action for U.S. Appl. No. 18/537,342 mailed on Feb. 28, 2024, 25 Pages.
Non-Final Office Action for U.S. Appl. No. 17/322,299 dated Mar. 15, 2022, 37 pages.
Non-Final Office Action for U.S. Appl. No. 17/497,366 dated Apr. 27, 2022, 24 pages.
Non-Final Office Action for U.S. Appl. No. 17/497,381 dated Jun. 23, 2022, 13 pages.
Non-Final Office Action for U.S. Appl. No. 17/666,192 dated May 19, 2022, 17 pages.
Non-Final Office Action for U.S. Appl. No. 17/666,205 dated May 13, 2022, 8 pages.
Non-Final Office Action for U.S. Appl. No. 15/655,924, mailed May 3, 2018, 15 pages.
Non-Final Office action for U.S. Appl. No. 16/281,235, mailed Jan. 24, 2020, 13 pages.
Non-Final Office Action for U.S. Appl. No. 16/419,516, mailed Jul. 9, 2020, 11 pages.
Non-Final Office Action for U.S. Appl. No. 16/420,321, mailed Aug. 26, 2020, 21 pages.
Non-Final Office Action for U.S. Appl. No. 16/431,219, mailed Aug. 26, 2020, 14 pages.
Non-Final Office Action for U.S. Appl. No. 16/527,633, mailed Feb. 18, 2021, 21 pages.
Non-Final Office Action for U.S. Appl. No. 16/987,510, mailed Dec. 1, 2020, 11 pages.
Non-Final Office Action for U.S. Appl. No. 16/987,515, mailed Dec. 24, 2020, 19 pages.
Non-Final Office Action for U.S. Appl. No. 17/156,053, mailed Sep. 14, 2023, 27 pages.
Non-Final Office Action for U.S. Appl. No. 17/178,117 mailed on May 22, 2024, 34 Pages.
Non-Final Office Action for U.S. Appl. No. 17/322,299, mailed Jul. 21, 2021, 18 pages.
Non-Final Office Action for U.S. Appl. No. 17/666,192, mailed on Mar. 26, 2024, 22 pages.
Non-Final Office Action for U.S. Appl. No. 17/731,562, mailed Sep. 7, 2023, 7 pages.
Non-Final Office Action for U.S. Appl. No. 17/731,562, mailed Aug. 17, 2023, 7 pages.
Non-Final Office Action for U.S. Appl. No. 18/531,095 mailed on May 8, 2024, 34 pages.
Non-Final Office Action for U.S. Appl. No. 18/537,318 mailed on May 10, 2024, 30 Pages.
Non-Final Office Action for U.S. Appl. No. 18/537,332 mailed on May 29, 2024, 32 Pages.
Non-Final Office Action for U.S. Appl. No. 18/539,946 mailed on Apr. 25, 2024, 22 Pages.
Notice of Allowance and Fee(s) due for U.S. Appl. No. 17/497,366 mailed on Sep. 20, 2022, 10 pages.
Notice of Allowance for Japanese Application No. 2019-503463, mailed Feb. 28, 2020, 6 pages.
Notice of Allowance for U.S. Appl. No. 15/655,924, mailed Feb. 7, 2019, 8 pages.
Notice of Allowance for U.S. Appl. No. 15/655,924, mailed Dec. 11, 2018, 6 pages.
Notice of Allowance for U.S. Appl. No. 15/655,924, mailed Nov. 13, 2018, 11 pages.
Notice of Allowance for U.S. Appl. No. 16/281,235, mailed May 1, 2020, 8 pages.

(56) References Cited

OTHER PUBLICATIONS

Notice of Allowance for U.S. Appl. No. 16/281,235, mailed Jun. 26, 2020, 8 pages.
Notice of Allowance for U.S. Appl. No. 16/419,516, mailed Mar. 10, 2021, 8 pages.
Notice of Allowance for U.S. Appl. No. 16/419,616, mailed Dec. 10, 2020, 8 pages.
Notice of Allowance for U.S. Appl. No. 16/420,321, mailed Dec. 15, 2020, 8 pages.
Caputo F., et al., "Gamma Hydroxybutyric Acid (GHB) for the Treatment of Alcohol Dependence: A Review," International Journal of Environmental Research and Public Health 2009, Jun. 24, 2009, vol. 06, No. 06, pp. 1917-1929.
Co-pending U.S. Appl. No. 17/178,117, inventors Megret; Claire et al., filed on Feb. 17, 2021.
Co-pending U.S. Appl. No. 17/966,538, inventors Dubow; Jordan et al., filed on Oct. 14, 2022.
Dupont, "DuPont™ AmberLite™ IRN78 OH Ion Exchange Resin," Feb. 2023, Form No. 45-D01206-en, Rev. 5, 5 pages.
Lecendreux M., "Pharmacological Management of Narcolepsy and Cataplexy in Pediatric Patients," Pediatr Drugs, Jul. 30, 2014, vol. 16, pp. 363-372.
Non-Final Office Action for U.S. Appl. No. 18/120,231, mailed Sep. 10, 2024, 31 pages.
Non-Final Office Action for U.S. Appl. No. 18/758,081, mailed Sep. 9, 2024, 84 pages.
Thorpy M.J., "Cataplexy Associated with Narcolepsy: Epidemiology, Pathophysiology and Management," CNS Drugs, Jan. 2006, vol. 20, No. 1, pp. 43-50.
Non-Final Office Action for U.S. Appl. No. 18/758,358, mailed Aug. 29, 2024, 14 pages.
Notice of Allowance for U.S. Appl. No. 18/539,960, mailed Aug. 28, 2024, 9 pages.
Notice of Allowance for U.S. Appl. No. 18/643,773, mailed Aug. 28, 2024, 9 pages.
Eller et al., "Sleep Medicine," Dec. 2013, vol. 14, Supplement 1, pp. e302-e303.
Non-Final Office Action for U.S. Appl. No. 18/758,699, mailed on Sep. 17, 2024, 17 pages.
Non-Final Office Action for U.S. Appl. No. 17/502,562, mailed Sep. 29, 2024, 24 pages.
Non-Final Office Action for U.S. Appl. No. 18/759,320, dated Oct. 18, 2024, 18 pages.
Notice of Allowance for U.S. Appl. No. 18/537,332, mailed on Aug. 28, 2024, 9 pages.
Notice of Allowance for U.S. Appl. No. 17/178,117, mailed on Oct. 11, 2024, 9 pages.
Communication Pursuant to Article 94(3) EPC for Application No. 21720848.7, mailed on Sep. 24, 2024, 7 pages.
Office Action for Australian Application No. 20200231916, mailed on Sep. 18, 2024, 4 pages.
Office Action for Canadian Application No. 3,210,888, mailed on Oct. 3, 2024, 6 pages.
Office Action for Japanese Application No. 2023-008736, mailed on Sep. 25, 2024, 4 pages.

\* cited by examiner

GAMMA-HYDROXYBUTYRATE COMPOSITIONS HAVING IMPROVED PHARMACOKINETICS IN THE FED STATE

CROSS-REFERENCE TO RELATED APPLICATIONS

This application is a continuation of U.S. Non-Provisional application Ser. No. 17/837,740, filed Jun. 10, 2022 which is a continuation of U.S. Non-Provisional application Ser. No. 16/804,966, filed Feb. 28, 2020 which claims priority to U.S. Provisional Application No. 62/812,699, filed Mar. 1, 2019 and U.S. Provisional Application No. 62/857,008, filed Jun. 4, 2019.

FIELD

The present invention relates to compositions for the treatment of narcolepsy, cataplexy, or excessive daytime sleepiness comprising gamma-hydroxybutyrate in a unit dose suitable for administration less than two hours after eating. The present invention also relates to modified release formulations of gamma-hydroxybutyrate having improved pharmacokinetic (PK) properties in the fed state, and to therapeutic uses thereof.

BACKGROUND

Narcolepsy is a devastating disabling condition. The cardinal symptoms are excessive daytime sleepiness (EDS), cataplexy (a sudden loss of muscle tone triggered by strong emotions, seen in approximately 60% of patients), hypnogogic hallucination (HH), sleep paralysis (SP), and disturbed nocturnal sleep (DNS). Other than EDS, DNS is the most common symptom seen among narcolepsy patients.

One of the major treatments for narcolepsy is sodium oxybate. The precise mechanism by which sodium oxybate produces an effect is unknown, however sodium oxybate is thought to act by promoting SWS (delta sleep) and consolidating night-time sleep. Sodium oxybate administered before nocturnal sleep increases Stages 3 and 4 sleep and increases sleep latency, while reducing the frequency of sleep onset REM periods (SOREMPs). Other mechanisms, which have yet to be elucidated, may also be involved.

Sodium oxybate is also known as sodium 4-hydroxybutanoate, or gamma-hydroxybutyric acid sodium salt, and has the following chemical structure:

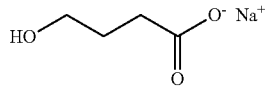

Sodium oxybate is marketed commercially in the United States as Xyrem®. The product is formulated as an immediate release liquid solution that is taken once immediately before bed, and a second time approximately 2.5 to 4 hours later, in equal doses. Sleep-onset may be dramatic and fast, and patients are advised to be sitting in bed when consuming the dose. The most commonly reported side effects are nausea, dizziness, vomiting, somnolence, enuresis and tremor.

One critical drawback of Xyrem® is the requirement to take the first does at least 2 hours after eating. Specifically, Xyrem®'s label expressly advises "[t]ake the first dose of Xyrem® at least 2 hours after eating because food significantly reduces the bioavailability of sodium oxybate." The medical problem cautioned against by the Xyrem® label and unaddressed by the prior art is a deleterious food effect on the absorption of GHB. As noted in the FDA's Xyrem® Risk Management Program, "Because food significantly reduces the bioavailability of sodium oxybate, the patient should try to eat well before (several hours) going to sleep and taking the first dose of sodium oxybate. Patients should try to minimize variability in the timing of dosing in relation to meals." (See https://www.accessdata.fda.gov/drugsatfda_docs/label/2002/21196lbl.pdf). As a practical matter, the food effect obstacle of the prior art creates a variety of unmet problems for the patient because it is not always possible to eat several hours before sleep. Likewise, despite best efforts, a patient may have variability in the timing of dosing in relation to meals due to unforeseen schedule changes, travel, etc. As a result, the food effect problem of the prior art necessarily causes reduced patient compliance, reduced efficacy, and reduced safety. Moreover, since GHB is a known drug of abuse, there is inherently a greater risk of abuse, including accidental abuse, as a result of Xyrem®'s food effect problem.

Scientific studies have shown that after a high-fat meal the intestinal uptake of GHB may be significantly decreased due to the inhibition of anionic transporters, such as the Monocarboxylic Acid Transporters (MCTs). MCTs are transport proteins that determine the absorption, renal clearance, and distribution of GHB throughout the body. Recent studies have shown the MCT-mediated intestinal absorption of GHB to occur in a concentration- and proton gradient-dependent manner and via a carrier-mediated process along the length of the intestine. The MCT-mediated intestinal absorption of GHB is important for its pharmacological activity because more than 99% of GHB is ionized and cannot diffuse across cellular membranes at physiologic pH.

Accordingly, there is a need for compositions of gamma-hydroxybutyrate that can be administered less than two hours after eating without compromising safety or efficacy.

SUMMARY OF THE INVENTION

In an aspect, the present disclosure encompasses an oral pharmaceutical composition for the treatment of narcolepsy, cataplexy, or excessive daytime sleepiness that may be administered less than two hours after eating. For example, a composition including gamma-hydroxybutyrate may be in a unit dose suitable for administration less than two hours after eating. In additional aspects, the composition may me suitable for once-daily administration. In some aspects, the composition provides a mean $AUC_{inf}$ and/or mean $C_{max}$ when administered less than two hour after eating that is 50%-120% of the mean $AUC_{inf}$ or mean $C_{max}$ when the composition is administered at least two hours after eating. When administered less than two hours after eating, the composition may provide an $AUC_{inf}$ and/or a $C_{max}$ bioequivalent to an $AUC_{inf}$ or $C_{max}$ of an equal dose of immediate release liquid solution of sodium oxybate administered at to and tan in equally divided doses at least two hours after eating. In some aspects, a 6 g dose of the composition administered less than two hours after eating has been shown to achieve a mean $AUC_{inf}$ of greater than 240 hr*μ/mL, and a mean $C_{max}$ that is from 50% to 140% of the mean $C_{max}$ provided by an equal dose of immediate release liquid solution of sodium oxybate administered at to and $t_{4h}$ in equally divided doses at least two hours after eating.

Further provided herein is a method of treating narcolepsy and associated disorders and symptoms in a patient in need thereof by administering an oral pharmaceutical composition of gamma-hydroxybutyrate less than two hours after eating. In an aspect, the composition may be administered once-daily. In some aspects, the composition may be administered in the morning or the evening after eating. In other aspects, sleep is includes for at least six consecutive hours.

In additional aspects, a method of treating narcolepsy and associated disorders and symptoms in a patient in need thereof may include administering an oral pharmaceutical composition comprising gamma-hydroxybutyrate once daily, where the composition is dose proportional. The $C_{max}$ of the composition may be dose proportional across one or more of 4.5 g, 7.5 g, and 9 g doses of the composition.

Also provided herein are oral pharmaceutical compositions and methods thereof for the treatment of narcolepsy, cataplexy, or excessive daytime sleepiness comprising gamma-hydroxybutyrate in a unit dose suitable for administration once daily, where most adverse events (AEs) occur during the Tmax period (around $C_{max}$). In another aspect, compositions and methods are provided for the treatment of narcolepsy, cataplexy, or excessive daytime sleepiness comprising gamma-hydroxybutyrate in a unit dose suitable for administration once daily, wherein most adverse events (AEs) occur close to $T_{max}$, during the $C_{max}$ period. In some embodiments of this aspect, administration of the oral pharmaceutical composition less than two hours after eating may result in fewer AEs than administration of the oral pharmaceutical composition at least two hours after eating. The oral pharmaceutical composition of some embodiments may have a more favorable safety profile (i.e., fewer AEs) as compared to an equal dose of immediate release liquid solution of sodium oxybate administered at $t_0$ and $t_{4h}$ in equally divided doses.

Other aspects and iterations of the invention are described more thoroughly below.

DESCRIPTION OF THE FIGURES

The accompanying drawings, which are incorporated in and constitute a part of this specification, illustrate several embodiments of the invention and together with the description serve to explain the principles of the invention.

DETAILED DESCRIPTION

Figure 1A:
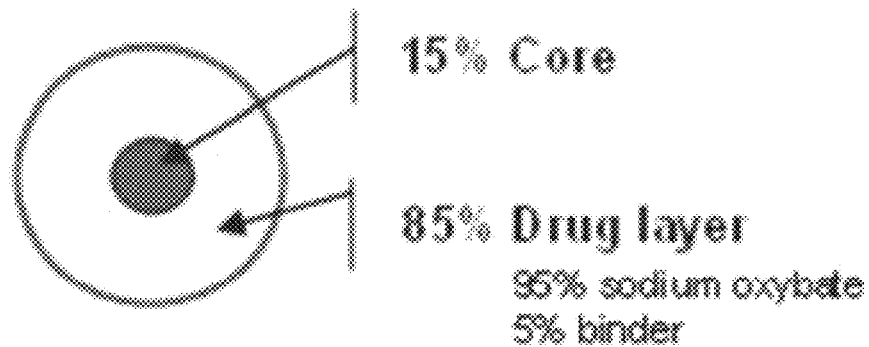
FIG. 1A depicts the qualitative and quantitative structure of the immediate release (IR) microparticles of gamma-hydroxybutyrate of Example 1.

The present invention may be understood more readily by reference to the following detailed description of embodiments of the formulation, methods of treatment using some embodiments of the formulation, and the Examples included therein.

Definitions and Use of Terms

Wherever an analysis or test is required to understand a given property or characteristic recited herein, it will be understood that the analysis or test is performed in accordance with applicable guidances, draft guidances, regulations and monographs of the United States Food and Drug Administration ("FDA") and United States Pharmacopoeia ("USP") applicable to drug products in the United States in force as of Nov. 1, 2015 unless otherwise specified. Clinical endpoints may be judged with reference to standards adopted by the American Academy of Sleep Medicine, including standards published at C Iber, S Ancoli-Israel, A Chesson, SF Quan. The AASM Manual for the Scoring of Sleep and Associated Events. Westchester, IL: American Academy of Sleep Medicine; 2007.

When a pharmacokinetic comparison is made between a formulation described or claimed herein and a reference product, it will be understood that the comparison is performed in a suitable designed cross-over trial, although it will also be understood that a cross-over trial is not required unless specifically stated. It will also be understood that the comparison may be made either directly or indirectly. For example, even if a formulation has not been tested directly against a reference formulation, it can still satisfy a comparison to the reference formulation if it has been tested against a different formulation, and the comparison with the reference formulation may be deduced therefrom.

As used in this specification and in the claims which follow, the singular forms "a," "an" and "the" include plural referents unless the context dictates otherwise. Thus, for example, reference to "an ingredient" includes mixtures of ingredients, reference to "an active pharmaceutical agent" includes more than one active pharmaceutical agent, and the like.

"Bioavailability" means the rate and extent to which the active ingredient or active moiety is absorbed from a drug product and becomes available at the site of action.

"Relative bioavailability" or "Rel BA" or "RBA" means the percentage of mean $AUC_{inf}$ of the tested product relative to the mean $AUC_{inf}$ of the reference product for an equal total dose. Unless otherwise specified, relative bioavailability refers to the percentage of the mean $AUC_{inf}$ observed for a full dose of the test product relative to the mean $AUC_{inf}$ observed for two ½-doses of an immediate release liquid solution administered four hours apart for an equal total dose.

"Bioequivalence" means the absence of a significant difference in the rate and extent to which the active ingredient or active moiety in pharmaceutical equivalents or pharmaceutical alternatives become available at the site of drug action when administered at the same molar dose under similar conditions in an appropriately designed study.

When ranges are given by specifying the lower end of a range separately from the upper end of the range, it will be understood that the range may be defined by selectively combining any one of the lower end variables with any one of the upper end variables that is mathematically and physically possible. Thus, for example, if a formulation may contain from 1 to 10 weight parts of a particular ingredient, or 2 to 8 parts of a particular ingredient, it will be understood that the formulation may also contain from 2 to 10 parts of the ingredient. In like manner, if a formulation may contain greater than 1 or 2 weight parts of an ingredient and up to 10 or 9 weight parts of the ingredient, it will be understood that the formulation may contain 1-10 weight parts of the ingredient, 2-9 weight parts of the ingredient, etc. unless otherwise specified, the boundaries of the range (lower and upper ends of the range) are included in the claimed range.

In like manner, when various sub-embodiments of a senior (i.e. principal) embodiment are described herein, it will be understood that the sub-embodiments for the senior embodiment may be combined to define another sub-embodiment. Thus, for example, when a principal embodiment includes sub-embodiments 1, 2 and 3, it will be understood that the principal embodiment may be further limited by any one of sub-embodiments 1, 2 and 3, or any combination of sub-embodiments 1, 2 and 3 that is mathematically and physically possible. In like manner, it will be understood that the principal embodiments described herein may be combined in any manner that is mathematically and physically possible, and that the invention extends to such combinations.

When used herein the term "about" or "substantially" or "approximately" will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength, as described in FDA's March 2003 Guidance for Industry on BIOAVAILABILITY AND BIOEQUIVALENCE STUDIES FOR ORALLY ADMINISTERED DRUG PRODUCTS-GENERAL CONSIDERATIONS.

When used herein the term "gamma-hydroxybutyrate" or GHB, unless otherwise specified, refers to the free base of gamma hydroxy-butyrate, a pharmaceutically acceptable salt of gamma-hydroxybutyric acid, and combinations thereof, their hydrates, solvates, complexes or tautomers forms. Gamma-hydroxybutyric acid salts may be selected from the sodium salt of gamma-hydroxybutyric acid or sodium oxybate, the potassium salt of gamma-hydroxybutyric acid, the magnesium salt of gamma-hydroxybutyric acid, the calcium salt of gamma-hydroxybutyric acid, the lithium salt of gamma-hydroxybutyric, the tetra ammonium salt of gamma-hydroxybutyric acid or any other pharmaceutically acceptable salt forms of gamma-hydroxybutyric acid.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. The term "formulation" or "composition" refers to the quantitative and qualitative characteristics of a drug product or dosage form prepared in accordance with the current invention.

As used herein the doses and strengths of gamma-hydroxybutyrate are expressed in equivalent-gram (g) weights of sodium oxybate unless stated expressly to the contrary. Thus, when considering a dose of gamma-hydroxybutyrate other than the sodium salt of gamma-hydroxybutyrate, one must convert the recited dose or strength from sodium oxybate to the gamma-hydroxybutyrate under evaluation. Thus, if an embodiment is said to provide a 4.5 g dose of gamma-hydroxybutyrate, because the form of gamma-hydroxybutyrate is not specified, it will be understood that the dose encompasses a 4.5 g dose of sodium oxybate, a 5.1 g dose of potassium gamma-hydroxybutyrate (assuming a 126.09 g/mol MW for sodium oxybate and a 142.20 g/mol MW for potassium gamma-hydroxybutyrate), and a 3.7 g dose of the free base (assuming a 126.09 g/mol MW for sodium oxybate and a 104.1 g/mol MW for the free base of gamma-hydroxybutyrate), or by the weight of any mixture of salts of gamma-hydroxybutyric acid that provides the same amount of GHB as 4.5 g of sodium oxybate.

As used herein "microparticle" means any discreet particle of solid material. The particle may be made of a single material or have a complex structure with core and shells and be made of several materials. The terms "microparticle", "particle", "microspheres" or "pellet" are interchangeable and have the same meaning. Unless otherwise specified, the microparticle has no particular particle size or diameter and is not limited to particles with volume mean diameter D(4,3) below 1 mm.

As used herein, the "volume mean diameter D(4,3)" is calculated according to the following formula:

$$D(4, 3) = \Sigma(d4i \cdot ni)/\Sigma(d3\ i \cdot ni)$$

wherein the diameter d of a given particle is the diameter of a hard sphere having the same volume as the volume of that particle.

As used herein, the terms "composition", "oral composition", "oral pharmaceutical composition", "finished composition", "finished formulation" or "formulation" are interchangeable and designate the composition of gamma-hydroxybutyrate comprising modified release microparticles of gamma-hydroxybutyrate, immediate release microparticles of gamma-hydroxybutyrate, and any other excipients. The composition may be described as extended release, delayed release, or modified release.

As used herein, "immediate release" means release of the major part of gamma-hydroxybutyrate over a relatively short period, e.g. at least 75% of the AP is released in 0.75 h, for example, in 30 min.

As used herein, an "immediate release (IR) portion" of a formulation includes physically discreet portions of a formulation, mechanistically discreet portions of a formulation, and pharmacokinetically discreet portions of a formulation that lend to or support a defined IR pharmacokinetic characteristic. Thus, for example, any formulation that releases active ingredient at the rate and extent required of the immediate release portion of the formulations of the present invention includes an "immediate release portion," even if the immediate release portion is physically integrated in what might otherwise be considered an extended release formulation. Thus, the IR portion may be structurally discreet or structurally indiscreet from (i.e. integrated with) the MR portion. In an embodiment, the IR portion and MR portion are provided as particles, and in other embodiments the IR portion and MR portion are provided as particles discreet from each other.

As used here in, "immediate release formulation" or "immediate release portion" refers to a composition that releases at least 80% of its gamma-hydroxybutyrate in 1 hour when tested in a dissolution apparatus 2 according to USP 38 <711> in a 0.1N HCl dissolution medium at a temperature of 37° C. and a paddle speed of 75 rpm.

As used herein, "dose dumping" is understood as meaning an immediate and unwanted release of the dose after oral ingestion. In an embodiment, dose dumping may be rapid release of gamma-hydroxybutyrate in the presence of alcohol.

In like manner, a "modified-release (MR) portion" includes that portion of a formulation or dosage form that lends to or supports a particular MR pharmacokinetic characteristic, regardless of the physical formulation in which the MR portion is integrated. The modified release drug delivery systems are designed to deliver drugs at a specific time or over a period of time after administration, or at a specific location in the body. The USP defines a modified release system as one in which the time course or location of drug release or both, are chosen to accomplish objectives of therapeutic effectiveness or convenience not fulfilled by conventional IR dosage forms. More specifically, MR solid oral dosage forms include extended release (ER) and delayed-release (DR) products. A DR product is one that releases a drug all at once at a time other than promptly after administration. Typically, coatings (e.g., enteric coatings) are used to delay the release of the drug substance until the dosage form has passed through the acidic medium of the stomach. An ER product is formulated to make the drug available over an extended period after ingestion, thus allowing a reduction in dosing frequency compared to a drug presented as a conventional dosage form, e.g. a solution or an immediate release dosage form. For oral applications, the term "extended-release" is usually interchangeable with "sustained-release", "prolonged-release" or "controlled-release".

Traditionally, extended-release systems provided constant drug release to maintain a steady concentration of drug. For some drugs, however, zero-order delivery may not be optimal and more complex and sophisticated systems have been developed to provide multi-phase delivery. One may distinguish among four categories of oral MR delivery systems: (1) delayed-release using enteric coatings, (2) site-specific or timed release (e.g. for colonic delivery), (3) extended-release (e.g., zero-order, first-order, biphasic release, etc.), and (4), programmed release (e.g., pulsatile, delayed extended release, etc.) See Modified Oral Drug Delivery Systems at page 34 in Gibaldi's DRUG DELIVERY SYSTEMS IN PHARMACEUTICAL CARE, AMERICAN SOCIETY OF HEALTH-SYSTEM PHARMACISTS, 2007 and Rational Design of Oral Modified-release Drug Delivery Systems at page 469 in DEVELOPING SOLID ORAL DOSAGE FORMS: PHARMACEUTICAL THEORY AND PRACTICE, Academic Press, Elsevier, 2009. As used herein, "modified release formulation" or "modified release portion" in one embodiment refers to a composition that releases its gamma-hydroxybutyrate according a multiphase delivery that is comprised in the fourth class of MR products, e.g. delayed extended release. As such it differs from the delayed release products that are classified in the first class of MR products.

As used herein the terms "coating", "coating layer," "coating film," "film coating" and like terms are interchangeable and have the same meaning. The terms refer to the coating applied to a particle comprising the gamma-hydroxybutyrate that controls the modified release of the gamma-hydroxybutyrate.

As used herein, "meal state" or "meal mode" includes the fed state, 2 hours post meal, and the fasted mode. A "fed state" or "fed mode" includes the period of time immediately after consumption of a meal up to two hours post meal. The fed state may include the period less than two hours after eating. A "fasted state" or "fasted mode" includes the period of time after 8 hours post meal consumption. "2 hours post meal" includes the period of time between the fed state and the fasted state. For example, "2 hours post meal" may include the period between at least 2 hours and 8 hours post meal. In all pharmacokinetic testing described herein, unless otherwise stated, the dosage form, or the initial dosage form if the dosing regimen calls for more than one administration, is administered less than two hours after eating, approximately two hours after eating, or more than 8 hours after eating. For example, the dosage form may be administered less than two hours after consumption of a standardized dinner, approximately two hours after consumption of a standardized dinner, or more than 8 hours after consumption of a standardized dinner. The standardized dinner may consist of 25.5% fat, 19.6% protein, and 54.9% carbohydrates.

A "similar PK profile", a "substantially similar PK profile", or "comparable bioavailability" means that the mean $AUC_{inf}$ of a test product is from 80% to 125% of the mean $AUC_{inf}$ of a reference product in a suitably designed cross-over trial, the mean plasma concentration at 8 hours ($C_{8h}$) of the test product is from 40% to 130% of the mean plasma concentration at 8 hours ($C_{8h}$) of the reference product, and/or that the maximum plasma concentration ($C_{max}$) of the test product is from 50% to 140% of the $C_{max}$ of the reference product.

As used herein, "dose proportional" occurs when increases in the administered dose are accompanied by proportional increases in the PK profile, such as the AUC or $C_{max}$.

A "fed state PK profile" means the mean $AUC_{inf}$, the mean plasma concentration at 8 hours ($C_{8h}$), and/or the maximum plasma concentration ($C_{max}$) of the composition when administered less than two hours after eating.

A "2 hour post meal administration PK profile" means the mean $AUC_{inf}$, the mean plasma concentration at 8 hours ($C_{8h}$), and/or the maximum plasma concentration ($C_{max}$) of the composition when administered at least two hours after eating.

Type 1 Narcolepsy (NT1) refers to narcolepsy characterized by excessive daytime sleepiness ("EDS") and cataplexy. Type 2 Narcolepsy (NT2) refers to narcolepsy characterized by excessive daytime sleepiness without cataplexy.

A diagnosis of narcolepsy (with or without cataplexy) may be confirmed by one or a combination of (i) an overnight polysomnogram (PSG) and a Multiple Sleep Latency Test (MSLT) performed within the last 2 years, (ii) a full documentary evidence confirming diagnosis from the PSG and MSLT from a sleep laboratory must be made available, (iii) current symptoms of narcolepsy including: current complaint of EDS for the last 3 months (ESS greater than 10), (iv) mean MWT less than 8 minutes, (v) mean number of cataplexy events of 8 per week on baseline Sleep/Cataplexy Diary, and/or (vi) presence of cataplexy for the last 3 months and 28 events per week during screening period.

As used herein, "adverse events" (AEs) or "treatment emergent adverse events" (TEAEs) means self-reported adverse events by a patient administered a composition for which the AEs are related. AEs or TEAEs may include but not limited to gastrointestinal disorders, nervous system disorders, somnolence, dizziness, nausea, headache, feeling drunk, vomiting, and/or fatigue.

Unless otherwise specified herein, percentages, ratios and numeric values recited herein are based on weight; averages and means are arithmetic means; all pharmacokinetic measurements based on the measurement of bodily fluids are based on plasma concentrations.

It will be understood, when defining a composition by its pharmacokinetic or dissolution properties herein, that the formulation can in the alternative be defined as "means for" achieving the recited pharmacokinetic or dissolution properties. Thus, a formulation in which the modified release portion releases less than 20% of its gamma-hydroxybutyrate at one hour can instead be defined as a formulation comprising "means for" or "modified release means for" releasing less than 20% of its gamma-hydroxybutyrate at one hour. It will be further understood that the structures for achieving the recited pharmacokinetic or dissolution properties are the structures described in the examples hereof that accomplish the recited pharmacokinetic or dissolution properties.

Oral Pharmaceutical Composition for Administration Less than Two Hours After Eating As the prior art demonstrates, it is extremely difficult to find a formulation that may be administered less than 2 hours after eating a meal and that has pharmacokinetic properties comparable to an immediate release liquid solution of sodium oxybate administered twice nightly taken at least 2 hours after eating.

The inventors have discovered a novel relationship between in vivo gamma-hydroxybutyrate absorption of modified release particles and the effect of food on the absorption of gamma-hydroxybutyrate which permits, for the first time, a composition of gamma-hydroxybutyrate that may be administered less than 2 hours after eating that approximates the bioavailability of a twice-nightly equipotent immediate release liquid solution of sodium oxybate administered at least 2 hours after eating, and that does so across a range of therapeutic doses.

Provided herein is an oral pharmaceutical composition for the treatment of narcolepsy, cataplexy, or excessive daytime sleepiness that includes gamma-hydroxybutyrate in a unit dose suitable for administration less than two hours after eating. In various embodiments, the composition may include gamma-hydroxybutyrate in an extended release formulation, delayed release formulation, or modified release formulation.

Surprisingly, the composition may be administered at any time after eating without being significantly impacted by a food effect. In an embodiment, the composition may be administered less than two hours after eating. For example, the composition may be administered concurrently with food or may be administered immediately after eating, at least 15 minutes after eating, at least 30 minutes after eating, at least 1 hour after eating, at least 1.5 hours after eating, or less than 2 hours after eating.

The composition may provide a substantially similar fed state PK profile and 2 hour post meal administration PK profile. For example, the $AUC_{inf}$ for the composition administered less than two hours after eating may be substantially similar to the $AUC_{inf}$ when the same composition is administered at least two hours after eating. In another example, the $C_{max}$ for the composition administered less than two hours after eating may be substantially similar to the $C_{max}$ when the same composition is administered at least two hours after eating.

In an embodiment, when the composition is administered less than two hours after eating, it may achieve a mean $AUC_{inf}$ that is bioequivalent to the mean $AUC_{inf}$ provided by an equal dose of the composition administered at least two hours after eating. In some embodiments, when the composition is administered less than two hours after eating, it may achieve a mean $AUC_{inf}$ that is from 50% to 120%, from 60% to 120%, from 70% to 120%, from 75% to 100%, from 80% to 100%, from 80 to 100%, from 90% to 100%, from 50% to 95%, or from 60% to 90% of the mean $AUC_{inf}$ provided by an equal dose of the composition administered at least two hours after eating.

In an embodiment, when the composition is administered less than two hours after eating, it may achieve a mean $C_{max}$ that is bioequivalent to the mean $C_{max}$ provided by an equal dose of the composition administered at least two hours after eating. In some embodiments, when the composition is administered less than two hours after eating, it may achieve a mean $C_{max}$ that is from 50% to 140%, from 60% to 120%, from 70% to 120%, from 75% to 100%, from 80% to 100%, from 80 to 100%, from 90% to 100%, from 50% to 95%, or from 60% to 90% of the mean $C_{max}$ provided by an equal dose of the composition administered at least two hours after eating.

The composition may provide a substantially similar fed state PK profile and fasted state PK profile. In an example, the $AUC_{inf}$ for the composition administered less than two hours after eating may be substantially similar to the $AUC_{inf}$ when the same composition is administered in the fasted state. In yet another example, the $C_{max}$ for the composition administered less than two hours after eating may be substantially similar to the $C_{max}$ when the same composition is administered in the fasted state.

In an embodiment, when the composition is administered less than two hours after eating, it may achieve a mean $AUC_{inf}$ that is bioequivalent to the mean $AUC_{inf}$ provided by an equal dose of the composition administered in the fasted state. In some embodiments, when the composition is administered less than two hours after eating, it may achieve a mean $AUC_{inf}$ that is from 50% to 120%, from 60% to 120%, from 70% to 120%, from 75% to 100%, from 80% to 100%, from 80 to 100%, from 90% to 100%, from 50% to 95%, or from 60% to 90% of the mean $AUC_{inf}$ provided by an equal dose of the composition administered in the fasted state. In an embodiment, when administered less than two hours after eating, it may achieve a mean $AUC_{inf}$ with a 90% CI that fall within the 80-125% bioequivalence range of an equal dose of the composition administered in the fasted state with no effect boundaries. In some examples, the composition provides a mean $AUC_{inf}$ when administered less than two hour after eating that is 80%-95% of the mean $AUC_{inf}$ when the composition is administered while fasting. In additional examples, the composition provides a mean $AUC_{inf}$ when administered less than two hour after eating that is 85%-90% of the mean $AUC_{inf}$ when the composition is administered while fasting. In at least one example, a ratio of the $AUC_{last}$ (fed) to $AUC_{last}$ (fasted) may be about 86 with a 90% CI of 79.9-92.6. In at least one example, a ratio of the $AUC_{inf}$ (fed) to $AUC_{inf}$ (fasted) may be about 86.1 with a 90% CI of 80.0-92.7.

In an embodiment, when the composition is administered less than two hours after eating, it may achieve a mean $C_{max}$ that is bioequivalent to the mean $C_{max}$ provided by an equal dose of the composition administered in the fasted state. In some embodiments, when the composition is administered less than two hours after eating, it may achieve a mean $C_{max}$ that is from 50% to 140%, from 60% to 120%, from 70% to 120%, from 75% to 100%, from 80% to 100%, from 80 to 100%, from 90% to 100%, from 50% to 95%, or from 60% to 90% of the mean $C_{max}$ provided by an equal dose of the composition administered in the fasted state. In an embodiment, when the composition is administered less than two hours after eating, it may achieve a mean $C_{max}$ with a 90% CI that fall within the 80-125% bioequivalence range of an equal dose of the composition administered in the fasted state with no effect boundaries. In some examples, the composition provides a mean $C_{max}$ when administered less than two hours after eating that is 55%-80% of the mean $C_{max}$ when the composition is administered while fasting. In additional examples, the composition provides a mean $C_{max}$ when administered less than two hours after eating that is 60%-75% of the mean $C_{max}$ when the composition is administered while fasting. In at least one example, a ratio of the $C_{max}$ (fed) to $C_{max}$ (fasted) may be about 66.6 with a 90% CI of 58.2-76.5.

In an embodiment, the composition provides a $C_{max}$ that is dose proportional. In additional embodiments, the composition provides no dose dumping.

In an embodiment, compositions of gamma-hydroxybutyrate administered less than two hours after eating may optimize the bioavailability of the gamma-hydroxybutyrate, and roughly approximate the bioavailability of an equal dose of an immediate release liquid solution of sodium oxybate administered twice nightly where the first dose is administered at least two hours after eating.

In some embodiments, the compositions of gamma-hydroxybutyrate administered less than two hours after eating may roughly approximate or exceed the bioavailability of an equal dose of an immediate release solution of sodium oxybate administered twice nightly at least two hours after eating, across the entire therapeutic range of sodium oxybate doses.

In other embodiments, the compositions of gamma-hydroxybutyrate administered less than two hours after eating may produce very little residual drug content in the bloodstream of most patients up to 8 hours after administration but may still be similar to the one observed after administration of an equal dose of an immediate release liquid solution of sodium oxybate administered twice nightly at least two hours after eating.

In an embodiment, there is no significant reduction in safety or efficacy to a patient following administration of the composition. In another embodiment, the compositions of gamma-hydroxybutyrate may improve the therapeutic effectiveness and safety profile of gamma-hydroxybutyrate when administered less than two hours after eating based on novel pharmacokinetic profiles. For example, administration of the gamma-hydroxybutyrate composition less than two hours after eating may result in fewer AEs than administration of the gamma-hydroxybutyrate composition at least two hours after eating or in the fasted state.

In some embodiments, the gamma-hydroxybutyrate composition has a more favorable safety profile as compared to an equal dose of immediate release liquid solution of sodium oxybate administered at $t_0$ and $t_{4h}$ in equally divided doses. Most adverse events (AEs) may occur close to $T_{max}$, during the $C_{max}$ period. In an example, the gamma-hydroxybutyrate composition may have only one $T_{max}$ and one $C_{max}$ per day due to the once daily administration as compared to multiple $T_{max}$ and $C_{max}$ in an immediate release formulation (such as Xyrem®) requiring multiple administrations per day. Therefore, having only one $T_{max}$ and one $C_{max}$ by administration of the gamma-hydroxybutyrate composition may result in fewer AEs than administration of the immediate release formulation. In an additional example, the $C_{max}$ of the gamma-hydroxybutyrate composition may be between the $C_{max}$ of the first peak and the $C_{max}$ Of the second peak of Xyrem®. The gamma-hydroxybutyrate composition may have a lower $C_{max}$ than the $C_{max}$ of an equal dose of an immediate release formulation, such that administration of the gamma-hydroxybutyrate composition may result in fewer AEs than administration of the immediate release formulation. Therefore, administration of the gamma-hydroxybutyrate composition once daily may result in fewer AEs than administration of an equal dose of immediate release liquid solution of sodium oxybate administered at $t_0$ and $t_{4h}$ in equally divided doses. In other embodiments, the onset of efficacy of the composition may be earlier than Xyrem® in the fed state.

The gamma-hydroxybutyrate composition may offer a substantial improvement in safety profile to narcolepsy, cataplexy, or excessive daytime sleepiness patients by reducing the amount of adverse events (AEs) over an 8 hour, 12 hour, 16 hour, 20 hour, 24 hour, and/or 48 hour time period following administration of the gamma-hydroxybutyrate composition, as compared to an immediate release sodium oxybate (e.g., Xyrem®) formulation. In particular, the gamma-hydroxybutyrate composition may result in fewer adverse events and fewer $C_{max}$ periods over an 8 hour, 12 hour, 16 hour, 20 hour, 24 hour, and 48 hour time period, as compared to an immediate release sodium oxybate (e.g., Xyrem®) formulation. Since it appears AEs may be closely related to $C_{max}$, by virtue of the gamma-hydroxybutyrate composition having fewer $C_{max}$ periods than Xyrem®, the gamma-hydroxybutyrate composition may also have fewer AEs over an 8 hour, 12 hour, 16 hour, 20 hour, 24 hour, and/or 48 hour time period, as compared to an immediate release sodium oxybate (e.g., Xyrem®) formulation. Thus, the gamma-hydroxybutyrate composition may have a superior safety profile and/or reduced AEs compared to the prior art (e.g., Xyrem®) or any sodium oxybate composition requiring administration more frequently than once-daily.

In yet another embodiment, the compositions of gamma-hydroxybutyrate administered less than two hours after eating may yield a similar pharmacokinetic profile compared to an immediate release liquid solution of sodium oxybate administered twice nightly at least two hours after eating while potentially giving a reduced dose.

In another embodiment, the compositions of gamma-hydroxybutyrate may allow administration less than two hours after eating compared to the commercial treatment Xyrem®.

In other embodiments, the compositions of gamma-hydroxybutyrate may be administered less than two hours after eating, or may be administered in the fed or fasted state, with improved dissolution and pharmacokinetic profiles compared to an immediate release liquid solution of sodium oxybate administered twice nightly at least two hours after eating.

In an embodiment, the composition provides an $AUC_{inf}$ bioequivalent to an $AUC_{inf}$ of Xyrem® as depicted in FIG. 4A, 5A, 5B, 6A, 6B, 7A, or 7B. In another embodiment, the composition provides a $C_{max}$ that is less than the second $C_{max}$ Of Xyrem® as depicted in FIG. 4A, 5A, 5B, 6A, 6B, 7A, or 7B. In one embodiment, the $C_{max}$ of the composition when administered less than two hours after eating may be between the first and second $C_{max}$ of Xyrem®. In yet another embodiment, the composition provides a $C_{max}$ that is substantially less than the $C_{max}$ of Xyrem® as depicted in FIG. 4A, 5A, 5B, 6A, 6B, 7A, or 7B. The composition may provide a $C_{max}$ that is 10-60% less than the $C_{max}$ of Xyrem® as depicted in FIG. 4A, 5A, 5B, 6A, 6B, 7A, or 7B. The composition may provide a change in $C_{max}$ between when the composition is administered at least two hours after eating and when the composition is administered less than two hours after eating that is 10-60% less than the change in $C_{max}$ of Xyrem as depicted in a figure selected from the group consisting of FIGS. 4A, 5A, 5B, 6A, 6B, 7A, and 7B. The composition may provide an AUC that is more dose proportional than the AUC of Xyrem® as depicted in FIG. 4A, 5A, 5B, 6A, 6B, 7A, or 7B.

In particular, a 6 g dose of a composition of gamma-hydroxybutyrate administered less than two hours after eating has been shown to achieve a mean $AUC_{inf}$ of greater than 230 hr*μg/mL, and a mean $C_{max}$ that is from 50% to 140% of the mean $C_{max}$ provided by an equal dose of immediate release liquid solution of sodium oxybate administered at $t_0$ and $t_{4h}$ in equally divided doses, where the first dose is administered at least two hours after eating a standardized meal. For example, a 6 g dose of the composition administered less than two hours after eating may have a mean $AUC_{inf}$ of about 242 hr*μg/mL and a mean $C_{max}$ of about 64 μg/mL. In addition, a 9 g dose of a composition of gamma-hydroxybutyrate administered less than two hours after eating may achieve a mean $AUC_{inf}$ of greater than 400 hr*μg/mL, and a mean $C_{max}$ that may be from 50% to 140% of the mean $C_{max}$ provided by an equal dose of immediate release liquid solution of sodium oxybate administered at $t_0$ and $t_{4h}$ in equally divided doses where the first does is administered at least two hours after a standardized meal. This may be seen by comparing the release profiles and pharmacokinetic profiles in Examples 1-7.

The compositions of gamma-hydroxybutyrate may have both immediate release and modified release portions. The release of gamma-hydroxybutyrate from the immediate release portion is practically uninhibited, and occurs almost immediately in 0.1N hydrochloric acid dissolution medium. In contrast, while the modified release portion also may release its gamma-hydroxybutyrate almost immediately when fully triggered, the release is not triggered until a predetermined lag-time or the drug is subjected to a suitable dissolution medium such as a phosphate buffer pH 6.8 dissolution medium. Without wishing to be bound by any theory, it is believed that food may have no or low impact on the modified release portion of the composition, as the gamma-hydroxybutyrate from the modified release portion is absorbed in the latter part of the gastro-intestinal tract.

Formulations that achieve this improved bioavailability in the fed state may be described using several different pharmacokinetic parameters. An embodiment of the composition of gamma-hydroxybutyrate includes immediate release and modified release portions, where a 6 g dose of the formulation, when administered less than two hours after eating, may achieve a mean $AUC_{inf}$ of greater than 230, 240, 245, 300, 325, 340, 375, 400, 425, or 450 hr*microgram/mL. In an embodiment, a 6 g does of the composition has a mean $AUC_{inf}$ of greater than 230 hr*microgram/mL. In an embodiment, a 6 g does of the composition has a mean $AUC_{inf}$ of about 242 hr*microgram/mL. For example, when the composition is administered less than two hours after eating, it achieves a mean $AUC_{inf}$ that is from 50% to 120%, from 60% to 120%, from 70% to 120%, from 75% to 100%, from 80% to 100%, from 80 to 100%, from 90% to 100%, from 50% to 95%, or from 60% to 90% of the mean $AUC_{inf}$ provided by an equal dose of the composition administered at least two hours after eating.

An embodiment of the composition of gamma-hydroxybutyrate includes immediate release and modified release portions, where a 6 g dose of the formulation, when administered less than two hours after eating, may achieve a mean $C_{max}$ of greater than 55, 60, 65, or 70 μg/mL. For example, a 6 g dose of the composition has a mean $C_{max}$ of about 64 μg/mL. An embodiment of the composition of gamma-hydroxybutyrate includes immediate release and modified release portions, where a 6 g dose of the formulation, when administered less than two hours after eating, may achieve a mean $C_{max}$ that is from 50% to 140%, from 60% to 140%, from 70% to 140%, from 75% to 135%, from 80% to 135%, from 80 to 130%, from 90% to 110%, from 50% to 95%, or from 60% to 90% of the mean $C_{max}$ provided by an equal dose of an immediate release liquid solution of sodium oxybate (e.g. Xyrem®) administered at $t_0$ and $t_{4h}$ in equally divided doses approximately two hours after a standardized meal. In one embodiment, a 6 g dose of the composition has a mean $C_{max}$ from 60% to 90%, or from 60% to 140% of the mean $C_{max}$ provided by an equal dose of an immediate release liquid solution of sodium oxybate (e.g. Xyrem®) administered at to and $t_{4h}$ in equally divided doses approximately two hours after a standardized meal. In other embodiments, the mean $C_{max}$ is from 100% to 150% of the of the mean $C_{max}$ of a first peak of the equal dose of immediate release liquid solution of sodium oxybate administered at $t_0$ and $t_{4h}$ in equally divided doses at least two hours after eating and the mean $C_{max}$ is from 80% to 100% of the of the mean $C_{max}$ of a second peak of the equal dose of immediate release liquid solution of sodium oxybate administered at $t_0$ and $t_{4h}$ in equally divided doses at least two hours after eating.

An embodiment of the composition of gamma-hydroxybutyrate includes immediate release and modified release portions, where a 9 g dose of the formulation, when administered less than two hours after eating, may achieve a mean $AUC_{inf}$ of greater than 350, 400, 450, 500, 525, or 550 hr*microgram/mL. In one embodiment, a 9 g dose of the composition may have a mean $AUC_{inf}$ of greater than 400 hr*microgram/mL.

An embodiment of the composition of gamma-hydroxybutyrate includes immediate release and modified release portions, where a 9 g dose of the formulation, when administered less than 2 hours after eating, may have a mean $C_{max}$ that is from 50% to 140%, from 60% to 140%, from 70% to 140%, from 75% to 135%, from 80% to 135%, from 80 to 130%, from 90% to 110%, from 50% to 95%, or from 60% to 90% of the mean $C_{max}$ provided by an equal dose of an immediate release liquid solution of sodium oxybate (e.g. Xyrem®) administered at to and tan in equally divided doses approximately two hours after a standardized meal. In one embodiment, a 9 g dose of the composition may have a mean $C_{max}$ from 60% to 90% or 60% to 120% of the mean $C_{max}$ provided by an equal dose of an immediate release liquid solution of sodium oxybate (e.g. Xyrem®) administered at $t_0$ and $t_{4h}$ in equally divided doses approximately two hours after a standardized meal.

Figure 2A:
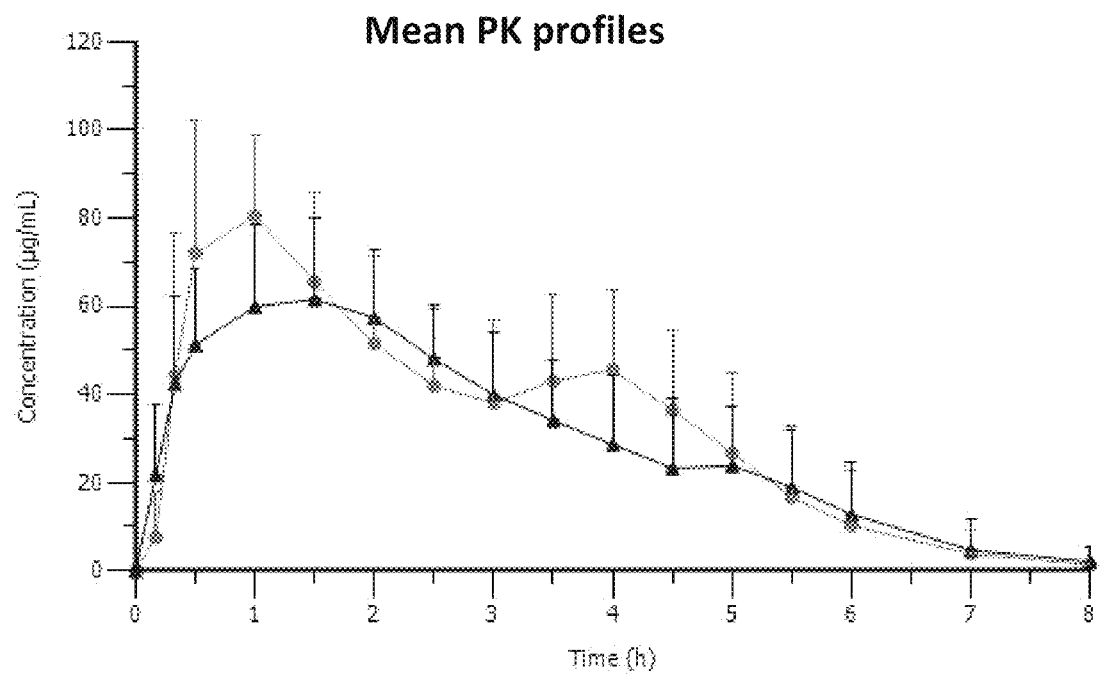
FIG. 2A is a mean concentration versus time curve for 6 g FT218 administered in the fed and fasted state.

An embodiment of the composition of gamma-hydroxybutyrate yields a plasma concentration versus time curve when administered at a strength of 6 g less than two hours after a standardized evening meal substantially as depicted in FIG. 2A.

Figure 4A:
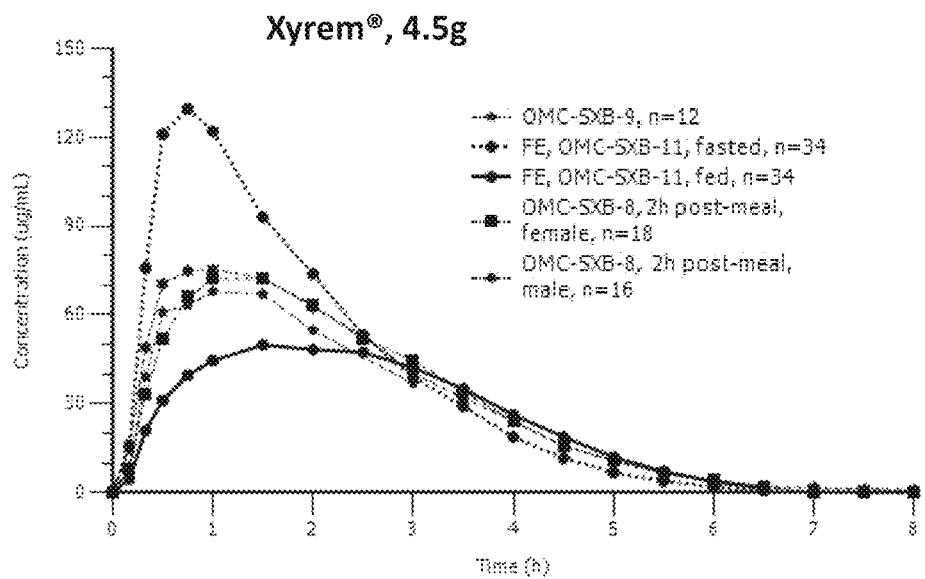
FIG. 4A is a concentration versus time curve for a 4.5 g single dose of Xyrem® in the fed state, the fasted state and 2 hours post meal.
Figure 4B:
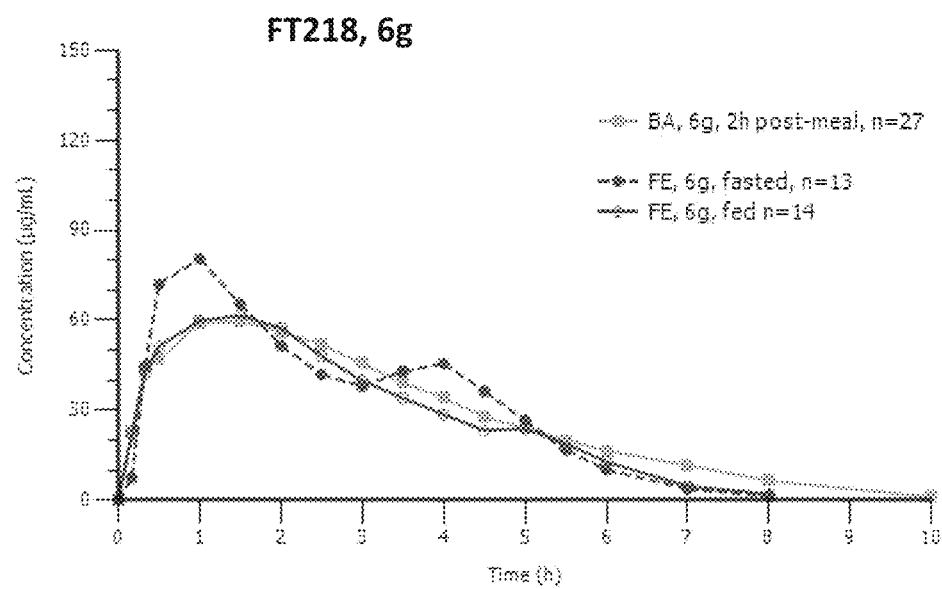
FIG. 4B is a concentration versus time curve for a 6 g dose of FT218 in the fed state, the fasted state and 2 hours post meal.

Another embodiment of the composition of gamma-hydroxybutyrate yields a plasma concentration versus time curve when administered once nightly at a strength of 6 g less than two hours after eating substantially as depicted in FIG. 4B.

Figure 5A:
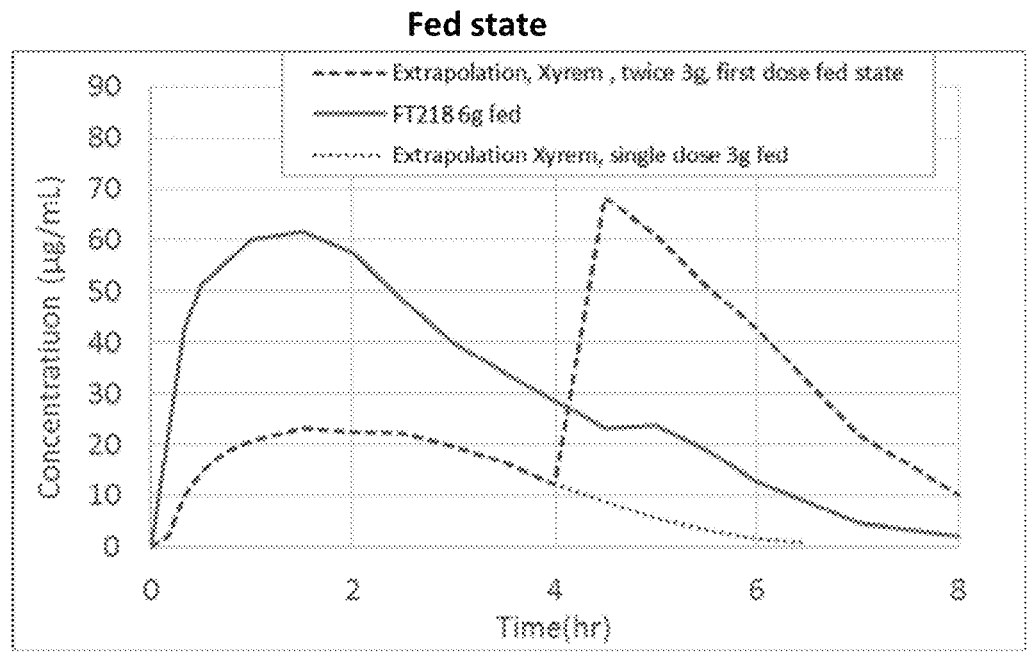
FIG. 5A shows expected concentration versus time curves for two 3 g doses of Xyrem® and one 6 g dose of FT218 in the fed state.

Yet another embodiment of the composition of gamma-hydroxybutyrate yields a plasma concentration versus time curve when administered once nightly at a strength of 6 g less than two hours after eating substantially as depicted in FIG. 5A.

Figure 6A:
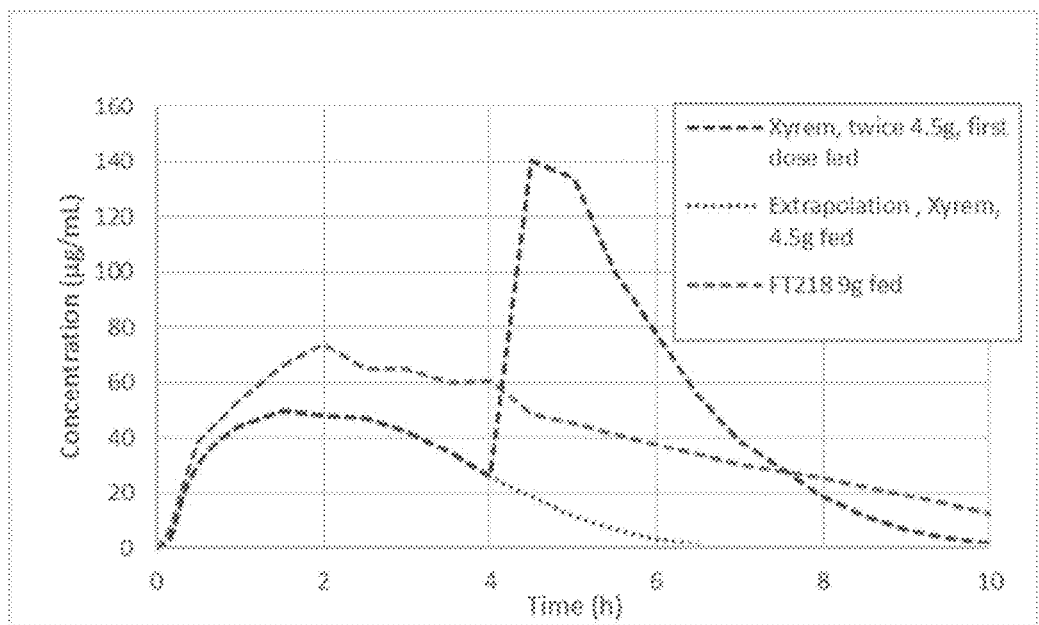
FIG. 6A shows expected concentration versus time curves for two 4.5 g doses of Xyrem® and one 9 g dose of FT218 in the fed state.

An embodiment of the composition of gamma-hydroxybutyrate yields a plasma concentration versus time curve when administered once nightly at a strength of 9 g less than two hours after eating substantially as depicted in FIG. 6A.

Figure 7A:
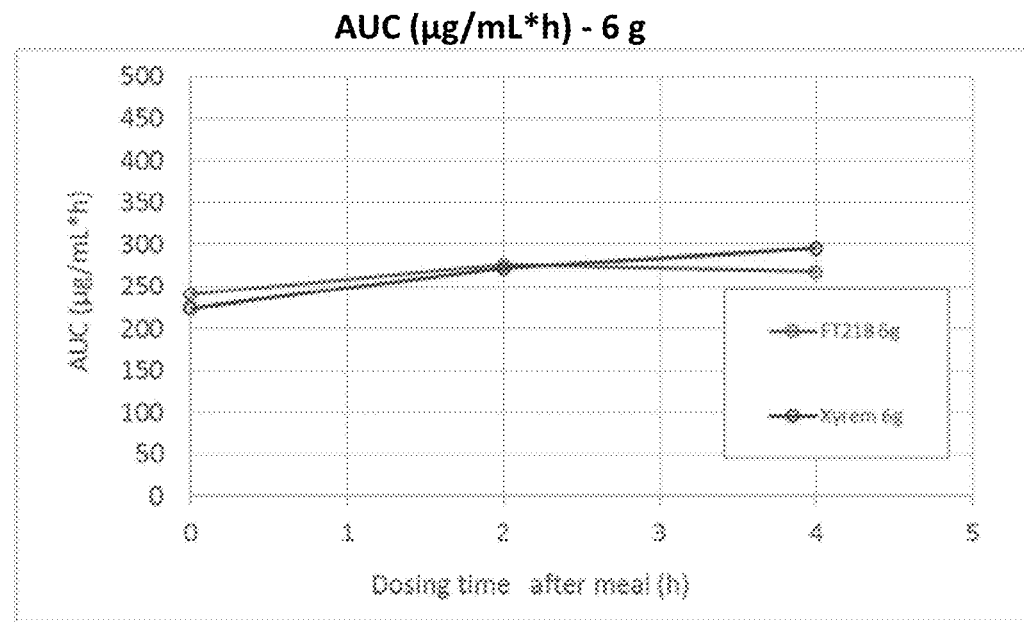
FIG. 7A shows AUC versus time after a meal for 6 g FT218 and 6 g Xyrem®.

Another embodiment of the composition of gamma-hydroxybutyrate yields an AUC profile when administered once nightly at a strength of 6 g between 0 and 4 hours after eating substantially as depicted in FIG. 7A.

Figure 7B:
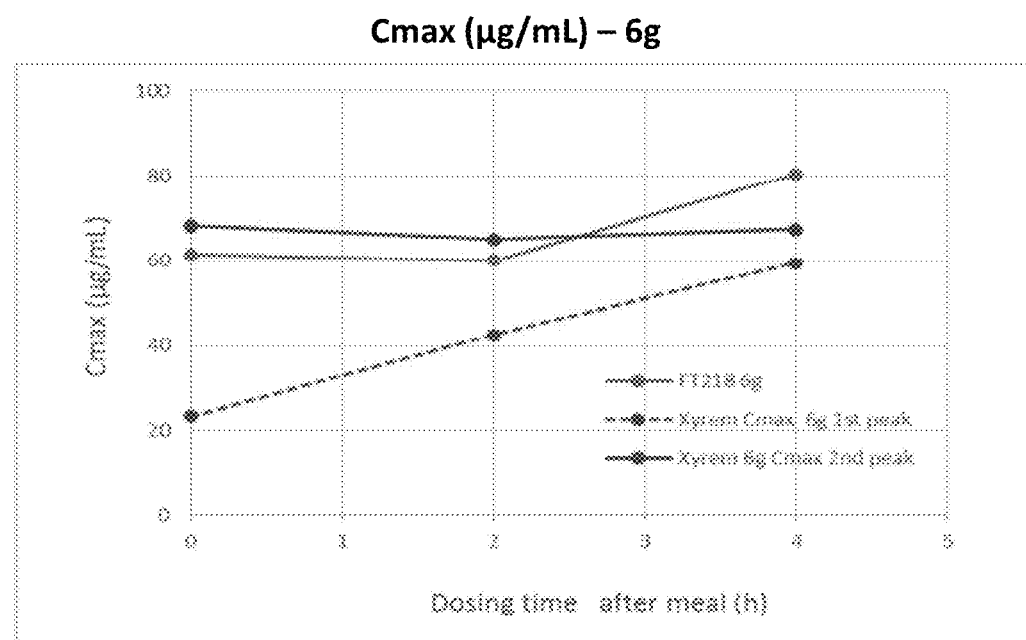
FIG. 7B shows $C_{max}$ versus time after a meal for 6 g FT218 and 6 g Xyrem®.

Yet another embodiment of the composition of gamma-hydroxybutyrate yields a $C_{max}$ profile when administered once nightly at a strength of 6 g between 0 and 4 hours after a standardized evening meal substantially as depicted in FIG. 7B.

In any of these embodiments, the formulation may be effective to treat narcolepsy Type 1 or Type 2. The treatment of narcolepsy is defined as reducing excessive daytime sleepiness or reducing the frequency of cataplectic attacks. In various embodiments, the composition is sufficient to be administered once daily. For example, the composition may be sufficient to administer in the morning or at night less than 2 hours after eating a meal. The formulation is also effective to induce sleep for at least 6 to 8 consecutive hours. In one embodiment, the composition administered less than two hours after eating is effective to induce sleep for at least 8 consecutive hours. In various embodiments, the formulation is effective to induce sleep for at least 6 hours, at least 7 hours, at least 8 hours, at least 9 hours, or at least 10 hours. In other embodiments, the formulation is effective to induce sleep for up to 6 hours, up to 7 hours, up to 8 hours, up to 9 hours, or up to 10 hours.

In any of these embodiments, the composition may include immediate release and modified release portions, where the modified release portion includes gamma hydroxybutyrate particles coated by a polymer carrying free carboxylic groups and a hydrophobic compound having a melting point equal or greater than 40° C., and the ratio of gamma-hydroxybutyrate in the immediate release portion and the modified release portion is from 10/90 to 65/35. The polymers comprising free carboxylic groups may have a pH dissolution trigger of from 5.5 to 6.97 and may be methacrylic acid copolymers having a pH dissolution trigger of from 5.5 to 6.97.

Structural Embodiments

Various techniques are known for formulating modified release dosage forms including, for example, the techniques described in U.S. Pat. No. 8,101,209 to Legrand et al. ("Legrand"). Legrand provides a system ensuring that the active ingredient is released with certainty from the modified release dosage form by means of a dual mechanism of "time-dependent" and "pH-dependent" release. Legrand did not describe any dosage forms for delivering sodium oxybate or other forms of gamma-hydroxybutyrate administered less than two hours after eating.

In various embodiments, the composition of any of the embodiments herein may be administered at any meal state. In particular, the composition may be administered in the fed state, at least two hours after eating, or in the fasted state. In one embodiment, the composition is administered in the fed state, which is less than two hours after eating. For example, the composition may be administered while eating, immediately after eating, up to 30 minutes after eating, at least 30 minutes after eating, up to 45 minutes after eating, up to 1 hour after eating, up to 1.25 hours after eating, up to 1.5 hours after eating, up to 1.75 hours after eating, up to 1.8 hours after eating, up to 1.9 hours after eating, or up to 1.95 hours after eating. In some embodiments, the composition may be administered less than two hours after eating a standardized evening meal.

In an embodiment, the composition of gamma-hydroxybutyrate may include immediate release and modified release portions, wherein: (a) the modified release portion comprises coated particles of gamma-hydroxybutyrate; (b) the coating comprises a polymer carrying free carboxylic groups and a hydrophobic compound having a melting point equal or greater than 40° C.; and (c) the ratio of gamma-hydroxybutyrate in the immediate release portion and the modified release portion is from 10/90 to 65/35.

In an embodiment, the composition of gamma-hydroxybutyrate may include immediate release and modified release portions, a suspending or viscosifying agent, and an acidifying agent, wherein: (a) the modified release portion comprises coated particles of gamma-hydroxybutyrate; (b) the coating comprises a polymer carrying free carboxylic groups and a hydrophobic compound having a melting point equal or greater than 40° C.; and (c) the ratio of gamma-hydroxybutyrate in the immediate release portion and the modified release portion is from 10/90 to 65/35.

In an embodiment, the composition of gamma-hydroxybutyrate may include immediate release and modified release portions, wherein: (a) the modified release portion comprises coated particles of gamma-hydroxybutyrate; (b) the coating comprises a polymer carrying free carboxylic groups and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35; and (e) the coating is from 10 to 50% of the weight of the particles.

In an embodiment, the composition of gamma-hydroxybutyrate may include immediate release and modified release portions, wherein: (a) the modified release portion comprises coated particles of gamma-hydroxybutyrate; (b) the coating comprises a polymer carrying free carboxylic groups having a pH trigger of from 5.5 to 6.97 and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35; and (e) the coating is from 10 to 50% of the weight of the particles.

In an embodiment, the composition of gamma-hydroxybutyrate may include immediate release and modified release portions, wherein: (a) the modified release portion comprises coated particles of gamma-hydroxybutyrate; (b) the coating comprises a methacrylic acid copolymer carrying free carboxylic groups having a pH trigger of from 5.5 to 6.97 and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35; and (e) the coating is from 10 to 50% of the weight of the particles.

In various embodiments, gamma-hydroxybutyrate may be present in the composition as a 4.5 g, 6.0 g, 7.5 g, or 9.0 g dose. In some embodiments, the dosage of gamma-hydroxybutyrate may be sufficient to administer the composition once daily.

Pharmacokinetics

As mentioned in the definitions section of this document, each of the sub-embodiments may be used to further characterize and limit each of the foregoing principal embodiments. In addition, more than one of the following sub-embodiments may be combined and used to further characterize and limit each of the foregoing principal embodiments, in any manner that is mathematically and physically possible.

In an embodiment, the oral pharmaceutical composition of gamma-hydroxybutyrate may be in a unit dose suitable for administration less than two hours after eating for the treatment of narcolepsy, cataplexy, or excessive daytime sleepiness. Without being limited to a particular theory, the composition may include a modified release portion that delays release of a portion of the gamma-hydroxybutyrate until the composition reaches the small intestine, such that ingestion of food has a limited effect on the absorption of the gamma-hydroxybutyrate.

In an embodiment, the oral pharmaceutical composition of gamma-hydroxybutyrate may be in a unit dose suitable for administration once daily for the treatment of narcolepsy, cataplexy, or excessive daytime sleepiness. In an example, the composition may exhibit rapid initial absorption comparable to twice-nightly IR sodium oxybate. In another example, the composition may demonstrate a lower overall $C_{max}$ than twice-nightly IR sodium oxybate. In other examples, the composition may provide mean blood concentrations (ug/ml) at 8 hours similar to that of twice-nightly IR sodium oxybate.

In various embodiments, the composition provides a substantially similar fed state PK profile and 2 hour post meal administration PK profile. In some embodiments, a 4.5 g, 7.5 g, and/or 9 g dose may exhibit a PK profile consistent with those desired for once-nightly dosing. In various embodiments, the composition exhibits pharmacokinetics that are dose proportional when administered once daily, 2 hours post meal. In an embodiment, the composition provides a $C_{max}$ that is dose proportional. For example, the composition provides a $C_{max}$ that is dose proportional across once daily doses of 4.5 g, 7.5 g, and 9 g. In an embodiment, the composition provides an AUC that is dose proportional. For example, the $C_{max}$ of a 6 g dose is proportional to the $C_{max}$ of a 9 g dose of the composition. In another embodiment, the composition is dose proportional by a factor of about 1 to about 1.3. In an example, the $C_{max}$ may be dose proportional by a factor of about 1. In another example, the AUC may be dose proportional by a factor of about 1.3. In some examples, the increase in the AUC may be slightly more than proportional. The composition may exhibit predictable increases in plasma levels with increasing doses, consistent with the PK profile desired for a once-nightly sodium oxybate formulation.

In an embodiment, the once-nightly controlled-release sodium oxybate composition may demonstrate lower overall $C_{max}$ and similar total AUC, compared to twice-nightly sodium oxybate. In an embodiment, the once-nightly composition safety profile may be consistent with what is known for sodium oxybate.

In an embodiment, the composition provides no dose dumping. For example, the ingestion of alcohol does not result in an immediate release of gamma-hydroxybutyrate.

In another embodiment, there is no significant reduction in safety or efficacy to a patient following administration of the composition less than two hours after eating. In some embodiments, the safety is improved over the administration of Xyrem®, such that the $C_{max}$ of the composition is less than the $C_{max}$ after administration of the second dose of Xyrem® when administered in the fed state. In other embodiments, the composition is more effective than Xyrem® when administered in the fed state. For example, the $C_{max}$ of the composition is higher than the $C_{max}$ after administration of the first dose of Xyrem® when administered in the fed state.

In an embodiment, the composition provides an $AUC_{inf}$ bioequivalent to an $AUC_{inf}$ of Xyrem® as depicted in a figure selected from FIGS. 4A, 5A, 5B, 6A, 6B, and 7A. In an embodiment, the composition provides a $C_{max}$ that is less than the $C_{max}$ Of Xyrem® as depicted in a figure selected from FIGS. 4A, 5A, 5B, 6A, 6B, 7A, and 7B. In an embodiment, the composition provides a $C_{max}$ that is substantially less than the $C_{max}$ of Xyrem® as depicted in a figure selected from FIGS. 4A, 5A, 5B, 6A, 6B, and 7B. In an embodiment, the composition provides a $C_{max}$ that is 10-60% less than the $C_{max}$ Of Xyrem® as depicted in a figure selected from FIGS. 4A, 5A, 5B, 6A, 6B, and 7B. In an embodiment, the composition provides an AUC that is more dose proportional than the AUC of Xyrem® as depicted in a figure selected from FIGS. 4A, 5A, 5B, 6A, 6B, and 7A.

In various embodiments, a 6 g dose of the composition of gamma-hydroxybutyrate may be characterized as having been shown to achieve a mean $AUC_{inf}$ of greater than 230, 240, 245, 250, 255, 260, 275, 300, 325, or 350 hr*microgram/mL when administered once less than two hours after eating. An upper limit on mean $AUC_{inf}$ for such 6 g dose may be set at 300 or 350 hr*µg/mL. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In additional embodiments, a 6 g dose of the composition of gamma-hydroxybutyrate may be characterized as having been shown to achieve a mean $C_{max}$ of greater than 50, 55, 60, 65, 70, 75, 80, 85, or 90 µg/mL when administered once less than two hours after eating. An upper limit on mean $C_{max}$ for such 6 g dose may be set at 75 or 90 µg/mL. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In additional embodiments, a 6 g dose of the composition of gamma-hydroxybutyrate administered less than two hours after eating may be characterized as having been shown to achieve a mean $C_{max}$ that is from 50% to 140%, from 60% to 140%, from 70 to 140%, from 75% to 135%, from 80% to 135%, or from 80 to 130% of the mean $C_{max}$ provided by an equal dose of immediate release liquid solution of gamma-hydroxybutyrate administered at $t_0$ and $t_{4h}$ in two equally divided doses administered at least two hours after a standardized meal. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In various embodiments, a 6 g dose of the composition of gamma-hydroxybutyrate may be characterized as having been shown to achieve a mean $AUC_{8h}$ of greater than 1, 2, 3, 4, 5, or 6 µg/mL when administered once less than two hours after eating. An upper limit on mean $AUC_{8h}$ for such 6 g dose may be set at 5 or 6 µg/mL. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In various embodiments, a 6 g dose of the composition of gamma-hydroxybutyrate may be characterized as having been shown to achieve a mean $AUC_{0-8}$ of greater than 150, 175, 200, 225, 250, 300, or 350 hr*µg/mL when administered once less than two hours after eating. An upper limit on mean $AUC_{0-8}$ for such 6 g dose may be set at 300 or 350 hr*µg/mL. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In various embodiments, a 6 g dose of the composition of gamma-hydroxybutyrate may be characterized as having been shown to achieve a mean $AUC_{0-t}$ of greater than 150, 175, 200, 225, 250, 300, or 350 hr*µg/mL when administered once less than two hours after eating. An upper limit on mean $AUC_{0-t}$ for such 6 g dose may be set at 300 or 350 hr*µg/mL. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In various embodiments, a 6 g dose of the composition of gamma-hydroxybutyrate may be characterized as having been shown to achieve a mean % AUC, ext of greater than 0.1%, 0.2%, or 0.3% when administered once less than two hours after eating. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In various embodiments, a 6 g dose of the composition of gamma-hydroxybutyrate may be characterized as having been shown to achieve a $t_{max}$ of greater than 0.5, 1, 1.5, 2, or 2.5 hours when administered once less than two hours after eating. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In various embodiments, a 6 g dose of the composition of gamma-hydroxybutyrate may be characterized as having been shown to achieve a mean $t_{1/2}$ of greater than 0.5, 1, or 1.5 hours when administered once less than two hours after eating. In these embodiments, the 6 g dose of the composition may be administered less than two hours after eating a meal. For example, the 6 g dose of the composition may be administered once daily, in the morning or the evening. In other embodiments, the 6 g dose of the composition may be administered in the fed state.

In one embodiment, a 6 g dose of the composition administered less than two hours after eating may achieve a mean $AUC_{inf}$ of greater than 230 hr·µg/mL, and a mean $C_{max}$ that is from 50% to 140% of the mean $C_{max}$ provided by an equal dose of immediate release liquid solution of sodium oxybate administered at $t_0$ and $t_{4h}$ in equally divided doses at least two hours after eating.

In various embodiments, a 9 g dose of the composition of gamma-hydroxybutyrate administered less than two hours after eating may be characterized as having been shown to achieve a mean $AUC_{inf}$ of greater than 350, 400, 450, 460, 470, 480, 490, 500, 525, 550, 575, or 600 hr*µg/mL. An upper limit on mean $AUC_{inf}$ for such 9 g dose may be set at 550 or 600 hr*microgram/mL. In these embodiments, the 9 g dose of the composition may be administered less than two hours after eating a meal. For example, the 9 g dose of the composition may be administered once daily, in the morning or the evening. In other embodiments, the 9 g dose of the composition may be administered in the fed state.

In additional embodiments, a 9 g dose of the composition of gamma-hydroxybutyrate administered less than two hours after eating may be characterized as having a mean $C_{max}$ of greater than 60, 65, 70, 75, 80, 85, 90, 95, or 100 µg/mL. An upper limit on mean $C_{max}$ for such 9 g dose may be set at 125 or 100 µg/mL. In these embodiments, the 9 g dose of the composition may be administered less than two hours after eating a meal. For example, the 9 g dose of the composition may be administered once daily, in the morning or the evening. In other embodiments, the 9 g dose of the composition may be administered in the fed state.

In additional embodiments, a 9 g dose of the composition of gamma-hydroxybutyrate administered less than two hours after eating may be characterized as having a mean $C_{max}$ that is from 50% to 120% or from 60% to 120% of the mean $C_{max}$ provided by an equal dose of immediate release liquid solution of gamma-hydroxybutyrate administered at $t_0$ and $t_{4h}$ in two equally divided doses administered at least two hours after a standardized meal. In these embodiments, the 9 g dose of the composition may be administered less than two hours after eating a meal. For example, the 9 g dose of the composition may be administered once daily, in the morning or the evening. In other embodiments, the 9 g dose of the composition may be administered in the fed state.

In one embodiment, a 9 g dose of the composition administered less than two hours after eating may achieve a mean $AUC_{inf}$ of greater than 500 hr·µg/mL, and a mean $C_{max}$ that is from 50% to 120% of the mean $C_{max}$ provided by an equal dose of immediate release liquid solution of sodium oxybate administered at $t_0$ and $t_{4h}$ in equally divided doses at least two hours after a standardized evening meal.

Figure 3A:
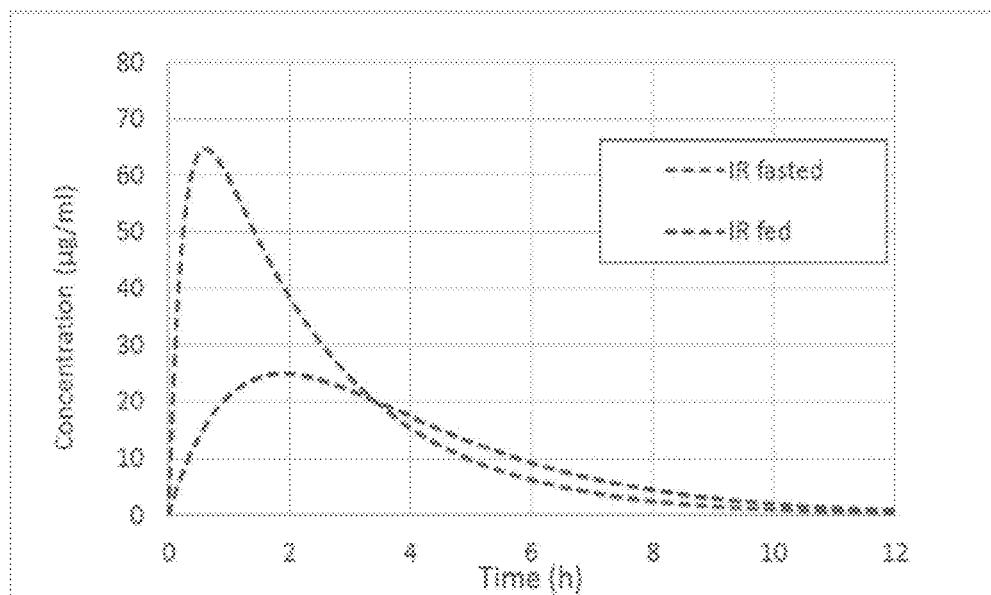
FIG. 3A is a simulated concentration versus time curve for 3 g IR microparticles of FT218 administered in the fed and fasted state.
Figure 3B:
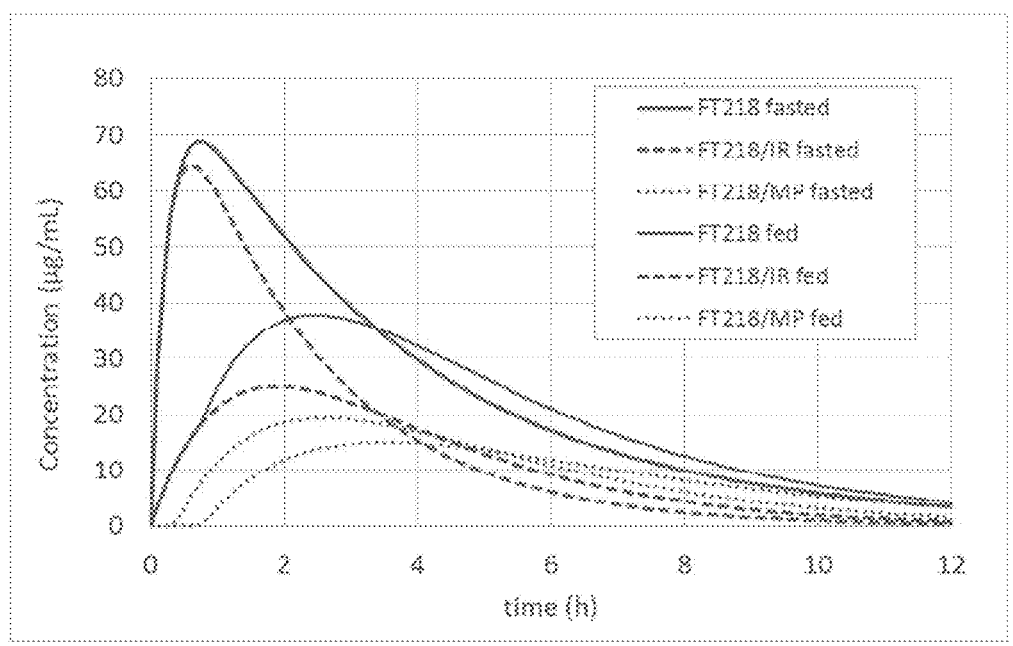
FIG. 3B is a simulated concentration versus time curve for 6 g FT218 and IR and MR microparticle portions of FT218 administered in the fed and fasted state.

Still further embodiments may be defined based on a pharmacokinetic comparison of the composition of gamma-hydroxybutyrate to an immediate release solution of gamma-hydroxybutyrate. Therefore, in additional embodiments, the composition of gamma-hydroxybutyrate administered less than two hours after eating may achieve a relative bioavailability (RBA) of greater than 80%, 85%, 90%, or 95% when compared to an equal dose of an immediate release liquid solution of sodium oxybate administered at $t_0$ and $t_{4h}$ in equally divided doses administered at least two hours after a standardized meal. For example, a 6 g and 9 g dose of the formulation administered less than two hours after eating may have an RBA of greater than 80%, 85% or 90% when compared to an equal dose of an immediate release liquid solution of sodium oxybate administered at $t_0$ and $t_{4h}$ in equally divided doses administered at least two hours after a standardized meal The compositions of gamma-hydroxybutyrate may also be defined by the concentration/time curves that they produce when tested according to the Examples. Therefore, in other embodiments, a 6 g or 9 g dose of the composition of gamma-hydroxybutyrate administered less than two hours after eating may achieve a time/concentration curve substantially as shown in FIGS. 5A and 6A respectively herein. In other embodiments, the composition may achieve a time/concentration curve substantially as shown in FIG. 2A, 3B, or 4B herein.

The compositions of gamma-hydroxybutyrate may also be defined based on the time required to reach maximum blood concentration of gamma-hydroxybutyrate. Thus, in additional embodiments, the composition of gamma-hydroxybutyrate may achieve a mean $T_{max}$ of 0.5 to 2.5 hours. In various embodiments, the composition of gamma-hydroxybutyrate may achieve a mean $T_{max}$ of about 0.5, 0.75, 1.0, 1.25, 1.5, 1.75, 2.0, 2.25, or 2.5 hours when administered less than two hours after eating. A lower limit on the median $T_{max}$ in any of the foregoing ranges can alternatively be set at 0.5 or 1.0 hours.

In another embodiment, a 6 g dose of the composition may achieve a mean $AUC_{inf}$ of greater than 230 hr·μg/mL and a mean $C_{max}$ of greater than 60 microgram/mL when administered less than two hours after eating.

In still another embodiment, a 9 g dose of the formulation may achieve a mean $AUC_{inf}$ of greater than 400 hr·μg/mL and a mean $C_{max}$ of greater than 60 microgram/mL when administered less than two hours after eating.

Figure 8:
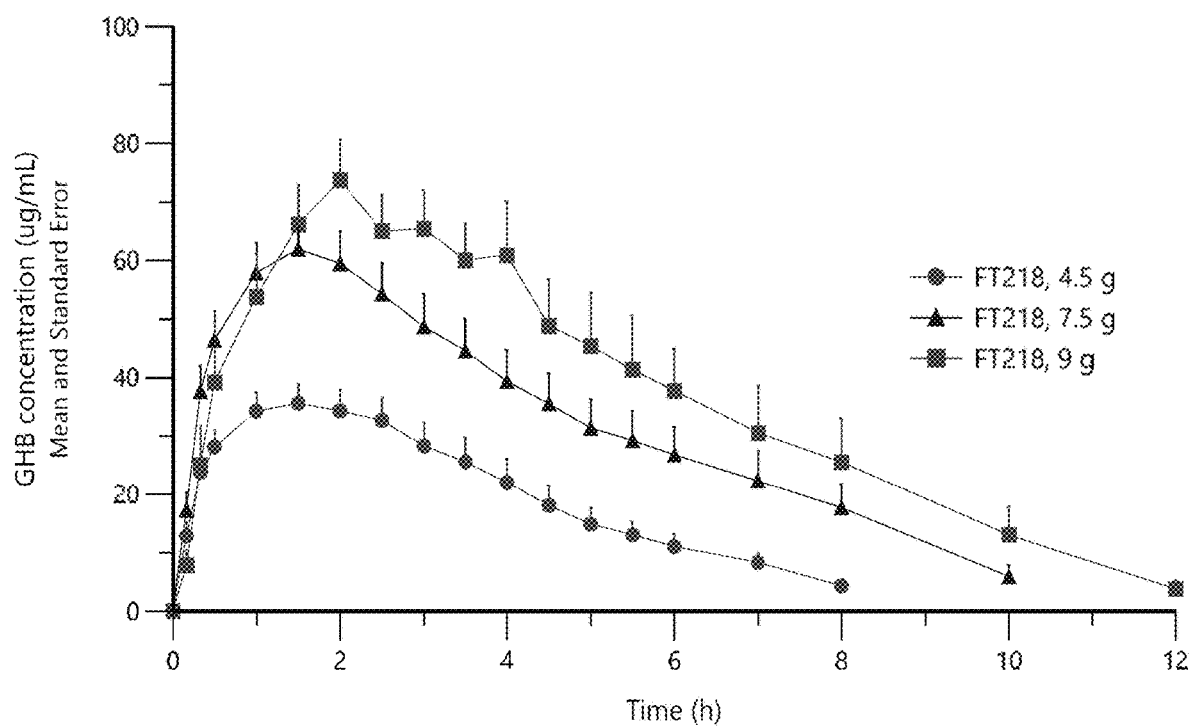
FIG. 8 shows FT218 plasma concentration time curves for rising doses from 4.5 g to 9 g per night.

In an embodiment, 4.5 g, 7.5 g and 9 g doses of the composition may exhibit similar overall mean pharmacokinetics profiles when administered once daily, 2 hours after eating. In some embodiments, 4.5 g, 7.5 g and 9 g doses of the composition may exhibit mean pharmacokinetics profiles as shown in FIG. 8 when administered once daily, 2 hours after eating. In an example, 4.5 g, 7.5 g and 9 g doses of the composition may exhibit a median $T_{max}$ between 1.5 and 2 hours (FIG. 8). In an example, 4.5 g, 7.5 g and 9 g doses of the composition may achieve a mean $C_{max}$ from 42.9 to 84.5 μg/mL across the increasing doses. Following $C_{max}$, blood levels may gradually decrease overnight. In an example, the composition may achieve a mean $AUC_{inf}$ of 191, 358 and 443 μg·h/mL for the 4.5, 7.5 and 9 g doses respectively when administered once daily, 2 hours after eating. In an example, the composition may exhibit mean concentrations at 8 hours of 4.8, 19.7 and 25.5 μg/mL for the 4.5, 7.5 and 9 g doses respectively when administered once daily, 2 hours after eating.

Structural Embodiments

The compositions of gamma-hydroxybutyrate may be provided in any dosage form that is suitable for oral administration, including tablets, capsules, liquids, orally dissolving tablets, and the like. In one embodiment, they are provided as dry particulate formulations (i.e. granules, powders, coated particles, microparticles, pellets, microspheres, etc.), in a sachet or other suitable discreet packaging units. A particulate formulation will be mixed with tap water shortly before administration. In one embodiment, the composition may be mixed with 50 mL water prior to administration. In another embodiment, the composition is an oral pharmaceutical composition.

In various embodiments, the composition includes gamma-hydroxybutyrate present in a unit dose of at least 4.5 g, at least 6.0 g, at least 7.5 g, or at least 9.0 g. In various embodiments, the composition includes gamma-hydroxybutyrate present in a unit dose of more than 4.5 g, more than 6.0 g, more than 7.5 g, or more than 9.0 g. In one embodiment, the formulation includes 6 g gamma-hydroxybutyrate. In another embodiment, the formulation includes 9 g gamma-hydroxybutyrate.

In one embodiment, the formulation comprises immediate release and modified release portions, wherein: (a) the modified release portion comprises coated microparticles of gamma-hydroxybutyrate; and (b) the ratio of gamma-hydroxybutyrate in the immediate release portion and the modified release portion is from 10/90 to 65/35.

In one embodiment, the formulation comprises immediate release and modified release portions, wherein: (a) the modified release portion comprises coated microparticles of gamma-hydroxybutyrate; and (b) the ratio of gamma-hydroxybutyrate in the immediate release portion and the modified release portion is from 40/60 to 60/40.

In another embodiment, the formulation comprises immediate release and modified release portions, wherein: (a) the modified release portion comprises coated microparticles of gamma-hydroxybutyrate; (b) the coating of said modified release particles of gamma-hydroxybutyrate comprises a polymer carrying free carboxylic groups and a hydrophobic compound having a melting point equal or greater than 40° C.; and (c) the ratio of gamma-hydroxybutyrate in the immediate release portion and the modified release portion is from 10/90 to 65/35 or 40/60 to 60/40.

In another embodiment, the formulation comprises immediate release and modified release portions, wherein: (a) the modified release portion comprises coated microparticles of gamma-hydroxybutyrate; (b) the coating of said modified release particles of gamma-hydroxybutyrate comprises a polymer carrying free carboxylic groups and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35 or 40/60 to 60/40; and (e) the film coating is from 10 to 50% of the weight of the microparticles.

In another embodiment the formulation comprises immediate release and modified release portions, wherein: (a) the modified release portion comprises coated particles of gamma-hydroxybutyrate; (b) the coating of said modified release particles of gamma-hydroxybutyrate comprises a polymer carrying free carboxylic groups having a pH trigger of from 5.5 to 6.97 and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35 or 40/60 to 60/40; and (e) the coating is from 10 to 50% of the weight of the particles.

In an embodiment, the polymer carrying free carboxylic groups comprises from 100% poly (methacrylic acid, ethyl acrylate) 1:1 and 0% poly (methacrylic acid, methylmethacrylate) 1:2 to 2% poly (methacrylic acid, ethyl acrylate) 1:1 and 98% poly (methacrylic acid, methylmethacrylate) 1:2; and the hydrophobic compound comprises hydrogenated vegetable oil.

In an embodiment, the formulation includes excipients to improve the viscosity and the pourability of the mixture of the particulate formulation with tap water. As such, the particulate formulation comprises, besides the immediate release and modified release particles of gamma-hydroxybutyrate, one or more suspending or viscosifying agents or lubricants.

Suspending or viscosifying agents may be chosen from the group consisting of xanthan gum, medium viscosity sodium carboxymethyl cellulose, mixtures of microcrystalline cellulose and sodium carboxymethyl cellulose, mixtures of microcrystalline cellulose and guar gum, medium viscosity hydroxyethyl cellulose, agar, sodium alginate, mixtures of sodium alginate and calcium alginate, gellan gum, carrageenan gum grade iota, kappa or lambda, and medium viscosity hydroxypropylmethyl cellulose.

Medium viscosity sodium carboxymethyl cellulose corresponds to grade of sodium carboxymethyl cellulose whose viscosity, for a 2% solution in water at 25° C., is greater than 200 mPa·s and lower than 3100 mPa·s.

Medium viscosity hydroxyethyl cellulose corresponds to a grade of hydroxyethyl cellulose whose viscosity, for a 2% solution in water at 25° C., is greater than 250 mPa·s and lower than 6500 mPa·s. Medium viscosity hydroxypropylmethyl cellulose corresponds to a grade of hydroxypropylmethyl cellulose whose viscosity, for a 2% solution in water at 20° C., is greater than 80 mPa·s. and lower than 3800 mPa·s.

In one embodiment, the suspending or viscosifying agents are xanthan gum, especially Xantural 75™ from Kelco, hydroxyethylcellulose, especially Natrasol 250M™ from Ashland, Kappa carrageenan gum, especially Gelcarin PH812™ from FMC Biopolymer, and lambda carrageenan gum, especially Viscarin PH209™ from FMC Biopolymer.

In an embodiment, the composition of gamma-hydroxybutyrate comprises from 1 to 15% of viscosifying or suspending agents. In other embodiments, the composition of gamma-hydroxybutyrate comprises viscosifying or suspending agents in an amount from 2 to 10%, from 2 to 5%, or from 2 to 3% of the formulation.

In an embodiment, the composition of gamma-hydroxybutyrate is in the form of a powder that is intended to be dispersed in water prior to administration and further comprises from 1 to 15% of a suspending or viscosifying agent selected from a mixture of xanthan gum, carrageenan gum and hydroxyethylcellulose or xanthan gum and carrageenan gum.

In an embodiment, the composition of gamma-hydroxybutyrate is in the form of a powder that is intended to be dispersed in water prior to administration and further comprises: from 1.2 to 15% of an acidifying agent selected from malic acid and tartaric acid; and from 1 to 15% of a suspending or viscosifying agent selected from a mixture of xanthan gum, carrageenan gum and hydroxyethylcellulose or xanthan gum and carrageenan gum.

In one embodiment, the composition of gamma-hydroxybutyrate comprises about 1% of lambda carrageenan gum or Viscarin PH209™, about 1% of medium viscosity grade of hydroxyethyl cellulose or Natrosol 250M™, and about 0.7% of xanthan gum or Xantural 75™. For a 4.5 g dose unit, these percentages will typically equate to about 50 mg xanthan gum (Xantural 75™), about 75 mg carrageenan gum (Viscarin PH209™), and about 75 mg hydroxyethylcellulose (Natrasol 250M™).

Alternative packages of viscosifying or suspending agents, for a 4.5 g dose, include about 50 mg xanthan gum (Xantural 75™) and about 100 mg carrageenan gum (Gelcarin PH812™), or about 50 mg xanthan gum (Xantural 75™), about 75 mg hydroxyethylcellulose (Natrasol 250M™), and about 75 mg carrageenan gum (Viscarin PH109™).

In an embodiment, the composition of gamma-hydroxybutyrate further comprises a lubricant or a glidant, besides the immediate release and modified release particles of gamma-hydroxybutyrate. In various embodiments, the lubricants and glidants are chosen from the group consisting of salts of stearic acid, in particular magnesium stearate, calcium stearate or zinc stearate, esters of stearic acid, in particular glyceryl monostearate or glyceryl palmitostearate, stearic acid, glycerol behenate, sodium stearyl fumarate, talc, and colloidal silicon dioxide. In one embodiment, the lubricant or glidant is magnesium stearate. The lubricant or glidant may be used in the particulate formulation in an amount of from 0.1 to 5%. In one embodiment, the amount of lubricant or glidant is about 0.5%. For example, the composition of gamma-hydroxybutyrate may include about 0.5% of magnesium stearate.

A composition of gamma-hydroxybutyrate may further include an acidifying agent. The acidifying agent helps to ensure that the release profile of the formulation in 0.1N HCl will remain substantially unchanged for at least 15 minutes after mixing, which is approximately the maximum length of time a patient might require before consuming the dose after mixing the formulation with tap water.

In one embodiment, the formulation is a powder, and further comprising an acidifying agent and a suspending or viscosifying agent in the weight percentages recited herein.

The acidifying agents may be chosen from the group consisting of malic acid, citric acid, tartaric acid, adipic acid, boric acid, maleic acid, phosphoric acid, ascorbic acid, oleic acid, capric acid, caprylic acid, and benzoic acid. In various embodiments, the acidifying agent is present in the formulation from 1.2 to 15%, from 1.2 to 10%, or from 1.2 to 5%. In one embodiment, the acidifying agents are tartaric acid and malic acid. In another embodiment, the acidifying agent is malic acid.

When tartaric acid is employed, it may be employed in an amount of from 1 to 10%, from 2.5 to 7.5%, or about 5%. In various embodiments, the amount of malic acid in the composition of gamma-hydroxybutyrate is from 1.2 to 15%, from 1.2 to 10%, from 1.2 to 5%, or from 1.6% or 3.2%. In one embodiment, the amount of malic acid in the composition of gamma hydroxybutyrate is about 1.6%.

The composition of gamma-hydroxybutyrate includes an immediate release portion and a modified release portion of gamma-hydroxybutyrate, and in an embodiment, the formulation is a particulate formulation that includes a plurality of immediate release gamma-hydroxybutyrate particles and a plurality of modified release gamma-hydroxybutyrate particles. The molar ratio of gamma-hydroxybutyrate in the immediate release and modified release portions ranges from 0.11:1 to 1.86:1, from 0.17:1 to 1.5:1, from 0.25:1 to 1.22:1, from 0.33:1 to 1.22:1, from 0.42:1 to 1.22:1, from 0.53:1 to 1.22:1, from 0.66:1 to 1.22:1, from 0.66:1 to 1.5:1, from 0.8:1 to 1.22:1. In one embodiment, the molar ratio of gamma-hydroxybutyrate in the immediate release and modified release portions is about 1:1. The molar percentage of gamma-hydroxybutyrate in the immediate release portion relative to the total of gamma-hydroxybutyrate in the formulation ranges from 10% to 65%, from 15 to 60%, from 20 to 55%, from 25 to 55%, from 30 to 55%, from 35 to 55%, from 40 to 55%, from 40 to 60%, or from 45 to 55%. In one embodiment, the molar percentage of gamma-hydroxybutyrate in the immediate release portion relative to the total of gamma-hydroxybutyrate in the formulation ranges from 40% to 60%. In an embodiment, the molar percentage of the gamma-hydroxybutyrate in the immediate release portion relative to the total of gamma-hydroxybutyrate in the formulation is about 50%. The molar percentage of gamma-hydroxybutyrate in the modified release portion relative to the total of gamma-hydroxybutyrate in the formulation ranges from 90% to 35%, from 85 to 40%, from 80 to 45%, from 75 to 45%, from 70 to 45%, from 65 to 45%, from 60 to 45%, from 60 to 40%, or from 55 to 45%. In an embodiment, the molar percentage of gamma-hydroxybutyrate in the modified release portion relative to the total of gamma-hydroxybutyrate in the formulation ranges from 60% to 40%. In one embodiment, the molar ratio of the gamma-hydroxybutyrate in the modified release portion relative to the total of gamma-hydroxybutyrate in the formulation is about 50%. The weight percentage of the IR microparticles relative to the total weight of IR microparticles and MR microparticles ranges from 7.2% to 58.2%, from 11.0% to 52.9%, from 14.9% to 47.8%, from 18.9% to 47.8%, from 23.1% to 47.8%, from 27.4% to 47.8%, from 31.8% to 47.8%, from 31.8% to 52.9%, or from 36.4% to 47.8%. In other embodiments, the weight percentage of the IR microparticles relative to the total weight of IR microparticles and MR microparticles ranges from 5.9% to 63.2%, from 9.1% to 58.1%, from 12.4% to 53.1%, from 19.9% to 53.1%, from 19.6% to 53.1%, from 23.4% to 53.1%, from 27.4% to 53.1%, or from 27.4% to 58.1%. In one embodiment, the weight percentage of the IR microparticles relative to the total weight of IR microparticles and MR microparticles ranges from 31.7% to 53.1%.

In an embodiment, the finished formulation comprises 50% of its sodium oxybate content in immediate-release particles consisting of 80.75% w/w of sodium oxybate, 4.25% w/w of Povidone K30 and 15% of microcrystalline cellulose spheres with a volume mean diameter of about 95 microns to 450 microns and 50% of its sodium oxybate content in modified release particles consisting of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 50% of its sodium oxybate content in immediate-release particles consisting of 80.75% w/w of sodium oxybate, 4.25% w/w of Povidone K30 and 15% of microcrystalline cellulose spheres with a volume mean diameter of about 95 microns to 170 microns and 50% of its sodium oxybate content in modified release particles consisting of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 50% of its sodium oxybate content in immediate-release particles consisting of 80.75% w/w of sodium oxybate, 4.25% w/w of Povidone K30 and 15% of microcrystalline cellulose spheres with a volume mean diameter of about 95 microns to about 450 microns and 50% of its sodium oxybate content in modified release particles consisting of 11.3% w/w of microcrystalline cellulose spheres with a volume mean diameter of about 95 microns to about 450 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

In an embodiment, the finished formulation comprises 50% of its sodium oxybate content in immediate-release particles consisting of 80.75% w/w of sodium oxybate, 4.25% w/w of Povidone™ K30 and 15% of microcrystalline cellulose spheres with a volume mean diameter of about 95 microns to about 170 microns and 50% of its sodium oxybate content in modified release particles consisting of 11.3% w/w of microcrystalline cellulose spheres with a volume mean diameter of about 95 microns to about 170 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

In an embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 450 microns and 50% of its gamma-hydroxybutyrate content in modified release particles consisting of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 170 microns and 50% of its gamma-hydroxybutyrate content in modified release particles consisting of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 16.7% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 450 microns, 16.7% of its gamma-hydroxybutyrate content in immediate-release particles consisting of 80.75% w/w of magnesium salt of gamma-hydroxybutyric acid, 4.25% w/w of Povidone K30 and 15% of microcrystalline cellulose spheres with a volume mean diameter of about 95 microns to about 450 microns, 16.7% of its gamma-hydroxybutyrate content in immediate-release particles consisting of 80.75% w/w of calcium salt of gamma-hydroxybutyric acid, 4.25% w/w of Povidone K30 and 15% of microcrystalline cellulose spheres with a volume mean diameter of about 95 microns to about 450 microns and 50% of its gamma-hydroxybutyrate content in modified release particles consisting of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 16.7% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 170 microns, 16.7% of its gamma-hydroxybutyrate content in immediate-release particles consisting of 80.75% w/w of magnesium salt of gamma-hydroxybutyric acid, 4.25% w/w of Povidone K30 and 15% of microcrystalline cellulose spheres with a volume mean diameter of about 95 microns to about 170 microns, 16.7% of its gamma-hydroxybutyrate content in immediate-release particles consisting of 80.75% w/w of calcium salt of gamma-hydroxybutyric acid, 4.25% w/w of Povidone K30 and 15% of microcrystalline cellulose spheres with a volume mean diameter of about 95 microns to about 170 microns and 50% of its gamma-hydroxybutyrate content in modified release particles consisting of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 450 microns and 50% of its gamma-hydroxybutyrate content in modified release particles consisting of 10.5% w/w of microcrystalline cellulose spheres with a volume mean diameter of about 95 microns to about 450 microns, layered with 56.5% w/w of calcium salt of gamma-hydroxybutyric acid mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In an embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 170 microns and 50% of its gamma-hydroxybutyrate content in modified release particles consisting of 10.5% w/w of microcrystalline cellulose spheres with a volume mean diameter of about 95 microns to about 170 microns, layered with 56.5% w/w of calcium salt of gamma-hydroxybutyric acid mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

Other Characteristics of Immediate Release Portion

The immediate release portion of the formulation can take any form capable of achieving an immediate release of the gamma-hydroxybutyrate when ingested. For example, when the formulation is a particulate formulation, the formulation can include unmodified "raw" gamma-hydroxybutyrate, rapidly dissolving gamma-hydroxybutyrate granules, particles or microparticles comprised of a core covered by a gamma-hydroxybutyrate loaded layer containing a binder such as povidone.

The IR granules or particles of gamma-hydroxybutyrate may be made using any manufacturing process suitable to produce the required particles, including:

agglomeration of the gamma-hydroxybutyrate sprayed in the molten state, such as the Glatt ProCell™ technique, extrusion and spheronization of the gamma-hydroxybutyrate, optionally with one or more physiologically acceptable excipients, wet granulation of the gamma-hydroxybutyrate, optionally with one or more physiologically acceptable excipients, compacting of the gamma-hydroxybutyrate, optionally with one or more physiologically acceptable excipients, granulation and spheronization of the gamma-hydroxybutyrate, optionally with one or more physiologically acceptable excipients, the spheronization being carried out for example in a fluidized bed apparatus equipped with a rotor, in particular using the Glatt CPS"technique, spraying of the gamma-hydroxybutyrate, optionally with one or more physiologically acceptable excipients, for example in a fluidized bed type apparatus equipped with zig-zag filter, in particular using the Glatt MicroPx™ technique, or spraying, for example in a fluidized bed apparatus optionally equipped with a partition tube or Wurster tube, the gamma-hydroxybutyrate, optionally with one or more physiologically acceptable excipients, in dispersion or in solution in an aqueous or organic solvent on a core.

The immediate release portion of the formulation is in the form of microparticles comprising the immediate release gamma-hydroxybutyrate and optional pharmaceutically acceptable excipients. In an embodiment, the immediate release microparticles of gamma-hydroxybutyrate have a volume mean diameter D(4,3) of from 10 to 1000 microns. In other embodiments, the immediate release microparticles of gamma-hydroxybutyrate have a volume mean diameter D(4,3) of from 95 to 600 microns. In additional embodiments, the immediate release microparticles of gamma-hydroxybutyrate have a volume mean diameter D(4,3) of from 150 to 400 microns. In one embodiment, their volume mean diameter is about 270 microns.

The immediate release particles of gamma-hydroxybutyrate may include a core and a layer deposited on the core that contains the gamma-hydroxybutyrate. The core may be any particle chosen from the group consisting of:

crystals or spheres of lactose, sucrose (such as Compressuc™ PS from Tereos), microcrystalline cellulose (such as Avicel™ from FMC Biopolymer, Cellet™ from Pharmatrans or Celphere™ from Asahi Kasei), sodium chloride, calcium carbonate (such as Omyapure™ 35 from Omya), sodium hydrogen carbonate, dicalcium phosphate (such as Dicafos™ AC 92-12 from Budenheim) or tricalcium phosphate (such as Tricafos™ SC93-15 from Budenheim);

composite spheres or granules, for example sugar spheres comprising sucrose and starch (such as Suglets™ from NP Pharm), spheres of calcium carbonate and starch (such as Destab™ 90 S Ultra 250 from Particle Dynamics) or spheres of calcium carbonate and maltodextrin (such as Hubercal™ CCG4100 from Huber).

The core can also comprise other particles of pharmaceutically acceptable excipients such as particles of hydroxypropyl cellulose (such as Klucel™ from Aqualon Hercules), guar gum particles (such as Grinsted™ Guar from Danisco), xanthan particles (such as Xantural™ 180 from CP Kelco).

According to a particular embodiment of the invention, the cores are sugar spheres or microcrystalline cellulose spheres, such as Cellets™ 90, Cellets™ 100 or Cellets™ 127 marketed by Pharmatrans, or also Celphere™ CP 203, Celphere™ CP305, Celphere™ SCP 100. In one embodiment, the core is a microcrystalline cellulose sphere. For example, the core may be a Cellets™ 127 from Pharmatrans.

In various embodiments, the core has a mean volume diameter of about 95 to about 450 microns, about 95 to about 170 microns, or about 140 microns.

The layer deposited onto the core comprises the immediate release gamma-hydroxybutyrate. In an embodiment, the layer also comprises a binder, which may be chosen from the group consisting of:

low molecular weight hydroxypropyl cellulose (such as Klucel™ EF from Aqualon-Hercules), low molecular weight hydroxypropyl methylcellulose (or hypromellose) (such as Methocel™ E3 or E5 from Dow), or low molecular weight methylcellulose (such as Methocel™ A15 from Dow);

low molecular weight polyvinyl pyrrolidone (or povidone) (such as Plasdone™ K29/32 from ISP or Kollidon™ 30 from BASF), vinyl pyrrolidone and vinyl acetate copolymer (or copovidone) (such as Plasdone: S630 from ISP or Kollidon™ VA 64 from BASF);

dextrose, pregelatinized starch, maltodextrin; and mixtures thereof.

Low molecular weight hydroxypropyl cellulose corresponds to grades of hydroxypropyl cellulose having a molecular weight of less than 800,000 g/mol, less than or equal to 400,000 g/mol, or less than or equal to 100,000 g/mol. Low molecular weight hydroxypropyl methylcellulose (or hypromellose) corresponds to grades of hydroxypropyl methylcellulose the solution viscosity of which, for a 2% solution in water and at 20° C., is less than or equal to 1,000 mPa·s, less than or equal to 100 mPa·s, or less than or equal to 15 mPa·s. Low molecular weight polyvinyl pyrrolidone (or povidone) corresponds to grades of polyvinyl pyrrolidone having a molecular weight of less than or equal to 1,000,000 g/mol, less than or equal to 800,000 g/mol, or less than or equal to 100,000 g/mol.

In some embodiments, the binding agent is chosen from low molecular weight polyvinylpyrrolidone or povidone (for example, Plasdone™ K29/32 from ISP), low molecular weight hydroxypropyl cellulose (for example, Klucel™ EF from Aqualon-Hercules), low molecular weight hydroxypropyl methylcellulose or hypromellose (for example, Methocel™ E3 or E5 from Dow) and mixtures thereof.

In one embodiment, the binder is povidone K30 or K29/32, especially Plasdone™ K29/32 from ISP. The binder may be present in an amount of 0 to 80%, 0 to 70%, 0 to 60%, 0 to 50%, 0 to 40%, 0 to 30%, 0 to 25%, 0 to 20%, 0 to 15%, 0 to 10%, or from 1 to 9% of binder based on the total weight of the immediate release coating. In an embodiment, the binder is present in an amount of 5% based on the total weight of the immediate release coating. In one embodiment, the amount of binder is 5% of binder over the total mass of gamma-hydroxybutyrate and binder.

The layer deposited on the core can represent at least 10% by weight, and even greater than 20, 25, 30, 35, 40, 45, 50, 55, 60, 65, 70, 75, 80, 85 or 90% by weight of the total weight of the immediate release particle of gamma-hydroxybutyrate. In one embodiment, the layer deposited on the core represents about 85% of the weight of the immediate release particle of gamma-hydroxybutyrate.

According to an embodiment, the immediate-release particles comprise 80.75% w/w of gamma-hydroxybutyrate, 4.25% w/w of Povidone K30 and 15% of microcrystalline cellulose spheres.

According to another embodiment, the immediate-release particles comprise 80.75% w/w of gamma-hydroxybutyrate, 4.25% w/w of Povidone K30 and 15% of microcrystalline cellulose spheres with a volume mean diameter of about 95 microns to about 450 microns.

According to yet another embodiment, the immediate-release particles comprise 80.75% w/w of gamma-hydroxybutyrate, 4.25% w/w of Povidone K30 and 15% of microcrystalline cellulose spheres with a volume mean diameter of about 95 microns to about 170 microns.

According to an embodiment, the immediate-release particles comprise 80.75% w/w of sodium oxybate, 4.25% w/w of Povidone K30 and 15% of microcrystalline cellulose spheres.

According to another embodiment, the immediate-release particles comprise 80.75% w/w of potassium salt of gamma-hydroxybutyric acid, 4.25% w/w of Povidone K30 and 15% of microcrystalline cellulose spheres.

According to another embodiment, the immediate-release particles comprise 80.75% w/w of calcium salt of gamma-hydroxybutyric acid, 4.25% w/w of Povidone K30 and 15% of microcrystalline cellulose spheres.

According to another embodiment, the immediate-release particles comprise 80.75% w/w of magnesium salt of gamma-hydroxybutyric acid, 4.25% w/w of Povidone K30 and 15% of microcrystalline cellulose spheres.

According to another embodiment, the immediate-release particles are manufactured by dissolving the gamma-hydroxybutyrate and the Povidone K30 in a mixture of water/ethanol 40/60 w/w and spraying the resulting solution onto the surface of the microcrystalline cellulose spheres.

Other Characteristics of Modified Release Portion

The modified release portion may be any formulation that provides the desired in vitro dissolution profile of gamma-hydroxybutyrate. The modified release portion may include modified release particles, obtained by coating immediate release particles of gamma-hydroxybutyrate with a coating (or coating film) that inhibits the immediate release of the gamma-hydroxybutyrate. In one sub-embodiment the modified release portion comprises particles comprising: (a) an inert core; (b) a coating; and (c) a layer comprising the gamma hydroxybutyrate interposed between the core and the coating.

In an embodiment, the modified release portion comprises a time-dependent release mechanism and a pH-dependent release mechanism.

In an embodiment, the coating film comprises at least one polymer carrying free carboxylic groups, and at least one hydrophobic compound characterized by a melting point equal or greater than 40° C.

The polymer carrying free carboxylic groups may be selected from: (meth)acrylic acid/alkyl (meth)acrylate copolymers or methacrylic acid and methylmethacrylate copolymers or methacrylic acid and ethyl acrylate copolymers or methacrylic acid copolymers type A, B or C, cellulose derivatives carrying free carboxylic groups, cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate and mixtures thereof.

In an embodiment, the methacrylic acid copolymers are chosen from the group consisting of poly (methacrylic acid, methyl methacrylate) 1:1 or Eudragit™ L100 or equivalent, poly (methacrylic acid, ethyl acrylate) 1:1 or Eudragit™ L100-55 or equivalent and poly (methacrylic acid, methyl methacrylate) 1:2 or Eudragit™ S100 or equivalent.

In another embodiment the coating comprises a polymer carrying free carboxylic groups wherein the free carboxylic groups are substantially ionized at pH 7.5.

The hydrophobic compound with a melting point equal or greater than 40° C. may be selected from the group consisting of hydrogenated vegetable oils, vegetable waxes, wax yellow, wax white, wax microcrystalline, lanolin, anhydrous milk fat, hard fat suppository base, lauroyl macrogol glycerides, polyglyceryl diisostearate, diesters or triesters of glycerol with a fatty acid, and mixtures thereof.

In various embodiments, the hydrophobic compound with a melting point equal or greater than 40° C. is chosen from the group of following products: hydrogenated cottonseed oil, hydrogenated soybean oil, hydrogenated palm oil, glyceryl behenate, hydrogenated castor oil, candelilla wax, tristearin, tripalmitin, trimyristin, yellow wax, hard fat or fat that is useful as suppository bases, anhydrous dairy fats, lanolin, glyceryl palmitostearate, glyceryl stearate, lauryl macrogol glycerides, polyglyceryl diisostearate, diethylene glycol monostearate, ethylene glycol monostearate, omega 3 fatty acids, and mixtures thereof. For example, the hydrophobic compound may include hydrogenated cottonseed oil, hydrogenated soybean oil, hydrogenated palm oil, glyceryl behenate, hydrogenated castor oil, candelilla wax, tristearin, tripalmitin, trimyristin, beeswax, hydrogenated poly-1 decene, carnauba wax, and mixtures thereof.

In practice, and without this being limiting, the hydrophobic compound with a melting point equal or greater than 40° C. may be chosen from the group of products sold under the following trademarks: Dynasan™, Cutina™, Hydrobase™, Dub™, Castorwax™, Croduret™, Compritol™, Sterotex™, Lubritab™, Apifil™ Akofine™, Softisan™, Hydrocote™, Livopol™, Super Hartolan™, MGLA™, Corona™, Protalan™, Akosoft™, Akosol™, Cremao™, Massupol™, Novata™, Suppocire™, Wecobee™, Witepsol™, Lanolin™, Incromega™, Estaram™, Suppoweiss™, Gelucire™, Precirol™, Emulcire™, Plurol diisostéarique™, Geleol™, Hydrine™, Monthyle™, Kahlwax™ and mixtures thereof. In an embodiment, the hydrophobic compound with a melting point equal or greater than 40° C. may be chosen from the group of products sold under the following trademarks: Dynasan™ P60, Dynasan™ 114, Dynasan™116, Dynasan™118, Cutina™ HR, Hydrobase™ 66-68, Dub™ HPH, Compritol™ 888, Sterotex™ NF, Sterotex™ K, Lubritab™, and mixtures thereof.

A particularly suitable coating is composed of a mixture of hydrogenated vegetable oil and a methacrylic acid copolymer. The exact structure and amount of each component, and the amount of coating applied to the particle, controls the release rate and release triggers. Eudragit® methacrylic acid copolymers, namely the methacrylic acid-methyl methacrylate copolymers and the methacrylic acid-ethyl acrylate copolymers, have a pH-dependent solubility: typically, the pH triggering the release of the active ingredient from the microparticles is set by the choice and mixture of appropriate Eudragit® polymers. In the case of gamma hydroxybutyrate modified release microparticles, the theoretical pH triggering the release is from 5.5 to 6.97 or from 5.5 to 6.9. By "pH trigger" is meant the minimum pH above which dissolution of the polymer occurs.

In a particular embodiment, the coating comprises a hydrophobic compound with a melting point equal or greater than 40° C. and a polymer carrying free carboxylic groups are present in a weight ratio from 0.4 to 4, from 0.5 to 4, from 0.6 to 2.5, from 0.67 to 2.5, from 0.6 to 2.33, or from 0.67 to 2.33. In one embodiment, the weight ratio is about 1.5.

A particularly suitable coating is composed of a mixture of hydrogenated vegetable oil and a methacrylic acid copolymer with a theoretical pH triggering the release from 6.5 up to 6.97 in a weight ratio from 0.4 to 4, from 0.5 to 4, from 0.6 to 2.5, from 0.67 to 2.5, from 0.6 to 2.33, or from 0.67 to 2.33. In one embodiment, the weight ratio may be about 1.5.

The modified release particles of gamma-hydroxybutyrate have a volume mean diameter of from 100 to 1200 microns, from 100 to 500 microns, or from 200 to 800 microns. In one embodiment, the modified release particles of gamma-hydroxybutyrate have a volume mean diameter of about 320 microns.

The coating can represent 10 to 50%, 15 to 45%, 20 to 40%, or 25 to 35% by weight of the total weight of the coated modified release particles. In one embodiment, the coating represents 25-30% by weight of the total weight of the modified release particles of gamma-hydroxybutyrate.

In an embodiment, the coating layer of the modified release particles of gamma-hydroxybutyrate is obtained by spraying, in particular in a fluidized bed apparatus, a solution, suspension or dispersion comprising the coating composition as defined previously onto the immediate release particles of gamma-hydroxybutyrate, in particular the immediate release particles of gamma-hydroxybutyrate as previously described. In one embodiment, the coating is formed by spraying in a fluidized bed equipped with a Wurster or partition tube and according to an upward spray orientation or bottom spray a solution of the coating excipients in hot isopropyl alcohol.

According to an embodiment, the modified release particles of gamma-hydroxybutyrate consist of 10.5% w/w of microcrystalline cellulose spheres with a volume mean diameter of about 95 microns to about 450 microns, layered with 56.5% w/w of gamma-hydroxybutyrate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of gamma-hydroxybutyrate.

According to an embodiment, the modified release particles of gamma-hydroxybutyrate consist of 10.5% w/w of microcrystalline cellulose spheres with a volume mean diameter of about 95 microns to about 170 microns, layered with 56.5% w/w of gamma-hydroxybutyrate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of gamma-hydroxybutyrate.

According to an embodiment, the modified release particles of gamma-hydroxybutyrate consist of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of sodium oxybate.

According to an embodiment, the modified release particles of gamma-hydroxybutyrate consist of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of sodium oxybate.

According to another embodiment, the modified release particles of gamma-hydroxybutyrate consist of 11.3% w/w of microcrystalline cellulose spheres with a volume mean diameter of about 95 microns to about 450 microns, layered with 60.5% w/w of gamma-hydroxybutyrate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

According to another embodiment, the modified release particles of gamma-hydroxybutyrate consist of 11.3% w/w of microcrystalline cellulose spheres with a volume mean diameter of about 95 microns to about 170 microns, layered with 60.5% w/w of gamma-hydroxybutyrate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

According to another embodiment, the modified release particles of gamma-hydroxybutyrate consist of 11.3% w/w of microcrystalline cellulose spheres with a volume mean diameter of about 95 microns to about 450 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

According to another embodiment, the modified release particles of gamma-hydroxybutyrate consist of 11.3% w/w of microcrystalline cellulose spheres with a volume mean diameter of about 95 microns to about 170 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

Packaging

The composition of gamma-hydroxybutyrate may be supplied in sachets or stick-packs comprising a particulate formulation. The sachets may be available in several different doses, comprising gamma-hydroxybutyrate in amounts equivalents to 0.5 g, 1.0 g, 1.5 g, 3.0 g, 4.5 g, 6.0 g, 7.5 g, 9.0 g, 10.5 g and/or 12 g of sodium oxybate. Depending on the dose required, one or more of these sachets may be opened, and its contents mixed with tap water to provide the nightly dose of gamma-hydroxybutyrate.

Methods of Treatment

Further provided herein is a method of treating a disorder treatable with gamma-hydroxybutyrate in a human subject in need thereof comprising orally administering, less than two hours after eating, a single bedtime daily dose to said human amounts of gamma-hydroxybutyrate equivalent to from 3.0 to 12.0 g of sodium oxybate in the composition. Further provided herein are methods of treating narcolepsy, types 1 and/or 2, by orally administering at bedtime a therapeutically effective amount of a gamma-hydroxybutyrate formulation characterized by the novel gamma-hydroxybutyrate pharmacokinetic properties of the composition when administered less than two hours after eating. In an embodiment, the composition of the present invention is effective to treat narcolepsy Type 1 or Type 2, wherein the treatment of narcolepsy is defined as reducing excessive daytime sleepiness or reducing the frequency of cataplectic attacks. The therapeutically effective amount may include equivalents from 3.0 to 12.0 g of sodium oxybate. In various embodiments, the therapeutically effective amount is 4.5, 6.0, 7.5 or 9.0 g of sodium oxybate. In one embodiment, the therapeutically effective amount is 6 g or 9 g of sodium oxybate. In various embodiments, the formulation includes sodium oxybate present in a unit dose of at least 4.5 g, at least 6.0 g, at least 7.5 g, or at least 9.0 g. The effectiveness of the treatment may be measured by one or any combination of the following criteria:

Increase the mean sleep latency, as determined on the Maintenance of Wakefulness Test (MWT).

Improve the Clinical Global Impression (CGI) rating of sleepiness.

Decrease the number of cataplexy attacks (NCA) determined from the cataplexy frequency item in the Sleep and Symptoms Daily Diary Decrease the disturbed nocturnal sleep (DNS), the disturbed nocturnal events or the adverse respiratory events as determined by polysomnographic (PSG) measures of sleep fragmentation Decrease the excessive daytime sleepiness (EDS) as measured by patient report via the Epworth Sleepiness Scale (ESS).

Decrease the daytime sleepiness as measured by the Maintenance of Wakefulness Test based on EEG measures of wakefulness.

Decrease PSG transitions from N/2 to N/3 and REM sleep to wake and N1 sleep (as determined by C Iber, S Ancoli-Israel, A Chesson, S F Quan. *The AASM Manual for the Scoring of Sleep and Associated Events*. Westchester, IL: American Academy of Sleep Medicine; 2007).

Decrease the number of arousals or wakenings, obtained from a PSG as defined by the American Academy of Sleep Medicine.

Improve the sleep quality, obtained from one or more of (i) the Sleep and Symptom Daily Diary, (ii) Visual Analog Scale (VAS) for sleep quality and sleep diary, and (iii) VAS for the refreshing nature of sleep Decrease the Hypnagogic Hallucinations (HH) or sleep paralysis (SP) symptoms in NT1 narcolepsy patients, as measured by the Sleep and Symptom Daily Diary In an embodiment, the treatment using the composition administered less than two hours after eating is superior, as measured by any one or combination of the foregoing criteria, to an equal dose administered twice nightly of an immediate release liquid solution of sodium oxybate, with the second dose administered 4 hours after the first dose.

The invention further provides a method of treatment of narcolepsy Type 1 or Type 2 wherein, compared to a dosing regimen consisting of administering half the dose at t0 and another half of the dose at $t_{4h}$ of an immediate release liquid solution of sodium oxybate, a single bedtime daily dose administration of a therapeutically effective amount of the formulation of the invention has been shown to produce less confusion, less depressive syndrome, less incontinence, less nausea or less sleepwalking.

EXAMPLES

Example 1. Formulations

Figure 1B:
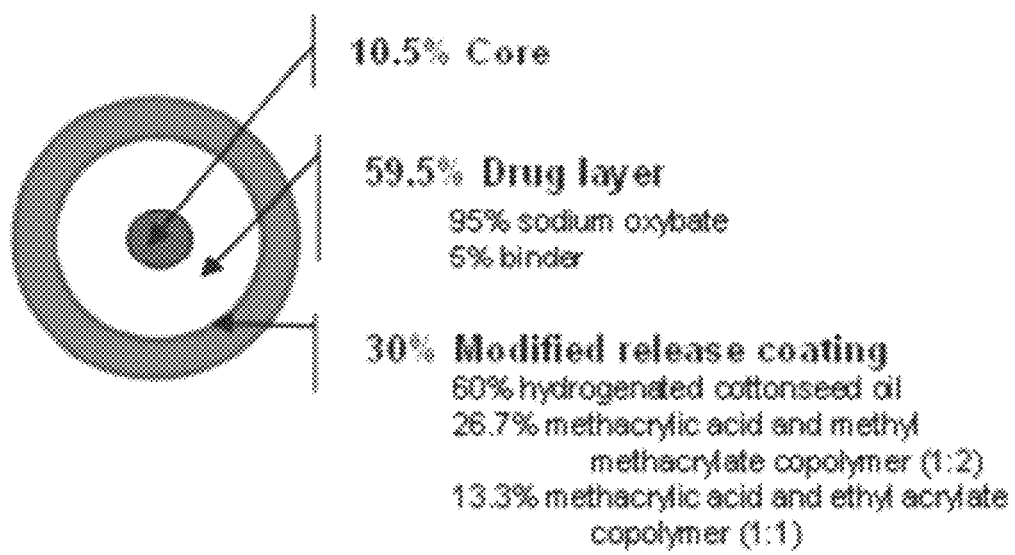
FIG. 1B depicts the qualitative and quantitative structure of the modified release (MR) microparticles of gamma-hydroxybutyrate of Example 1.

Tables 1a-1d provide the qualitative and quantitative compositions of sodium oxybate IR microparticles, MR microparticles, and mixtures of IR and MR microparticles. The physical structure of the microparticles showing the qualitative and quantitative composition of the IR and MR microparticles is depicted in FIG. 1.

Briefly, sodium oxybate immediate release (IR) microparticles were prepared as follows: 1615.0 g of sodium oxybate and 85.0 g of polyvinylpyrrolidone (Povidone K30-Plasdone™ K29/32 from ISP) were solubilized in 1894.3 g of absolute ethyl alcohol and 1262.9 g of water. The solution was entirely sprayed onto 300 g of microcrystalline cellulose spheres (Cellets™ 127) in a fluid bed spray coater apparatus. IR Microparticles with volume mean diameter of about 270 microns were obtained.

Sodium oxybate modified release (MR) microparticles were prepared as follows: 22.8 g of methacrylic acid copolymer Type C (Eudragit™ L100-55), 45.8 g of methacrylic acid copolymer Type B (Eudragit™ S100), 102.9 g of hydrogenated cottonseed oil (Lubritab™), were dissolved in 1542.9 g of isopropanol at 78° C. The solution was sprayed entirely onto 400.0 g of the sodium oxybate IR microparticles described above in a fluid bed spray coater apparatus with an inlet temperature of 48° C., spraying rate around 11 g per min and atomization pressure of 1.3 bar. MR microparticles were dried for two hours with inlet temperature set to 56° C. MR microparticles with mean volume diameter of about 320 microns were obtained.

The finished composition, which contains a 50:50 mixture of MR and IR microparticles calculated on their sodium oxybate content, was prepared as follows: 353.36 g of the above IR microparticles, 504.80 g of the above MR microparticles, 14.27 g of malic acid (D/L malic acid), 6.34 g of xanthan gum (Xantural™ 75 from Kelco), 9.51 g of carrageenan gum (Viscarin™ PH209 from FMC Biopolymer), 9.51 g of hydroxyethylcellulose (Natrosol™ 250M from Ashland) and 4.51 g of magnesium stearate were mixed. Individual samples of 7.11 g (corresponding to a 4.5 g dose of sodium oxybate with half of the dose as immediate-release fraction and half of the dose as modified release fraction) were weighed.

TABLE 1a

Composition of IR Microparticles

| Component | Function | Quantity per 2.25 g dose (g) |
|---|---|---|
| Sodium oxybate | Drug substance | 2.25 |
| Microcrystalline cellulose spheres | Core | 0.418 |
| Povidone K30 | Binder and excipient in diffusion coating | 0.118 |
| Ethyl alcohol | Solvent | Eliminated during processing |
| Purified water | Solvent | Eliminated during processing |
| Total | | 2.786 |

TABLE 1b

Composition of MR Microparticles

| Component | Function | Quantity per 4.5 g dose (g) |
|---|---|---|
| IR Microparticles | Core of MR microparticles | 2.786 |
| Hydrogenated Vegetable Oil | Coating excipient | 0.716 |
| Methacrylic acid Copolymer Type C | Coating excipient | 0.159 |
| Methacrylic acid Copolymer Type B | Coating excipient | 0.318 |
| Isopropyl alcohol | Solvent | Eliminated during processing |
| Total | | 3.981 |

TABLE 1c

Qualitative Finished Composition

| Component | Function | Quantity per 4.5 g dose (g) |
|---|---|---|
| MR microparticles | Modified release fraction of sodium oxybate | 3.981 |
| IR microparticles | Immediate release fraction of sodium oxybate | 2.786 |
| Malic acid | Acidifying agent | 0.113 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.036 |
| Total | | 7.116 |

TABLE 1d

Quantitative finished composition

| Component | Function | Quantity per 4.5 g dose (g) |
|---|---|---|
| Sodium oxybate | Drug substance | 4.5 |
| Microcrystalline cellulose spheres | Core | 0.836 |
| Povidone K30 | Binder | 0.237 |
| Hydrogenated Vegetable Oil | Coating excipient | 0.716 |
| Methacrylic acid Copolymer Type C | Coating excipient | 0.159 |
| Methacrylic acid Copolymer Type B | Coating excipient | 0.318 |
| Malic acid | Acidifying agent | 0.113 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.036 |
| Total | | 7.116 |

Example 1bis. Alternative Formulation

An alternative formulation to the formulation described in Example 1 is described in Example 1bis.

Sodium oxybate immediate release (IR) microparticles were prepared by coating the IR microparticles described in Example 1 with a top coat layer. Microparticles were prepared as follows: 170.0 of hydroxypropyl cellulose (Klucel™ EF Pharm from Hercules) were solubilized in 4080.0 g of acetone. The solution was entirely sprayed onto 1530.0 g of the IR microparticles of Example 1 in a fluid bed spray coater apparatus. IR Microparticles with volume mean diameter of about 298 microns were obtained (see Table 1bis-a).

Sodium oxybate modified release (MR) microparticles were prepared as described in example 1 (see Table 1b).

The finished composition, which contains a 50:50 mixture of MR and IR microparticles based on their sodium oxybate content, was prepared as follows: 412.22 g of the above IR microparticles, 530.00 g of the above MR microparticles, 29.96 g of malic acid (D/L malic acid), 4.96 g of xanthan gum (Xantural™ 75 from Kelco), 4.96 g of colloidal silicon dioxide (Aerosil™ 200 from Degussa) and 9.92 g of magnesium stearate were mixed. Individual samples of 7.45 g (corresponding to a 4.5 g dose of sodium oxybate with half of the dose in an immediate-release fraction and half of the dose in a modified release fraction) were weighed (see Table 1bis-b and 1bis-c).

TABLE 1bis-a

Composition of IR Microparticles

| Component | Function | Quantity per 2.25 g dose (g) |
|---|---|---|
| Sodium oxybate | Drug substance | 2.25 |
| Microcrystalline cellulose spheres | Core | 0.418 |
| Povidone K30 | Binder and excipient in diffusion coating | 0.118 |
| Hydroxypropyl cellulose | Top coat | 0.310 |
| Ethyl alcohol | Solvent | Eliminated during processing |
| Purified water | Solvent | Eliminated during processing |
| Acetone | Solvent | Eliminated during processing |
| Total | | 3.096 |

TABLE 1bis-b

Qualitative Finished Composition

| Component | Function | Quantity per 4.5 g dose (g) |
|---|---|---|
| MR microparticles | Modified release fraction of sodium oxybate | 3.981 |
| IR microparticles | Immediate release fraction of sodium oxybate | 3.096 |
| Malic acid | Acidifying agent | 0.225 |
| Xanthan gum | Suspending agent | 0.037 |
| Colloidal silicon dioxide | Gliding agent | 0.037 |
| Magnesium stearate | Lubricant | 0.075 |
| Total | | 7.451 |

TABLE 1bis-c

Quantitative finished composition

| Component | Function | Quantity per 4.5 g dose (g) |
|---|---|---|
| Sodium oxybate | Drug substance | 4.5 |
| Microcrystalline cellulose spheres | Core | 0.836 |
| Povidone K30 | Binder | 0.237 |
| Hydroxypropyl cellulose | Top coat | 0.310 |
| Hydrogenated Vegetable Oil | Coating excipient | 0.716 |
| Methacrylic acid Copolymer Type C | Coating excipient | 0.159 |
| Methacrylic acid Copolymer Type B | Coating excipient | 0.318 |
| Malic acid | Acidifying agent | 0.225 |
| Xanthan gum | Suspending agent | 0.037 |
| Colloidal silicon dioxide | Gliding agent | 0.037 |
| Magnesium stearate | Lubricant | 0.075 |
| Total | | 7.451 |

Compared to the finished composition described in Example 1, this alternative composition has the following characteristics: same MR microparticles, same IR microparticles but with a top coat, increased amount of malic acid, only one suspending agent (xanthan gum) and presence of a glidant.

Example 2. In Vivo Pharmacokinetic Study of Finished Composition According to Example 1 (6 g FT218 in Fed and Fasted State)

Figure 2B:
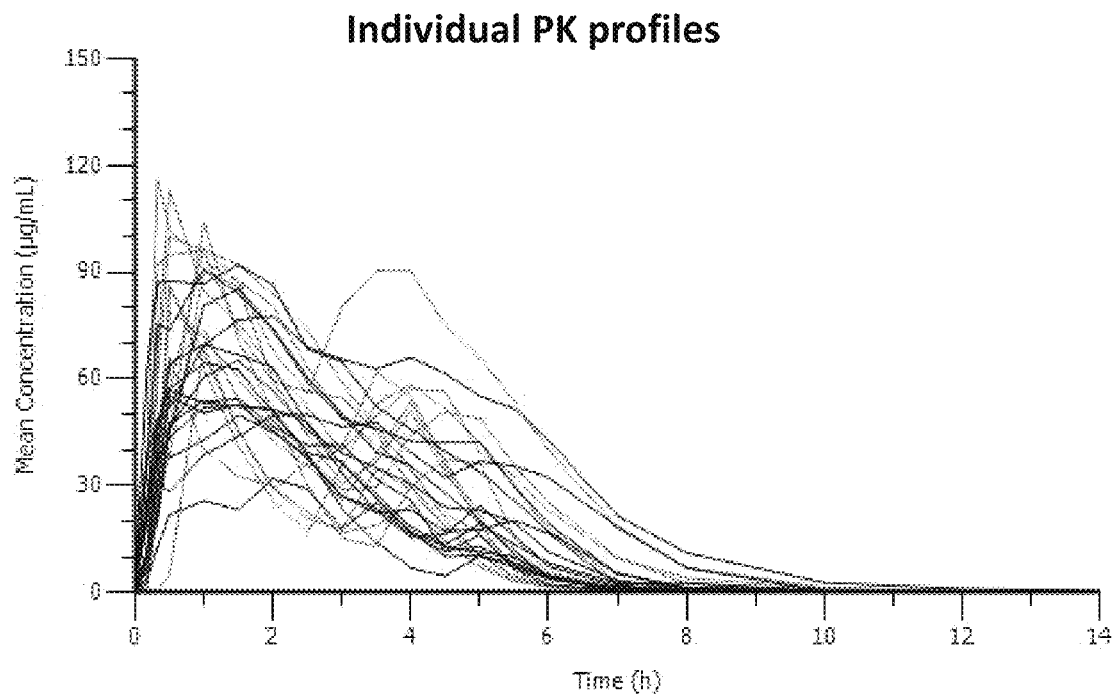
FIG. 2B is a series of individual profiles in a mean concentration versus time curve for 6 g FT218 administered in the fed and fasted state.

Pharmacokinetic testing was undertaken in vivo in healthy human volunteers. A test product with the finished composition of Example 1 (FT218) and manufactured at larger scale was administered as a 6 g dose. FT218 was administered to 16 healthy volunteers and a first group of n=14 was administered FT218 in the fed state and a second group of n=13 was administered FT218 in the fasted state. The tested samples were manufactured as described in Table 1c for 4.5 g and quantities were hypothetically adjusted to a 6 g dose. The concentration versus time curve of FT218 in the fed and fasted state are presented in FIGS. 2A and 2B. The derived PK parameters are summarized below in Table 2 and Table 3 provides the % ratio of geometric means between the fed and fasted states. FIG. 2A and Table 3 show a $C_{max}$ (fed)/$C_{max}$ (fasted)=66.7% and an AUC (fed)/AUC (fasted)=86% for FT218. Therefore, the AUC falls within the 80-125% bioequivalence range with no effect boundaries, so food should have no impact on total exposure of the composition. It appears that food may have no or low impact on MR microparticle absorption in the latter part of the gastrointestinal tract.

TABLE 2

| | | | | Mean PK Parameters | | | | |
|---|---|---|---|---|---|---|---|---|
| Arm | Tmax (h) [min-max] | Cmax (µg/mL) ± SD (CV) | $AUC_{0-last}$ (µg/mL · h) ± SD (CV) | $AUC_{0-inf}$ (µg/mL · h) ± SD (CV) | $AUC_{0-8\,h}$ (µg/mL · h) ± SD (CV) | C8 h (µg/mL) ± SD (CV) | $T_{1/2}$ (h) ± SD (CV) | Az (/h) ± SD (CV) |
| FT218 fed n = 14 | 1.5 [0.5-2.5] | 64.0 ± 17.5 (27.3) | 241 ± 88.1 (36.5) | 242 ± 88.2 (36.5) | 239 ± 85.0 (35.5) | 2.09 ± 3.14 (150.5) | 0.71 ± 0.25 (34.5) | 1.07 ± 0.305 (28.5) |
| FT218 fasted n = 13 | 0.53 [0.33-1] | 90.5 ± 15.8 (17.5) | 267 ± 85.2 (31.9) | 267 ± 85.2 (32) | 266 ± 82.9 (31.2) | 1.43 ± 2.04 (142.7) | | |

TABLE 3

Food Effect on FT218

| | PE (fed/fasted) | 90% CI |
|---|---|---|
| $C_{max}$ | 66.7 | 58.2-76.5 |
| $AUC_{0-last}$ | 86.0 | 79.9-92.6 |
| $AUC_{0-inf}$ | 86.1 | 80.0-92.7 |

Example 3. Simulated Data to Demonstrate the Food Effect on the IR Portion, MR Portion, and FT218 in the Fed and Fasted State To illustrate the effect of food on FT218 and the IR and MR portions of FT218 for a 9 g dosage, concentration versus time curves were simulated. FIG. 3A shows the predicted negative effect of food on the IR portion of microparticles alone at a single 3 g dose. FIG. 3A shows a $C_{max}$ (fed)/$C_{max}$ (fasted)=40% and AUC (fed)/AUC (fasted)=70%. Food appears to have a similar impact on the IR microparticles of FT218 as on Xyrem®, as seen when comparing FIGS. 3A and 4A which shows concentration versus time curves for Xyrem in the fed and fasted state.

FIG. 3B shows that the predicted negative food effect is reduced in the MR portion of microparticles and in the full FT218 formulation as compared to the IR portion of microparticles. FIG. 3B shows a $C_{max}$ (fed)/$C_{max}$ (fasted)=55% and an AUC (fed)/AUC (fasted)=80% for FT218. Therefore, it appears that food may have no or low impact on MR microparticle absorption in the latter part of the gastrointestinal tract.

Example 4. Comparison of Xyrem® and FT218 in the Fed, 2 hr Post Meal, and Fasted State The effect of food on FT218 and Xyrem® is shown in FIGS. 4A and 4B. Data was digitized from the NDA dossier of Xyrem 21-196. FIG. 4A shows a concentration versus time curve for a 4.5 g single dose of Xyrem® in the fed state, the fasted state and 2 hours post meal. FIG. 4B shows a concentration versus time curve for a 6 g dose of FT218 in the fed state, the fasted state and 2 hours post meal. For Xyrem®, $C_{max}$ and AUCs decrease as meal time is closer to administration, while $T_{max}$ increases with food. In comparison, FT218 appears to demonstrate the same behavior as Xyrem®, but the impact of meal time seems reduced. Fed and 2 h post meal administration appear to have similar PK profiles (inter-study comparison). The derived PK parameters are summarized below (Table 4).

TABLE 4

Mean PK Parameters

| | Xyrem® (4.5 g) | | | FT218 (6 g) | | |
|---|---|---|---|---|---|---|
| | fast | 2 h post meal[a] | fed | fast | 2 h post meal | fed |
| $T_{max}$ (h) | 0.75 | 1.25-1.14 | 2 | 0.53 [0.33-1] | 1.5 [0.33-3.5] | 1.5 [0.5-2.5] |
| $C_{max}$ | 142 ± 34.2 | 88.9-83.0 | 60.1 ± 20.1 | 90.5 ± 15.8 | 64.6 ± 25.8 | 64.0 ± 17.5 |
| $AUC_{0-inf}$ (µg/mL · h) | 289 ± 109 | 241-233 | 188 ± 80 | 267 ± 85.2 | 273 ± 139 | 242 ± 88.2 |

[a]means of study OMC-SXB-8 are presented.

Example 5. Comparison of Xyrem® and FT218 in the Fed, 2 hr Post Meal, and Fasted State To compare the effect of food on FT218 and Xyrem® in the fed state, 2 hours post-meal, and in the fasted state, the concentration versus time curves for a 3 g dose of Xyrem® administered twice and a single 6 g dose of FT218 were plotted together.

FIG. 5A shows expected concentration versus time curves for Xyrem® and FT218 in the fed state. Xyrem® in the fed state was extrapolated based on 4.5 g data from the NDA review of Xyrem® (study OMC-SXB-11) (linearized to the dose of 3 g and multiplied by a factor of correction of 0.7). As seen in FIG. 5A, Xyrem® risks of lack of efficacy during the first dosing, while the onset of efficacy is sooner for FT218 than Xyrem® and the $C_{max}$ of FT218 is below the $C_{max}$ for the 2nd peak of Xyrem®. Therefore, administering FT218 in the fed state may reduce safety concerns associated with administering Xyrem® in the fed state.

Figure 5B:
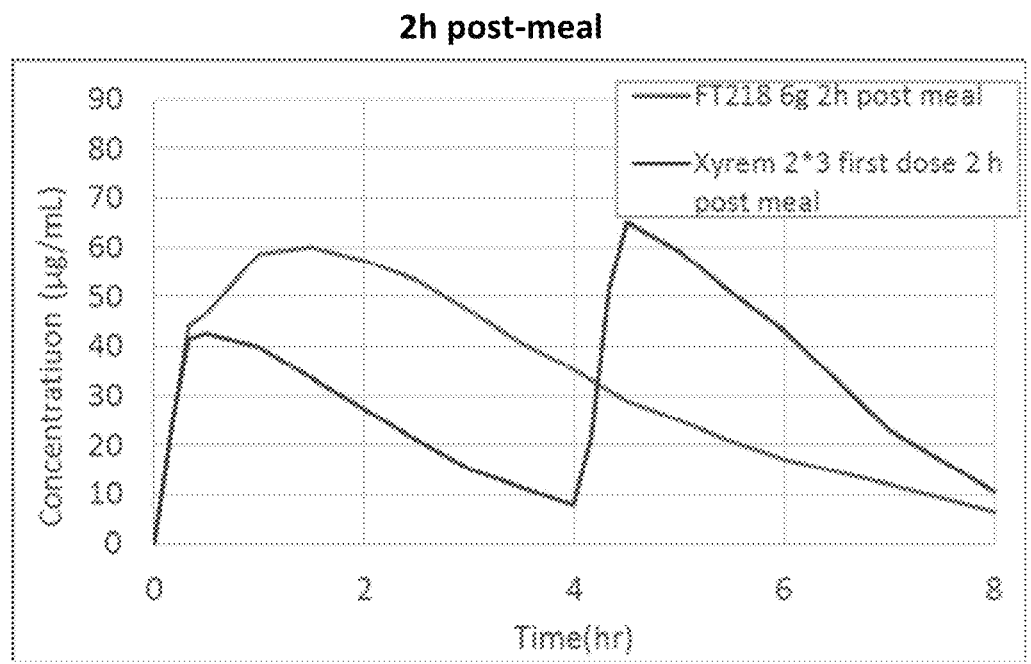
FIG. 5B shows expected concentration versus time curves for two 3 g doses of Xyrem® and one 6 g does of FT218 administered two hours post-meal.

FIG. 5B shows expected concentration versus time curves for Xyrem® and FT218 administered two hours post-meal. The Xyrem® data is extrapolated from the PK FT218-1602 BA study. This study was a randomized, 2 treatments, 2 periods, 2 sequences cross-over study. The two treatments were: FT218 6 g administered 2 hours post evening meal and 2*3 Xyrem first dose administered 2 hours post evening meal, the $2^{nd}$ dose was administered 4 hours after the first dose. 28 subjects were included.

Figure 5C:
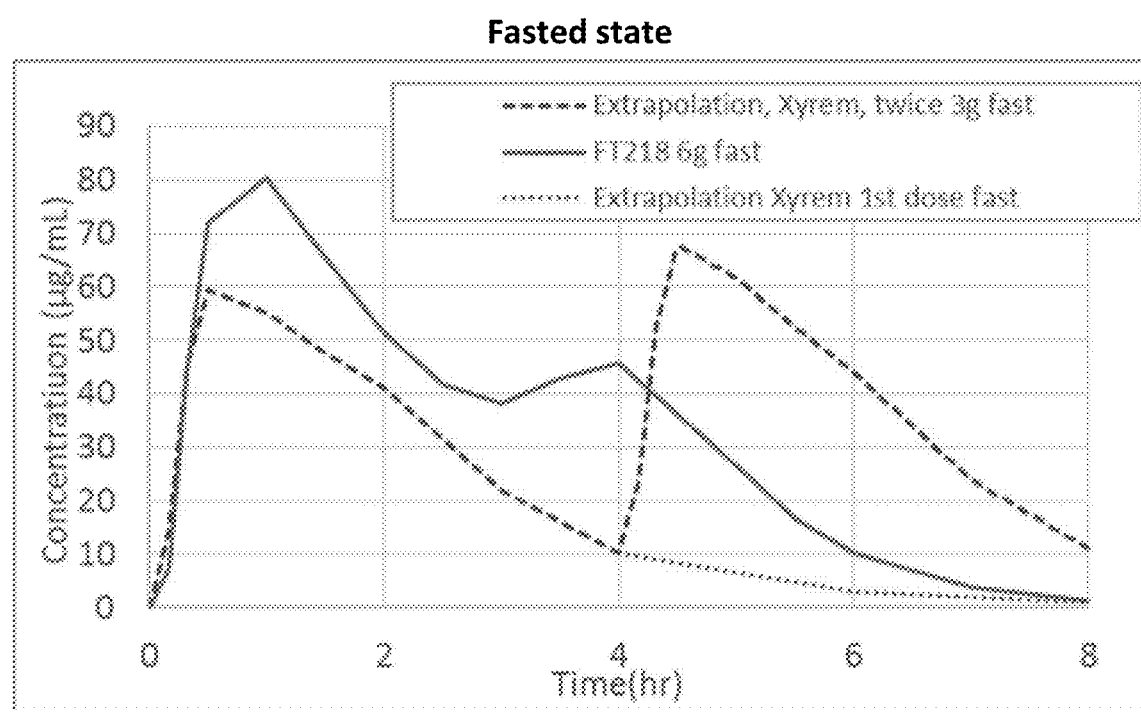
FIG. 5C shows expected concentration versus time curves for two 3 g doses of Xyrem® and one 6 g dose of FT218 administered in the fasted state.

As seen in FIG. 5B, the $C_{max}$ of FT218 is between the $C_{max}$ of the first peak and the $C_{max}$ of the second peak of Xyrem®. Therefore, administering FT218 at two hours post-meal may reduce safety concerns associated with Xyrem®. FIG. 5C shows expected concentration versus time curves for Xyrem® and FT218 administered in the fasted state. The Xyrem® data was simulated using numerical superposition.

The impact of the food effect of FT218 is likely reduced on $C_{max}$ and AUCs compared to Xyrem® at the same dose based on food effect and dose proportionality data. The predictability of FT218 may be better than Xyrem®. Table 5 provides expected PK parameters for Xyrem® (2×3 g dose) and FT218 (6 g dose) in the fed state, two hours post-meal, and in the fasted state.

TABLE 5

Estimated PK Parameters

| | Tmax (hr) | | Cmax $1^{st}$ peak | | Cmax $2^{nd}$ peak | AUC0-inf | |
|---|---|---|---|---|---|---|---|
| | Xyrem | FT218 | Xyrem | FT218 | Xyrem | Xyrem | FT218 |
| Fed | >0.5 | 1.50 | <46.4 | 64.0 | ~70.9 | <259 | 242 |
| 2 h post meal | 0.5 | 1.50 | 46.4 | 64.6 | 70.9 | 259 | 273 |
| Fast | <0.5 | 0.53 | >46.4 | 90.5 | ~70.9 | >259 | 267 |

Example 6. Comparison of Xyrem® and FT218 in the Fed, 2 hr Post Meal, and Fasted State To compare the anticipated effect of food on FT218 and Xyrem® in the fed state, 2 hours post-meal, and in the fasted state, the concentration versus time curves for a 4.5 g dose of Xyrem® administered twice and a single 9 g dose of FT218 were plotted together.

FIG. 6A shows expected concentration versus time curves for Xyrem® and FT218 in the fed state. The FT218 data is from a dose proportionality study and the Xyrem® data is from the NDA dossier of Xyrem®.

The FT218 mean concentration-time profile is the observed data of the dose proportionality study at 9 g 2 hours post-meal. As seen in FIG. 6A, Xyrem® risks of lack of efficacy during the first dosing, while the onset of efficacy is sooner for FT218 than Xyrem® and the $C_{max}$ of FT218 is below the $C_{max}$ for the 2nd peak of Xyrem®. Therefore, administering FT218 in the fed state may reduce safety concerns associated with administering Xyrem® in the fed state.

Figure 6B:
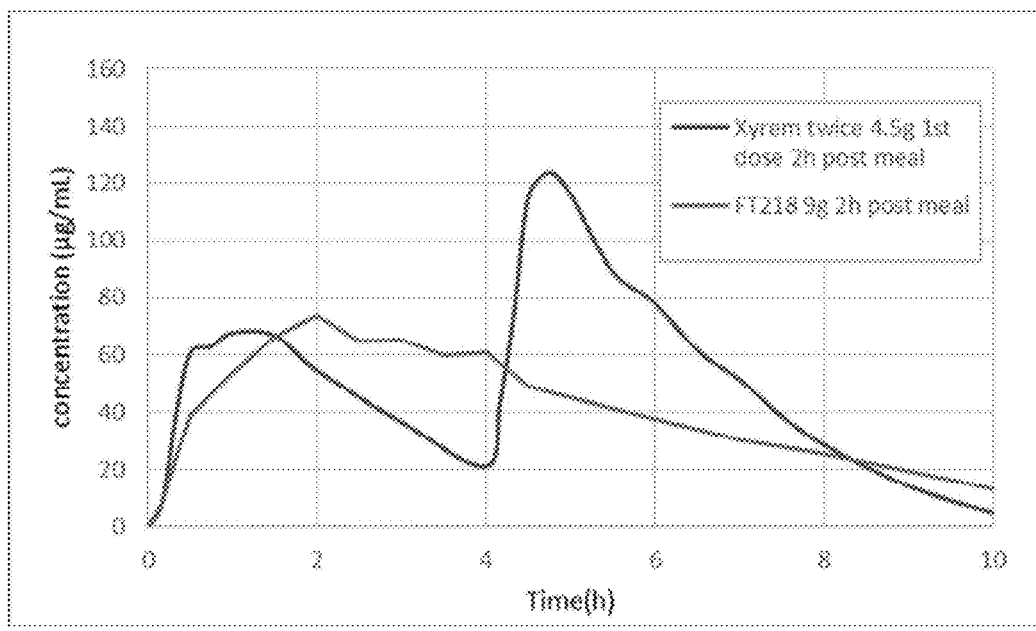
FIG. 6B shows expected concentration versus time curves for two 4.5 g doses of Xyrem® and one 9 g dose of FT218 administered two hours post-meal.
Figure 6C:
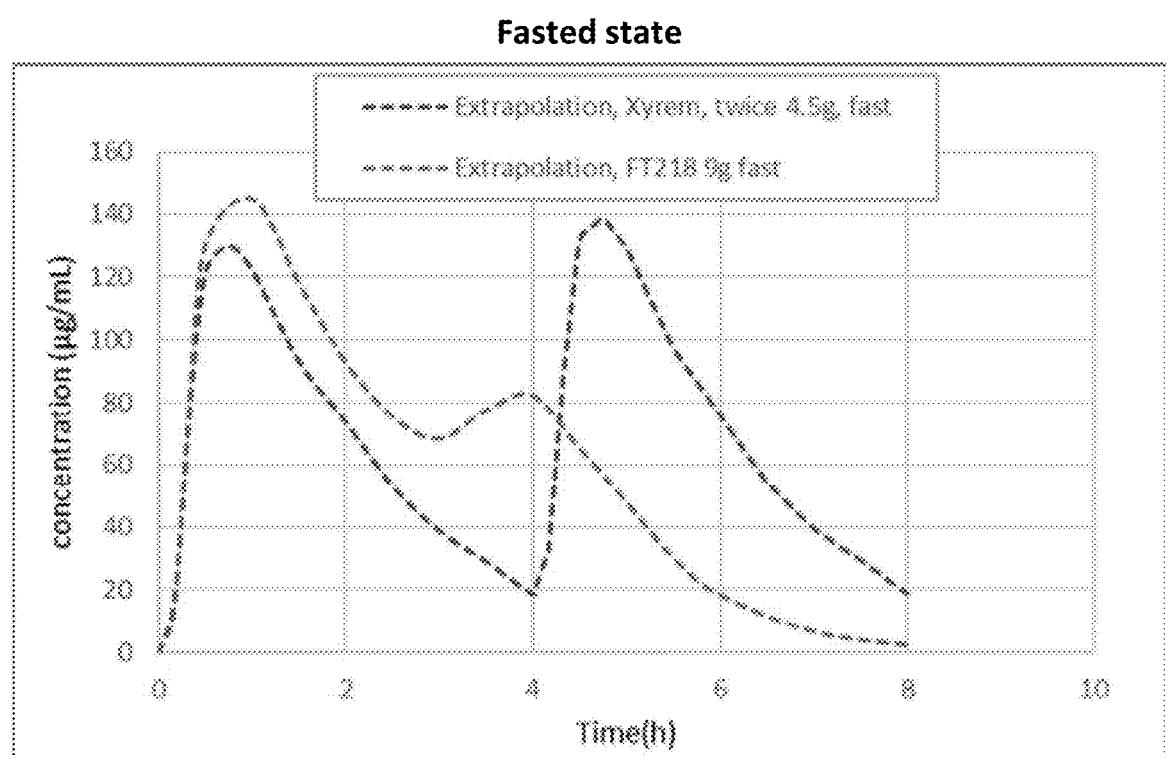
FIG. 6C shows expected concentration versus time curves for two 4.5 g doses of Xyrem® and one 9 g dose of FT218 administered in the fasted state.

FIG. 6B shows expected concentration versus time curves for Xyrem® and FT218 administered two hours post-meal. As seen in FIG. 6B, the $C_{max}$ of FT218 is between the $C_{max}$ of the first peak and the $C_{max}$ of the second peak of Xyrem®. Therefore, administering FT218 at two hours post-meal may reduce safety concerns associated with Xyrem®. FIG. 6C shows expected concentration versus time curves for Xyrem® and FT218 administered in the fasted state. The Xyrem® and FT218 fasted data was extrapolated based on 4.5 g data (dose linearity assumption and multiplied by a factor of correction of 1.2).

The impact of the food effect of FT218 is likely reduced on $C_{max}$ and AUCs compared to Xyrem® at the same dose based on food effect and dose proportionality data. The predictability of FT218 may be better than Xyrem®. Table 6 provides expected PK parameters for Xyrem® (2×4.5 g dose) and FT218 (9 g dose) in the fed state, two hours post-meal, and in the fasted state.

TABLE 6

Estimated PK Parameters

| | Tmax (hr) | | Cmax 1st peak | | Cmax 2nd peak | AUC0-inf | |
|---|---|---|---|---|---|---|---|
| | Xyrem | FT218 | Xyrem | FT218 | Xyrem | Xyrem | FT218 |
| Fed | 2 | >2 | 60.1 | <84.5 | ~142 | <518 | ~518 |
| 2 h post meal | 1.17[a] | 2 | 77.6 | 84.5 | 142 | 518 | ~518 |
| Fast | 0.75 | <2 | 142 | >84.5 | ~142 | >518 | >518 |

Example 7. Comparison of Xyrem® and FT218 PK Profiles for AUC and Cmax in the Fed State To compare the effect on dosing time, AUC and $C_{max}$ for 6 g of FT218 and Xyrem® were plotted over a period of time after eating a meal. FIG. 7A shows AUC for 6 g FT218 and 6 g Xyrem® versus time after a meal. FIG. 7B shows $C_{max}$ for 6 g FT218 and 6 g Xyrem® versus time after a meal. The PK parameters were calculated on mean PK profiles. Circulating levels for FT218 may be more consistent than Xyrem® for each individual through the night, as overall the line shape profile for FT218 is more constant (fluctuation is reduced). In addition, circulating levels of GHB may be less impacted by meal (from fed to fast state). For example, taking FT218 during a meal, 1 hour, or 2 hours post-meal may lead to similar PK profiles. This may lead to fewer constraints for patients.

Example 8. Pharmacokinetics and Dose Proportionality of FT218 for Once-Nightly Dosing To assess the PK of FT218 given as a single dose of 4.5 g, 7.5 g and 9 g, compare PK parameters at the 3 doses, and estimate the dose proportionality, an open-label, single-dose, 3-sequential period study in 20 healthy volunteers was performed. Subjects received 3 separate single-dose (without titration) administrations of FT218 at bedtime, two hours post-evening meal, in a sequential order of 4.5 g, 7.5 g and 9 g with a minimum 7-day washout between doses. Dose proportionality between the three doses was assessed using the power method. Sensitivity analyses were performed using ANOVA.

Variability of concentrations of FT218 and twice-nightly sodium oxybate IR at 8 h and 10 h post-dose (when patients typically awaken) in the PK pilot and the present study were compared in terms of standard deviation.

The study was conducted in 20 healthy volunteers (12 males and 8 females). All subjects completed periods 1 (4.5 g) and 2 (7.5 g), while 12 subjects completed period 3 (9 g).

For the 3 doses, mean pharmacokinetics exhibited similar overall profiles with median $T_{max}$ between 1.5 and 2 hours (FIG. 8). Mean $C_{max}$ increased from 42.9 to 84.5 µg/mL across the increasing doses. Following $C_{max}$, blood levels gradually decreased overnight. Mean $AUC_{inf}$ was 191, 358 and 443 µg·h/mL for the 4.5, 7.5 and 9 g doses respectively.

Mean concentrations at 8 hours were 4.8, 19.7 and 25.5 µg/mL for the 4.5, 7.5 and 9 g doses respectively.

Table 7 provides variability of concentrations at 8 h and 10 h post-dose for twice-nightly sodium oxybate and FT218 in the PK pilot and dose proportionality studies.

TABLE 7

Concentrations at 8 h and 10 h post-dose for twice-nightly sodium oxybate and FT218

| | Twice-nightly sodium oxybate IR PK pilot study | FT218 | | |
|---|---|---|---|---|
| | | PK pilot study | | Dose propor- tionality study |
| PK parameter | 2 * 2.25 g n = 15 | Part 1- Step 1 4.5 g n = 14 | Part 2 4.5 g n = 12 | 4.5 g n = 20 |
| $C_{8h}$ mean ± SD (µg/mL) | | | | |
| BQL set to missing | 9.24 ± 11.77 (n = 14) | 7.40 ± 5.88 (n = 13) | 6.27 ± 5.81 | 4.76 ± 5.0 |
| BQL set to zero | 8.62 ± 11.59 | 6.87 ± 5.98 | 6.27 ± 5.81 | 4.76 ± 5.01 |
| $C_{10h}$ mean ± SD (µg/mL) | | | | |
| BQL set to missing | 2.64 ± 3.84 (n = 8) | 1.21 ± 1.86 (n = 8) | 0.94 ± 0.55 (n = 7) | 0.73 ± 0.41 (n = 9) |
| BQL set to zero | 1.41 ± 3.04 | 0.69 ± 1.50 | 0.55 ± 0.63 | 0.33 ± 0.46 |

BQL: concentration below quantitation limit.

Mean concentrations at 8 h and 10 h post-dose for FT218 are at least as low as twice-nightly sodium oxybate IR, regardless of the rule used to handle concentrations below quantitation limit (Table 7). Moreover, the variability of the concentrations was similar.

Applying the power method, the slope estimate for $C_{max}$ was 1.02 and the confidence interval centered on 1.00 (90% CI: 0.76-1.28). For $AUC_{inf}$ the estimate was 1.34 (90% CI: 1.19-1.48), indicating that the increase in the AUC is slightly more than proportional. These results were consistent with ANOVA sensitivity analysis results.

Thirteen subjects (65%) reported a total of 31 treatment emergent adverse events (TEAEs). 8 TEAEs (mainly headache 5/8) were experienced by 7/20 (35%) subjects during the 4.5 g period. 7 TEAEs (mainly gastrointestinal disorders 4/7) were experienced by 4/20 (20%) subjects during the 7.5 g period. 16 TEAEs (mainly gastrointestinal disorders 8/16) were experienced by 6/12 (50%) subjects during the 9 g period. One of these, a nervous system disorder (sedation) was a SAE. The intensity of TEAEs was judged severe for 2/31 TEAEs (both in 9 g period), moderate for 10/31 (4 in 4.5 g period, 3 in 7.5 g period and 3 in 9 g period) and mild for 19/31. All the TEAEs were resolved before the end of the study.

FT218 achieved blood-level profiles, when given at bedtime, consistent with a single CR dose. Dose proportionality was maintained for $C_{max}$ across the dosage range. The safety profile was consistent with what is known for sodium oxybate and most AEs were mild to moderate in severity even without titration.

Example 9. TEAEs for FT218 in the Fed and Fasted State

Table 8 provides a summary of the TEAEs in the fed and fasted states for a 6 g dose of FT218.

TABLE 8

Adverse Events with FT218

| TEAE | FT218 6 g single dose Fasted (N = 16); n (%) | FT218 6 g single dose Fed (N = 15); n (%) |
|---|---|---|
| Somnolence | 13 (81.3) | 10 (66.7) |
| Dizziness | 7 (43.8) | 3 (20.0) |
| Nausea | 6 (37.5) | 1 (6.7) |
| Headache | 4 (25.0) | 2 (13.3) |
| Feeling Drunk | 4 (25.0) | 4 (26.7) |
| Vomiting | 3 (18.8) | 1 (6.7) |
| Fatigue | 3 (18.8) | 1 (6.7) |

As can be seen from Table 8, administration of 6 g FT218 in the fed state results in fewer TEAEs than 6 g FT218 administered in the fasted state.

Moreover, the pharmacokinetic-adverse event (AE) relationship for FT218 was evaluated. A total of 129 healthy volunteers received single doses of FT218 between 4.5-9 g. Six single-dose, randomized, crossover studies that assessed the pharmacokinetics of FT218 at 4.5, 6, 7.5 and 9 g in healthy volunteers were used. Lattice plots, "spaghetti" plots, and scatter plots of individual gamma hydroxybutyrate concentrations and indicators when AEs by system, organ, or class (SOC) were created to determine any PK-AE relationship.

Most AEs, specifically for the neurological and gastrointestinal SOC, occurred close to $T_{max}$, during the $C_{max}$ period, which for FT218 was around 1.5-2 hours after dosing. These AEs were known AEs associated with sodium oxybate. There appeared to be no clear correlation between individual plasma GHB concentrations levels and AEs between subjects. Individual AEs were equally distributed above and below the mean population $C_{max}$ and $AUC_{inf}$ for the dataset.

Throughout this application, various publications are referenced. The disclosures of these publications in their entireties are hereby incorporated by reference into this application in order to more fully describe the state of the art to which this invention pertains. It will be apparent to those skilled in the art that various modifications and variations may be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Numerous examples are provided herein to enhance the understanding of the present disclosure. In this regard, a specific set of statements are provided below characterizing various examples of oral pharmaceutical compositions and methods of treatment described herein.

Statement 1: An oral pharmaceutical composition for the treatment of narcolepsy, cataplexy, or excessive daytime sleepiness comprising gamma-hydroxybutyrate in a unit dose suitable for administration less than two hours after eating.

Statement 2: The oral pharmaceutical composition of Statement 1, wherein the composition is suitable for administrating with food, immediately after eating, up to 30 minutes after eating, up to 1 hour after eating, up to 1.5 hours after eating, or up to 2 hours after eating.

Statement 3: The oral pharmaceutical composition of Statements 1 or 2, wherein the composition is administered once daily.

Statement 4: The oral pharmaceutical composition of any one of the preceding Statements, wherein the composition is suitable for administration in the evening.

Statement 5: The oral pharmaceutical composition of any one of Statements 1-3, wherein the composition is suitable for administration in the morning.

Statement 6: The oral pharmaceutical composition of any one of the preceding Statements, wherein the composition comprises gamma-hydroxybutyrate in an extended release or delayed release formulation.

Statement 7: The oral pharmaceutical composition of any one of Statements 1-5, wherein the composition comprises gamma-hydroxybutyrate in a modified release formulation.

Statement 8: The oral pharmaceutical composition of any one of the preceding Statements, wherein the composition provides a substantially similar fed state PK profile and 2 hour post meal administration PK profile.

Statement 9: The oral pharmaceutical composition of any one of the preceding Statements, wherein the composition provides a mean $AUC_{inf}$ when administered less than two hour after eating that is 50%-120% of the mean $AUC_{inf}$ when the composition is administered at least two hours after eating.

Statement 10: The oral pharmaceutical composition of any one of the preceding Statements, wherein the composition provides a mean $AUC_{inf}$ when administered less than two hour after eating that is 50%-120% of the mean $AUC_{inf}$ when the composition is administered while fasting.

Statement 11: The oral pharmaceutical composition of any one of the preceding Statements, wherein the composition provides a mean $AUC_{inf}$ when administered less than two hour after eating that is 80%-95% of the mean $AUC_{inf}$ when the composition is administered while fasting.

Statement 12: The oral pharmaceutical composition of any one of the preceding Statements, wherein the composition provides a mean $AUC_{inf}$ when administered less than two hour after eating that is 85%-90% of the mean $AUC_{inf}$ when the composition is administered while fasting.

Statement 13: The oral pharmaceutical composition of any one of the preceding Statements, wherein the composition provides a mean $C_{max}$ when administered less than two hour after eating that is 50%-120% of the mean $C_{max}$ when the composition is administered at least two hours after eating.

Statement 14: The oral pharmaceutical composition of any one of the preceding Statements, wherein the composition provides a mean $C_{max}$ when administered less than two hour after eating that is 50%-120% of the mean $C_{max}$ when the composition is administered while fasting.

Statement 15: The oral pharmaceutical composition of any one of the preceding Statements, wherein the composition provides a mean $C_{max}$ when administered less than two hour after eating that is 55%-80% of the mean $C_{max}$ when the composition is administered while fasting.

Statement 16: The oral pharmaceutical composition of any one of the preceding Statements, wherein the composition provides a mean $C_{max}$ when administered less than two hour after eating that is 60%-75% of the mean $C_{max}$ when the composition is administered while fasting.

Statement 17: The oral pharmaceutical composition of any one of the preceding Statements, wherein the composition provides a $C_{max}$ that is dose proportional.

Statement 18: The oral pharmaceutical composition of any one of the preceding Statements, wherein the composition provides no dose dumping.

Statement 19: The oral pharmaceutical composition of any one of the preceding Statements, wherein there is no significant reduction in safety or efficacy to a patient following administration.

Statement 20: The oral pharmaceutical composition of any one of the preceding Statements, wherein the composition provides an $AUC_{inf}$ bioequivalent to an $AUC_{inf}$ of an equal dose of immediate release liquid solution of sodium oxybate administered at $t_0$ and $t_{4h}$ in equally divided doses at least two hours after eating.

Statement 21: The oral pharmaceutical composition of any one of the preceding Statements, wherein the composition provides a $C_{max}$ that is less than the $C_{max}$ of an equal dose of immediate release liquid solution of sodium oxybate administered at $t_0$ and $t_{4h}$ in equally divided doses at least two hours after eating.

Statement 22: The oral pharmaceutical composition of any one of the preceding Statements, wherein the composition provides a $C_{max}$ that is less than the $C_{max}$ of an equal dose of immediate release liquid solution of sodium oxybate administered at $t_0$ and $t_{4h}$ in equally divided doses less than two hours after eating.

Statement 23: The oral pharmaceutical composition of any one of the preceding Statements, wherein the composition provides a $C_{max}$ that is 10-60% less than the $C_{max}$ of an equal dose of immediate release liquid solution of sodium oxybate administered at $t_0$ and $t_{4h}$ in equally divided doses at least two hours after eating.

Statement 24: The oral pharmaceutical composition of any one of the preceding Statements, wherein the composition provides a $C_{max}$ that is 10-60% less than the $C_{max}$ of an equal dose of immediate release liquid solution of sodium oxybate administered at $t_0$ and $t_{4h}$ in equally divided doses less than two hours after eating.

Statement 25: The oral pharmaceutical composition of any one of the preceding Statements, wherein the composition provides a change in $C_{max}$ between when the composition is administered at least two hours after eating and when the composition is administered less than two hours after eating that is 10-60% less than the change in $C_{max}$ of an equal dose of immediate release liquid solution of sodium oxybate administered at $t_0$ and $t_{4h}$ in equally divided doses at least two hours after eating.

Statement 26: The oral pharmaceutical composition of any one of the preceding Statements, wherein the composition provides a change in $C_{max}$ between when the composition is administered at least two hours after eating and when the composition is administered less than two hours after eating that is 10-60% less than the change in $C_{max}$ of an equal dose of immediate release liquid solution of sodium oxybate administered at $t_0$ and $t_{4h}$ in equally divided doses less than two hours after eating.

Statement 27: The oral pharmaceutical composition of any one of the preceding Statements, wherein the composition provides an AUC that is more dose proportional than the AUC of an equal dose of immediate release liquid solution of sodium oxybate administered at $t_0$ and $t_{4h}$ in equally divided doses at least two hours after eating.

Statement 28: The oral pharmaceutical composition of any one of the preceding Statements, wherein the composition provides an AUC that is more dose proportional than the AUC of an equal dose of immediate release liquid solution of sodium oxybate administered at $t_0$ and $t_{4h}$ in equally divided doses less than two hours after eating.

Statement 29: The oral pharmaceutical composition of any one of Statements 20-28, wherein the equal dose of immediate release liquid solution of sodium oxybate administered at $t_0$ and $t_{4h}$ in equally divided doses is Xyrem®.

Statement 30: An oral pharmaceutical composition for the treatment of narcolepsy, cataplexy, or excessive daytime sleepiness comprising gamma-hydroxybutyrate in a unit dose, wherein the absorption of the gamma-hydroxybutyrate in the gastro-intestinal tract is not substantially changed by the presence of food.

Statement 31: An oral pharmaceutical composition comprising gamma-hydroxybutyrate in a unit dose suitable for administration less than two hours after eating.

Statement 32: The oral pharmaceutical composition of Statement 31, wherein the composition comprises gamma-hydroxybutyrate in a modified release formulation.

Statement 33: The oral pharmaceutical composition of Statements 31 or 32, wherein the formulation is administered during, immediately after, up to 30 minutes after eating, up to 1 hour after eating, up to 1.5 hours after eating, or up to 2 hours after eating.

Statement 34: The oral pharmaceutical composition of any one of Statements 31-33, wherein the composition is suitable for once-daily administration.

Statement 35: The oral pharmaceutical composition of any one of Statements 31-34, wherein the composition is suitable for administration in the evening.

Statement 36: The oral pharmaceutical composition of any one of Statements 31-34, wherein the composition is suitable for administration in the morning.

Statement 37: The oral pharmaceutical composition of any one of Statements 31-36, wherein the composition is effective to induce sleep for at least eight consecutive hours.

Statement 38: The oral pharmaceutical composition of any one of Statements 31-37, wherein a 6 g dose of the composition administered less than two hours after eating has a mean $AUC_{inf}$ of greater than 230 hr*µg/mL, and a mean $C_{max}$ that is from 50% to 140% of the mean $C_{max}$ provided by an equal dose of immediate release liquid solution of sodium oxybate administered at $t_0$ and $t_{4h}$ in equally divided doses at least two hours after eating.

Statement 39: The oral pharmaceutical composition of Statement 38, wherein the mean $C_{max}$ is from 80% to 140% of the mean $C_{max}$ provided by an equal dose of immediate release liquid solution of sodium oxybate administered at $t_0$ and $t_{4h}$ in equally divided doses at least two hours after eating.

Statement 40: The oral pharmaceutical composition of Statement 38, wherein the mean $C_{max}$ is from 100% to 150% of the of the mean $C_{max}$ of a first peak of the equal dose of immediate release liquid solution of sodium oxybate administered at to and $t_{4h}$ in equally divided doses at least two hours after eating.

Statement 41: The oral pharmaceutical composition of Statement 38, wherein the mean $C_{max}$ is from 80% to 100% of the of the mean $C_{max}$ of a second peak of the equal dose of immediate release liquid solution of sodium oxybate administered at to and tan in equally divided doses at least two hours after eating.

Statement 42: The oral pharmaceutical composition of Statement 38, wherein the mean $C_{max}$ is about 50 µg/mL to about 82 µg/mL.

Statement 43: The oral pharmaceutical composition of Statement 42, wherein the mean $C_{max}$ is about 64 µg/mL.

Statement 44: The oral pharmaceutical composition of Statement 38, wherein the mean $AUC_{inf}$ is about 242 hr*µg/mL when the formulation is administered about 30 minutes after eating.

Statement 45: The oral pharmaceutical composition of Statement 38, wherein the mean $AUC_{inf}$ is about 273 hr*µg/mL when the formulation is administered about 2 hours after eating.

Statement 46: A method of treating narcolepsy and associated disorders and symptoms in a patient in need thereof comprising: administering an oral pharmaceutical composition comprising gamma-hydroxybutyrate less than two hours after eating.

Statement 47: The method of Statement 46, wherein the composition is administered once-daily.

Statement 48: The method of Statement 47, wherein the composition is administered after eating in the evening.

Statement 49: The method of Statement 47, wherein the composition is administered after eating in the morning.

Statement 50: The method of any one of Statements 46-49, wherein the composition is administered during, immediately after eating, up to 30 minutes after eating, up to 1 hour after eating, up to 1.5 hours after eating, or up to 2 hours after eating.

Statement 51: The method of any one of Statements 46-50, wherein the composition is effective to induce sleep for at least six consecutive hours.

Statement 52: The method of any one of Statements 46-51, wherein the composition is effective to induce sleep for at least eight consecutive hours.

Statement 53: The method of any one of Statements 46-52, wherein the composition is effective to induce sleep for at least ten consecutive hours.

Statement 54: The method of any one of Statements 46-53, wherein the composition comprises gamma-hydroxybutyrate in an extended release or delayed release formulation.

Statement 55: The method of any one of Statements 46-53, wherein the composition comprises gamma-hydroxybutyrate in a modified release formulation.

Statement 56: The method of any one of Statements 46-55, wherein the composition provides a substantially similar fed state PK profile and 2 hour post meal administration PK profile.

Statement 57: The method of any one of Statements 46-56, wherein the composition provides a mean $AUC_{inf}$ when administered less than two hour after eating that is 50%-120% of the mean $AUC_{inf}$ when the composition is administered at least two hours after eating.

Statement 58: The method of any one of Statements 46-57, wherein the composition provides a mean $AUC_{inf}$ when administered less than two hour after eating that is 50%-120% of the mean $AUC_{inf}$ when the composition is administered while fasting.

Statement 59: The method of any one of Statements 46-58, wherein the composition provides a mean $AUC_{inf}$ when administered less than two hour after eating that is 80%-95% of the mean $AUC_{inf}$ when the composition is administered while fasting.

Statement 60: The method of any one of Statements 46-59, wherein the composition provides a mean $AUC_{inf}$ when administered less than two hour after eating that is 85%-90% of the mean $AUC_{inf}$ when the composition is administered while fasting.

Statement 61: The method of any one of Statements 46-60, wherein the composition provides a mean $C_{max}$ when administered less than two hour after eating that is 50%-120% of the mean $C_{max}$ when the composition is administered at least two hours after eating.

Statement 62: The method of any one of Statements 46-61, wherein the composition provides a mean $C_{max}$ when administered less than two hour after eating that is 50%-120% of the mean $C_{max}$ when the composition is administered while fasting.

Statement 63: The method of any one of Statements 46-62, wherein the composition provides a mean $C_{max}$ when administered less than two hour after eating that is 55%-80% of the mean $C_{max}$ when the composition is administered while fasting.

Statement 64: The method of any one of Statements 46-63, wherein the composition provides a mean $C_{max}$ when administered less than two hour after eating that is 60%-75% of the mean $C_{max}$ when the composition is administered while fasting.

Statement 65: The method of any one of Statements 46-64, wherein the composition provides a $C_{max}$ that is dose proportional.

Statement 66: The method of any one of Statements 46-65, wherein the composition provides no dose dumping.

Statement 67: The method of any one of Statements 46-66, wherein there is no significant reduction in safety or efficacy to a patient following administration.

Statement 68: The method of any one of Statements 46-67, wherein the composition provides an $AUC_{inf}$ bioequivalent to an $AUC_{inf}$ of an equal dose of immediate release liquid solution of sodium oxybate administered at to and tan in equally divided doses at least two hours after eating.

Statement 69: The method of any one of Statements 46-68, wherein the composition provides a $C_{max}$ that is less than the $C_{max}$ of an equal dose of immediate release liquid solution of sodium oxybate administered at $t_0$ and $t_{4h}$ in equally divided doses at least two hours after eating.

Statement 70: The method of any one of Statements 46-69, wherein the composition provides a $C_{max}$ that is less than the $C_{max}$ of an equal dose of immediate release liquid solution of sodium oxybate administered at to and tan in equally divided doses less than two hours after eating.

Statement 71: The method of any one of Statements 46-70, wherein the composition provides a $C_{max}$ that is 10-60% less than the $C_{max}$ of an equal dose of immediate release liquid solution of sodium oxybate administered at $t_0$ and $t_{4h}$ in equally divided doses at least two hours after eating.

Statement 72: The method of any one of Statements 46-71, wherein the composition provides a $C_{max}$ that is 10-60% less than the $C_{max}$ of an equal dose of immediate release liquid solution of sodium oxybate administered at $t_0$ and $t_{4h}$ in equally divided doses less than two hours after eating.

Statement 73: The method of any one of Statements 46-72, wherein the composition provides a change in $C_{max}$ between when the composition is administered at least two hours after eating and when the composition is administered less than two hours after eating that is 10-60% less than the change in $C_{max}$ of an equal dose of immediate release liquid solution of sodium oxybate administered at $t_0$ and $t_{4h}$ in equally divided doses at least two hours after eating.

Statement 74: The method of any one of Statements 46-73, wherein the composition provides a change in $C_{max}$ between when the composition is administered at least two hours after eating and when the composition is administered less than two hours after eating that is 10-60% less than the change in $C_{max}$ of an equal dose of immediate release liquid solution of sodium oxybate administered at $t_0$ and $t_{4h}$ in equally divided doses less than two hours after eating.

Statement 75: The method of any one of Statements 46-74, wherein the composition provides an AUC that is more dose proportional than the AUC of an equal dose of immediate release liquid solution of sodium oxybate administered at to and $t_{4h}$ in equally divided doses at least two hours after eating.

Statement 76: The method of any one of Statements 46-75, wherein the equal dose of immediate release liquid solution of sodium oxybate administered at to and $t_{4h}$ in equally divided doses is Xyrem®.

Statement 77: The method of any one of Statements 46-76, wherein a 6 g dose of the composition administered has been shown to achieve a mean $AUC_{inf}$ of greater than 230 hr*μg/mL, and a mean $C_{max}$ that is from 50% to 140% of the mean $C_{max}$ provided by an equal dose of immediate release liquid solution of sodium oxybate administered at $t_0$ and $t_{4h}$ in equally divided doses at least two hours after eating.

Statement 78: The method of Statement 77, wherein the mean Cmax is from 80% to 140% of the mean $C_{max}$ provided by an equal dose of immediate release liquid solution of sodium oxybate administered at $t_0$ and $t_{4h}$ in equally divided doses approximately two hours after eating.

Statement 79: The method of any one of Statements 77-78, wherein the mean $C_{max}$ is from 100% to 150% of the of the mean $C_{max}$ of a first peak of the equal dose of immediate release liquid solution of sodium oxybate administered at $t_0$ and $t_{4h}$ in equally divided doses at least two hours after eating.

Statement 80: The method of any one of Statements 77-79, wherein the mean $C_{max}$ is from 80% to 100% of the of the mean $C_{max}$ of a second peak of the equal dose of immediate release liquid solution of sodium oxybate administered at to and $t_{4h}$ in equally divided doses approximately two hours after eating.

Statement 81: The method of any one of Statements 77-80, wherein the mean $C_{max}$ is about 50 μg/mL to about 82 μg/mL.

Statement 82: The method of Statement 81, wherein the mean $C_{max}$ is about 64 μg/mL.

Statement 83: The method of any one of Statements 77-82, wherein the mean $AUC_{inf}$ is about 242 hr*μg/mL when the formulation is administered about 30 minutes after eating.

Statement 84: The method of any one of Statements 77-82, wherein the mean $AUC_{inf}$ is about 273 hr*μg/mL when the formulation is administered about 2 hours after eating.

Statement 85: An oral pharmaceutical composition for the treatment of narcolepsy, cataplexy, or excessive daytime sleepiness comprising gamma-hydroxybutyrate in a unit dose suitable for administration once daily, wherein the composition is dose proportional.

Statement 86: The oral pharmaceutical composition of Statement 85, wherein the composition is suitable for administration in the evening.

Statement 87: The oral pharmaceutical composition of Statement 85, wherein the composition is suitable for administration in the morning.

Statement 88: The oral pharmaceutical composition of any one of Statements 85-87, wherein the composition is dose proportional across 4.5 g, 7.5 g, and 9 g doses of the composition.

Statement 89: The oral pharmaceutical composition of any one of Statements 85-88, wherein the $C_{max}$ of the composition is proportional across 4.5 g, 7.5 g, and 9 g doses of the composition.

Statement 90: The oral pharmaceutical composition of any one of Statements 85-89, wherein the composition is dose proportional by a factor of 1 to 1.3.

Statement 91: The oral pharmaceutical composition of any one of Statements 88-90, wherein median $T_{max}$ is between about 1.5 and 2 hours across the increasing doses.

Statement 92: The oral pharmaceutical composition of any one of Statements 88-97, wherein the mean $C_{max}$ is between about 42.9 and 84.5 μg/mL across the increasing doses.

Statement 93: The oral pharmaceutical composition of any one of Statements 88-92, wherein the mean $AUC_{inf}$ is about 191, 358 and 443 μg·h/mL for the 4.5, 7.5 and 9 g doses respectively.

Statement 94: The oral pharmaceutical composition of any one of Statements 88-93, wherein the mean concentrations at 8 hours are about 4.8, 19.7 and 25.5 μg/mL for the 4.5, 7.5 and 9 g doses respectively.

Statement 95: A method of treating narcolepsy and associated disorders and symptoms in a patient in need thereof comprising: administering an oral pharmaceutical composition comprising gamma-hydroxybutyrate once daily, wherein the composition is dose proportional.

Statement 96: The method of Statement 95, wherein the composition is administered in the evening.

Statement 97: The method of Statement 95, wherein the composition is administered in the morning.

Statement 98: The method of any one of Statements 95-97, wherein the composition is dose proportional across 4.5 g, 7.5 g, and 9 g doses of the composition.

Statement 99: The method of any one of Statements 95-98, wherein the $C_{max}$ of the composition is proportional across 4.5 g, 7.5 g, and 9 g doses of the composition.

Statement 100: The method of any one of Statements 95-99, wherein the composition is dose proportional by a factor of 1 to 1.3.

Statement 101: The method of any one of Statements 98-100, wherein median $T_{max}$ is between about 1.5 and 2 hours across the increasing doses.

Statement 102: The method of any one of Statements 98-101, wherein the mean $C_{max}$ is between about 42.9 and 84.5 μg/mL across the increasing doses.

Statement 103: The method of any one of Statements 98-102, wherein the mean $AUC_{inf}$ is about 191, 358 and 443 μg·h/mL for the 4.5, 7.5 and 9 g doses respectively.

Statement 104: The method of any one of Statements 98-103, wherein the mean concentrations at 8 hours are about 4.8, 19.7 and 25.5 μg/mL for the 4.5, 7.5 and 9 g doses respectively.

Statement 105: An oral pharmaceutical composition for the treatment of narcolepsy, cataplexy, or excessive daytime sleepiness comprising gamma-hydroxybutyrate in a unit dose suitable for administration once daily, wherein most adverse events (AEs) occur close to $T_{max}$, during the $C_{max}$ period.

Statement 106: The oral pharmaceutical composition of Statement 105, wherein most AEs occur 1.5-2 hours after dosing.

Statement 107: The oral pharmaceutical composition of Statements 105 or 106, wherein administration of the oral pharmaceutical composition less than two hours after eating results in fewer AEs than administration of the oral pharmaceutical composition at least two hours after eating.

Statement 108: The oral pharmaceutical composition of any one of Statements 105-107, wherein the oral pharmaceutical composition has a more favorable safety profile as compared to an equal dose of immediate release liquid solution of sodium oxybate administered at $t_0$ and $t_{4h}$ in equally divided doses.

Statement 109: The oral pharmaceutical composition of any one of Statements 105-108, wherein administration of the oral pharmaceutical composition once daily results in fewer AEs than administration of an equal dose of immediate release liquid solution of sodium oxybate administered at $t_0$ and $t_{4h}$ in equally divided doses.

Statement 110: A method of treating narcolepsy and associated disorders and symptoms in a patient in need thereof comprising: administering an oral pharmaceutical composition comprising gamma-hydroxybutyrate once daily, wherein most AEs occur close to $T_{max}$, during the $C_{max}$ period.

Statement 111: The method of Statement 110, wherein most AEs occur 1.5-2 hours after dosing.

Statement 112: The method of Statements 110 or 111, wherein administration of the oral pharmaceutical composition less than two hours after eating results in fewer AEs than administration of the oral pharmaceutical composition at least two hours after eating.

Statement 113: The method of any one of Statements 110-112, wherein the oral pharmaceutical composition has a more favorable safety profile as compared to an equal dose of immediate release liquid solution of sodium oxybate administered at $t_0$ and $t_{4h}$ in equally divided doses.

Statement 114: The method of any one of Statements 110-113, wherein administration of the oral pharmaceutical composition once daily results in fewer AEs than administration of an equal dose of immediate release liquid solution of sodium oxybate administered at $t_0$ and $t_{4h}$ in equally divided doses.

Statement 115: The method of any one of Statements 110-114, wherein the amount of AEs are reduced over an 8 hour, 12 hour, 16 hour, 20 hour, 24 hour, and/or 48 hour time period following administration of the oral pharmaceutical composition, as compared to an equal dose of an immediate release sodium oxybate formulation administered more frequently than once-daily.

Statement 116: A method of reducing the amount of adverse events (AEs) in a patient with narcolepsy, cataplexy, or excessive daytime sleepiness comprising: administering an oral pharmaceutical composition comprising gamma-hydroxybutyrate once daily, wherein the gamma-hydroxybutyrate composition has fewer $C_{max}$ periods than an equal dose of immediate release sodium oxybate formulation administered more frequently than once-daily.

Statement 117: The method of Statement 116, wherein administration of the gamma-hydroxybutyrate composition results in fewer adverse events and fewer $C_{max}$ periods over an 8 hour, 12 hour, 16 hour, 20 hour, 24 hour, and/or 48 hour time period, as compared to the immediate release sodium oxybate formulation administered more frequently than once-daily.

Statement 118: The method of Statements 116 or 117, wherein the gamma-hydroxybutyrate composition has a superior safety profile compared to the immediate release sodium oxybate formulation administered more frequently than once-daily.

What is claimed is:

1. A method of decreasing excessive daytime sleepiness in a human subject, the method comprising:
    orally administering a pharmaceutical composition comprising calcium oxybate, magnesium oxybate, and potassium oxybate,
    wherein the orally administering occurs only once nightly at least two hours after eating.

2. The method of claim 1, wherein the pharmaceutical composition comprises calcium oxybate, magnesium oxybate, potassium oxybate, and sodium oxybate.

3. The method of claim 1, wherein orally administering achieves a mean AUCinf of about 273 hr*µg/mL when administration is about 2 hours after eating.

4. The method of claim 1, wherein orally administering achieves a tmax of greater than 1 hour.

5. The method of claim 1, wherein orally administering is effective to induce sleep for at least six consecutive hours.

6. The method of claim 1, wherein orally administering is effective to induce sleep for at least eight consecutive hours.

7. The method of claim 1, wherein the human subject achieves a decrease in excessive daytime sleepiness when measured by the Epworth Sleepiness Scale (ESS).

8. The method of claim 1, wherein the human subject achieves a decrease in excessive daytime sleepiness when measured by the Maintenance of Wakefulness Test.

9. The method of claim 1, wherein the human subject achieves an improved Clinical Global Impression (CGI) rating of sleepiness.

10. The method of claim 1, wherein the human subject achieves a decrease in weekly cataplexy attacks.

11. The method of claim 1, comprising mixing the pharmaceutical composition with water prior to orally administering.

12. The method of claim 1, wherein the pharmaceutical composition comprises a powder.

13. The method of claim 1, wherein the pharmaceutical composition comprises viscosifying or suspending agents.

14. The method of claim 1, wherein the pharmaceutical composition comprises an immediate release portion.

15. The method of claim 14, wherein the immediate release portion releases at least 80% of its gamma-hydroxybutyrate salt in 1 hour when tested in a dissolution apparatus 2 according to USP 38<711> in a 0.1 N HCl dissolution medium at a temperature of 37° C. and a paddle speed of 75 rpm.

16. The method of claim 1, wherein the pharmaceutical composition comprises an immediate release portion and modified release portion.

17. The method of claim 16, wherein the immediate release portion comprises calcium oxybate, magnesium oxybate, and potassium oxybate.

18. The method of claim 16, wherein the modified release portion comprises sodium oxybate.

19. The method of claim 1, wherein the pharmaceutical composition comprises crystals or spheres.

20. The method of claim 19, wherein the crystals or spheres comprise lactose, sucrose, or microcrystalline cellulose.

21. The method of claim 1, wherein the pharmaceutical composition comprises spheres or granules.

22. The method of claim 21, wherein the spheres comprising sucrose.

23. The method of claim 21, wherein the spheres comprise maltodextrin.

\* \* \* \* \*

UNITED STATES PATENT AND TRADEMARK OFFICE
CERTIFICATE OF CORRECTION

| | | |
|---|---|---|
| PATENT NO. | : 12,167,991 B2 | Page 1 of 1 |
| APPLICATION NO. | : 18/758344 | |
| DATED | : December 17, 2024 | |
| INVENTOR(S) | : Julien Grassot, Cendrine Grangeon and Jordan Dubow | |

It is certified that error appears in the above-identified patent and that said Letters Patent is hereby corrected as shown below:

On the Title Page

Item (72) Inventors, cancel the text reading:
"Jordan Dubow, Lyons (FR)"
And replace it with:
--Jordan Dubow, Chicago, IL--

Signed and Sealed this
Twenty-fifth Day of February, 2025

Coke Morgan Stewart
*Acting Director of the United States Patent and Trademark Office*